(12) United States Patent
Metcalfe et al.

(10) Patent No.: US 12,727,946 B2
(45) Date of Patent: Sep. 8, 2026

(54) ORTHOPAEDIC IMPLANT SYSTEMS INCLUDING TRANSFER FEATURES AND METHODS FOR PLAN TRANSFER

(71) Applicant: ARTHREX, INC., Naples, FL (US)

(72) Inventors: Nick Metcalfe, Bonita Springs, FL (US); Steven Jim DeLeon, Naples, FL (US)

(73) Assignee: ARTHREX, INC., Naples, FL (US)

( * ) Notice: Subject to any disclaimer, the term of this patent is extended or adjusted under 35 U.S.C. 154(b) by 0 days.

(21) Appl. No.: 19/053,680

(22) Filed: Feb. 14, 2025

(65) Prior Publication Data

US 2025/0186124 A1 Jun. 12, 2025

Related U.S. Application Data

(63) Continuation of application No. 17/725,586, filed on Apr. 21, 2022, now Pat. No. 12,256,997.

(60) Provisional application No. 63/180,239, filed on Apr. 27, 2021.

(51) Int. Cl.

| | |
|---|---|
| ***A61B 17/17*** | (2006.01) |
| ***A61B 17/56*** | (2006.01) |
| ***A61B 34/10*** | (2016.01) |

(52) U.S. Cl.
CPC .......... *A61B 34/10* (2016.02); *A61B 17/1725* (2013.01); *A61B 17/56* (2013.01); *A61B 2034/102* (2016.02); *A61B 2034/107* (2016.02)

(58) Field of Classification Search
CPC . A61B 17/1725; A61B 17/1778; A61B 17/56; A61B 2017/568; A61B 2034/102; A61B 2034/105; A61B 2034/107; A61B 2034/108; A61B 34/10; A61B 34/25; A61F 2/30734; A61F 2/30744; A61F 2/30942; A61F 2/4081; A61F 2/4612; A61F 2002/30354; A61F 2002/30398; A61F 2002/30617; A61F 2002/30736; A61F 2002/30985; A61F 2002/4085;
(Continued)

(56) References Cited

U.S. PATENT DOCUMENTS

| | | | |
|---|---|---|---|
| 6,231,611 | B1 | 5/2001 | Mosseri |
| 6,395,005 | B1 | 5/2002 | Lovell |
| 7,931,690 | B1 | 4/2011 | Bonutti |

(Continued)

FOREIGN PATENT DOCUMENTS

| | | | |
|---|---|---|---|
| EP | 1273269 | A2 | 1/2003 |
| EP | 3498227 | A1 | 6/2019 |

(Continued)

OTHER PUBLICATIONS

European Search Report for European Patent Application No. 25184707.5 mailed Aug. 20, 2025.

(Continued)

*Primary Examiner* — Samuel S Hanna
(74) *Attorney, Agent, or Firm* — Carlson, Gaskey & Olds, P.C.

(57) ABSTRACT

This disclosure relates to planning systems, assemblies and methods. The planning systems, assemblies and methods disclosed herein may be utilized for planning and implementing orthopaedic procedures to restore functionality to a joint, and may include one or more transfer members for positioning implants relative to patient anatomy.

11 Claims, 51 Drawing Sheets

(58) Field of Classification Search
CPC ...... A61F 2002/4629; A61F 2002/4687; A61F 2002/30561
See application file for complete search history.

(56) References Cited

U.S. PATENT DOCUMENTS

| | | | |
|---|---|---|---|
| 8,303,665 | B2 | 11/2012 | Tornier et al. |
| 8,361,076 | B2 | 1/2013 | Roose et al. |
| 8,594,395 | B2 | 11/2013 | Roose et al. |
| 8,632,597 | B2 | 1/2014 | Lappin |
| 8,696,680 | B2 | 4/2014 | Iannotti et al. |
| 8,702,717 | B2 | 4/2014 | Rauscher et al. |
| 8,747,418 | B2 | 6/2014 | Qureshi et al. |
| 8,801,725 | B2 | 8/2014 | Ritter et al. |
| 8,852,283 | B2 | 10/2014 | Tornier et al. |
| 8,926,627 | B2 | 1/2015 | Iannotti et al. |
| 8,940,054 | B2 | 1/2015 | Wiley et al. |
| 8,992,538 | B2 | 3/2015 | Keefer |
| 9,033,990 | B2 | 5/2015 | Iannotti et al. |
| 9,114,017 | B2 | 8/2015 | Lappin |
| 9,198,732 | B2 | 12/2015 | Iannotti et al. |
| 9,226,830 | B2 | 1/2016 | De Wilde et al. |
| 9,233,003 | B2 | 1/2016 | Roche et al. |
| 9,283,083 | B2 | 3/2016 | Winslow et al. |
| 9,345,497 | B2 | 5/2016 | Gonzalvez et al. |
| 9,452,055 | B2 | 9/2016 | Lappin |
| 9,480,580 | B2 | 11/2016 | White et al. |
| 9,492,182 | B2 | 11/2016 | Keefer |
| 9,526,514 | B2 | 12/2016 | Kelley et al. |
| 9,532,880 | B2 | 1/2017 | Lappin |
| 9,545,312 | B2 | 1/2017 | Tornier et al. |
| 9,579,107 | B2 | 2/2017 | Schoenefeld |
| 9,629,725 | B2 | 4/2017 | Gargac et al. |
| 9,700,325 | B2 | 7/2017 | Schoenefeld |
| 9,717,508 | B2 | 8/2017 | Iannotti et al. |
| 9,741,263 | B2 | 8/2017 | Iannotti et al. |
| 9,826,994 | B2 | 11/2017 | Eash et al. |
| 9,844,440 | B2 | 12/2017 | Kovacs et al. |
| 9,931,168 | B2 | 4/2018 | Brown et al. |
| 10,028,803 | B2 | 7/2018 | O'Neill et al. |
| 10,034,757 | B2 | 7/2018 | Kovacs et al. |
| 10,130,378 | B2 | 11/2018 | Bryan |
| 10,265,184 | B2 | 4/2019 | Lappin |
| 10,271,858 | B2 | 4/2019 | Guilloux et al. |
| 10,299,807 | B2 | 5/2019 | Murphy |
| 10,357,373 | B2 | 7/2019 | Gargac et al. |
| 10,357,378 | B2 | 7/2019 | Borries et al. |
| 10,376,270 | B2 | 8/2019 | Eash |
| 10,383,735 | B2 | 8/2019 | Wiley et al. |
| 10,405,928 | B2 | 9/2019 | Falardeau et al. |
| 10,433,983 | B1 | 10/2019 | Khosla et al. |
| 10,617,434 | B2 | 4/2020 | Theiss et al. |
| 10,813,774 | B2 | 10/2020 | Davenport et al. |
| 10,828,111 | B2 | 11/2020 | Frank et al. |
| 10,925,658 | B2 | 2/2021 | Hopkins |
| 11,471,290 | B2 * | 10/2022 | Nelson ................ A61F 2/30749 |
| 2013/0245632 | A1 | 9/2013 | Iannotti et al. |
| 2015/0105696 | A1 | 4/2015 | Litke et al. |
| 2015/0140507 | A1 | 5/2015 | Moffson et al. |
| 2015/0190151 | A1 | 7/2015 | Budhabhatti et al. |
| 2015/0305891 | A1 | 10/2015 | Bergin et al. |
| 2016/0184109 | A1 | 6/2016 | Davenport et al. |
| 2016/0242933 | A1 | 8/2016 | Deransart et al. |
| 2017/0079742 | A1 | 3/2017 | O'Neill et al. |
| 2017/0095336 | A1 | 4/2017 | Tornier et al. |
| 2017/0265873 | A1 | 9/2017 | Schoenefeld |
| 2018/0049897 | A1 | 2/2018 | Lathers et al. |
| 2018/0125509 | A1 | 5/2018 | Iannotti et al. |
| 2018/0303618 | A1 | 10/2018 | Kovacs et al. |
| 2018/0333263 | A1 | 11/2018 | Roby et al. |
| 2018/0333268 | A1 | 11/2018 | Cardon et al. |
| 2018/0360512 | A1 | 12/2018 | Mari |
| 2019/0015116 | A1 | 1/2019 | Gargac et al. |
| 2019/0015117 | A1 | 1/2019 | Neichel et al. |
| 2019/0015118 | A1 | 1/2019 | Neichel et al. |
| 2019/0015221 | A1 | 1/2019 | Neichel et al. |
| 2019/0151106 | A1 | 5/2019 | Kovacs et al. |
| 2019/0159848 | A1 | 5/2019 | Quaid et al. |
| 2019/0159907 | A1 | 5/2019 | Roche et al. |
| 2019/0240035 | A1 | 8/2019 | Lappin |
| 2019/0298537 | A1 | 10/2019 | Gargac et al. |
| 2019/0343658 | A1 | 11/2019 | Deransart et al. |
| 2019/0380792 | A1 | 12/2019 | Poltaretskyi et al. |
| 2020/0197185 | A1 | 6/2020 | Mahfouz |
| 2022/0296259 | A1 | 9/2022 | Shah |

FOREIGN PATENT DOCUMENTS

| | | | |
|---|---|---|---|
| KR | 102053599 | B1 | 1/2020 |
| WO | 2012024288 | A2 | 2/2012 |
| WO | 2012166888 | A2 | 12/2012 |
| WO | 2013152182 | A1 | 10/2013 |
| WO | 2014089291 | A1 | 6/2014 |
| WO | 2017007565 | A2 | 1/2017 |
| WO | 2017165346 | A1 | 9/2017 |
| WO | 2018052965 | A1 | 3/2018 |
| WO | 2018081073 | A1 | 5/2018 |
| WO | 2019014278 | A1 | 1/2019 |
| WO | 2020102886 | A1 | 5/2020 |
| WO | 2020255152 | A1 | 12/2020 |
| WO | 2021021247 | A1 | 2/2021 |

OTHER PUBLICATIONS

Canadian Office Action for Canadian Patent Application No. 3,216,633 mailed May 1, 2025.
International Preliminary Report on Patentability for International Application No. PCT/US2022/024795 mailed Nov. 9, 2023.
International Search Report for International Application No. PCT/US2022/024795 mailed Sep. 19, 2022.
Musculoskeletal Key. Arthrex Univers Revers (TM) shoulder prosthesis. Retrieve from: https://musculoskeletalkey.com/arthrex-univers-revers-shoulder-prosthesis/.
Canadian Office Action for Canadian Patent Application No. 3,216,633 mailed May 21, 2026.

* cited by examiner

BREAK
750
752
754
754B
754I
758
758C
758P
760
760P
761B
772
CP
B
S
GP
D1
F
X

ORTHOPAEDIC IMPLANT SYSTEMS INCLUDING TRANSFER FEATURES AND METHODS FOR PLAN TRANSFER

CROSS-REFERENCE TO RELATED APPLICATION

The present disclosure is a continuation of U.S. application Ser. No. 17/725,586 filed Apr. 21, 2022, which claims priority to U.S. Provisional Application No. 63/180,239 filed Apr. 27, 2021.

BACKGROUND

This disclosure relates to orthopaedic procedures and, more particularly, to systems and methods for planning and implementing the repair of bone defects and restoration of functionality to a joint, including positioning implants at a surgical site based on a surgical plan.

Many bones of the human musculoskeletal system include articular surfaces. The articular surfaces articulate relative to other bones to facilitate different types and degrees of joint movement. The articular surfaces can erode or experience bone loss over time due to repeated use or wear or can fracture as a result of a traumatic impact. These types of bone defects can cause joint instability and pain.

Bone deficiencies may occur along the articular surfaces. Some techniques utilize a bone graft and/or implant to repair a defect adjacent the articular surfaces. The surgeon may utilize a guide pin to position the implant.

SUMMARY

This disclosure relates to planning systems, assemblies and methods.

The planning systems, assemblies and methods disclosed herein may be utilized for planning and implementing orthopaedic procedures to restore functionality to a joint. Implants may be positioned utilizing one or more transfer members associated with a surgical plan.

A transfer guide for an orthopaedic procedure according to an exemplary aspect of this disclosure may include, inter alia, a guide body that may be configured to be coupled to an implant and one or more transfer members that may extend from the guide body. The one or more transfer members may be configured to contact tissue.

An orthopaedic implant according to an exemplary aspect of this disclosure may include, inter alia, a baseplate and an augment that may extend outwardly from the baseplate. The augment may be dimensioned to contact bone. The implant may include one or more transfer members that may extend from the augment. The one or more transfer members may be configured to contact bone. Each of the one or more transfer members may be coupled to the augment at a respective breakable connection.

An assembly for an orthopaedic procedure according to an exemplary aspect of this disclosure may include, inter alia, an implant that may be configured to abut bone and a transfer guide. The transfer guide may include a guide body that may be configured to be coupled to the implant and one or more transfer members that may extend from the guide body. The one or more transfer members may be configured to contact bone.

A method of installing an orthopaedic implant according to an exemplary aspect of this disclosure may include, inter alia, positioning one or more transfer members to contact bone. The one or more transfer members may be coupled to an implant. The method may include positioning the implant relative to the bone based on the positioning of the one or more transfer members.

The various features and advantages of this disclosure will become apparent to those skilled in the art from the following detailed description. The drawings that accompany the detailed description can be briefly described as follows.

BRIEF DESCRIPTION OF THE DRAWINGS

Like reference numbers and designations in the various drawings indicate like elements.

DETAILED DESCRIPTION

Figure 1:
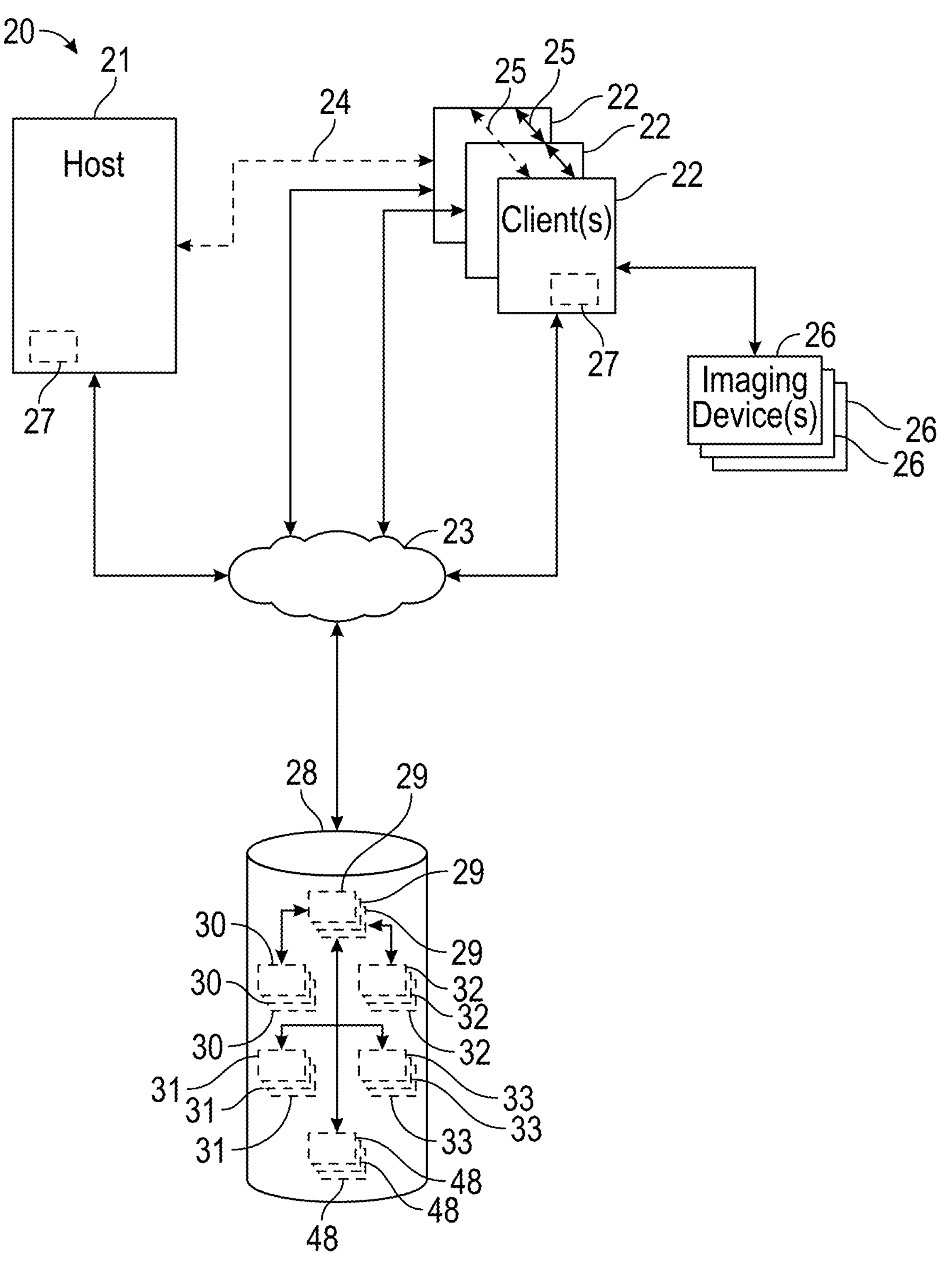
FIG. 1 illustrates an exemplary planning system.

This disclosure relates to surgical planning and implementation, including positioning implants relative to patient anatomy. The planning systems, assemblies and methods disclosed herein may be utilized for planning and implementing orthopaedic procedures to restore functionality to a joint. Implants may be positioned utilizing one or more transfer members.

Transfer members may be associated with a predetermined surgical plan. One or more parameters of the surgical plan may be transferred to or by the transfer members for implementing a predetermined position of the respective implant. The surgical plan may be tailored to the individual patient, which may improve healing. The transfer members may be coupled directly to the implant or may be incorporated into a transfer guide or device, which may improve accuracy in positioning implants according to surgical plans. The disclosed techniques may reduce complexity in implementing the surgical plans, including reduced packaging and instrumentation. The transfer members may be single use and/or reusable, which may provide the surgeon flexibility in implementing the surgical plans.

A transfer guide for an orthopaedic procedure according to an exemplary aspect of this disclosure may include a guide body that may be configured to be coupled to an implant and one or more transfer members that may extend from the guide body. The one or more transfer members may be configured to contact tissue.

In a further implementation, the guide body may include a passage dimensioned to at least partially receive a guide pin insertable in bone.

In a further implementation, the one or more transfer members may be positioned relative to the guide body based on a predetermined surgical plan.

In a further implementation, the one or more transfer members may be moveable relative to the guide body.

In a further implementation, the one or more transfer members may include a plurality of transfer members circumferentially distributed about a periphery of the guide body.

In a further implementation, each of the transfer members may include a first portion extending radially outward from the guide body and a second portion extending axially from the first portion. The second portion may be configured to contact tissue.

In a further implementation, each of the transfer members may include a third portion that extends from the first portion. The third portion may be translatable along a respective slot established in the periphery of the guide body to set a position of the terminal end portion relative to the guide body.

In a further implementation, the first portion and the second portion may establish a substantially L-shaped geometry.

In a further implementation, the one or more transfer members may be integrally formed with the guide body.

An orthopaedic implant according to an exemplary aspect of this disclosure may include a baseplate and an augment that may extend outwardly from the baseplate. The augment may be dimensioned to contact bone. The implant may include one or more transfer members that may extend from the augment. The one or more transfer members may be configured to contact bone. Each of the one or more transfer members may be coupled to the augment at a respective breakable connection.

In a further implementation, the one or more transfer members may be dimensioned based on a predetermined surgical plan.

In a further implementation, the one or more transfer members may be integrally formed with the augment.

In a further implementation, the augment may be formed along the baseplate.

In a further implementation, the breakable connection may be configured to sever in response to a predetermined quantity of torque at an interface.

In a further implementation, the breakable connection may be configured to sever in response to the predetermined quantity of torque in a first rotational direction with respect to an axis extending through the interface, but not a second rotational direction opposed to the first rotational direction.

In a further implementation, the one or more transfer members may include a plurality of transfer members circumferentially distributed about a periphery of the augment.

In a further implementation, each of the transfer members may include a first portion extending radially outward from the periphery of the augment and a second portion extending axially from the first portion. The terminal end portion may be configured to contact tissue.

In a further implementation, the breakable connection may be configured to sever in response to a predetermined quantity of torque in a first rotational direction with respect to an axis extending through the second portion, but not a second rotational direction opposed to the first rotational direction.

In a further implementation, the baseplate may include a central aperture and a plurality of peripheral apertures circumferentially distributed about the central aperture. Each of the peripheral apertures may be aligned with a respective passage through the augment. Each of the peripheral apertures may be dimensioned to receive a respective fastener partially receivable through the respective passage and into bone.

In a further implementation, the central aperture may be dimensioned to receive a guide pin insertable into bone to set a position of the implant.

An assembly for an orthopaedic procedure according to an exemplary aspect of this disclosure may include an implant that may be configured to abut bone and a transfer guide. The transfer guide may include a guide body that may be configured to be coupled to the implant and one or more transfer members that may extend from the guide body. The one or more transfer members may be configured to contact bone.

In a further implementation, the guide body may include a passage dimensioned to at least partially receive a guide pin insertable in bone to set a position of the implant.

In a further implementation, the one or more transfer members may be positioned relative to the guide body based on a predetermined surgical plan.

In a further implementation, the implant may include a baseplate and an augment that may extend from the baseplate relative to an axis. The augment may be dimensioned to contact bone.

In a further implementation, the one or more transfer members may be dimensioned to be at least partially axially aligned with the augment relative to the axis.

In a further implementation, the augment may include an augment body extending between a first face and a second face. The first face may extend along the baseplate. The second face may be dimensioned to substantially follow a contour of the bone.

In a further implementation, the guide body may include first threads that may mate with second threads along the baseplate to mechanically attach the transfer guide to the implant.

In a further implementation, the baseplate may include a central aperture and a plurality of peripheral apertures circumferentially distributed about the central aperture. Each of the peripheral apertures may be dimensioned to receive a respective fastener to secure the implant to bone. The transfer guide may include an alignment member. The alignment member may be dimensioned to be insertable into an aperture along the baseplate to limit relative rotation between the transfer guide and the implant.

In a further implementation, the guide body may include a passage configured to be aligned with the central aperture in an installed position. The passage may be dimensioned to at least partially receive a guide pin insertable through the central aperture and into bone to set a position of the implant.

In a further implementation, the one or more transfer members may be moveable between a first position and a second position.

In a further implementation, each of the one or more transfer members may include a first portion extending radially outward from the guide body and a second portion extending axially from the first portion. The second portion may be configured to abut tissue adjacent the implant.

In a further implementation, the implant may include a baseplate and an augment that may extend from the baseplate relative to an axis. The augment may be dimensioned to contact bone. The baseplate may include a central aperture and a plurality of peripheral apertures circumferentially distributed about the central aperture. Each of the peripheral apertures may be dimensioned to receive a respective fastener to secure the implant to bone. The guide body may include a coupling feature at least partially receivable in the central aperture to secure the transfer guide to the implant. The transfer guide may include an alignment member that may be dimensioned to be insertable into an aperture in the baseplate to limit relative rotation between the transfer guide and the implant.

In a further implementation, the coupling feature may include first threads that may mate with second threads along the central aperture to mechanically attach the transfer guide to the implant.

In a further implementation, the one or more transfer members may be integrally formed with the guide body.

In a further implementation, the guide body may include a passage dimensioned to receive a coupling member. The coupling member may be insertable into the passage and the central aperture to mechanically attach the transfer guide to the implant.

In a further implementation, the coupling member may include a passage. The passage may be dimensioned to receive a guide pin insertable through the central aperture and into bone to set a position of the implant.

In a further implementation, the implant may include a baseplate and an augment that may extend outwardly from the baseplate. The augment may be dimensioned to contact bone. The transfer guide may include an abutment member that may extend outwardly from the guide body. The abutment member may be dimensioned to at least partially follow a periphery of the baseplate.

In a further implementation, each of the one or more transfer members may extend from the guide body to a terminal end portion. The one or more transfer members may include a first transfer member and a second transfer member. The terminal end portion of the first transfer member may have has a geometry that may differ from a geometry of the terminal end portion of the second transfer member.

In a further implementation, each terminal end portion may be dimensioned with respect to a predetermined surface contour of the bone.

In a further implementation, the one or more transfer members may include a transfer body and a transfer arm that may interconnect the guide body and the transfer body. The transfer body may include a contact surface that may be dimensioned with respect to a predetermined surface contour of the bone.

In a further implementation, the implant may include a baseplate and an augment that may extend outwardly from the baseplate. The augment may be dimensioned to contact bone. The guide body may be dimensioned to follow a periphery of the baseplate.

In a further implementation, the one or more transfer members may be integrally formed with the guide body.

In a further implementation, the transfer guide may include a plurality of fixation members that may be dimensioned to interface with a circumferential rim of the baseplate to establish a snap-fit connection.

In a further implementation, the baseplate may include a central aperture and a plurality of peripheral apertures circumferentially distributed about the central aperture. Each of the peripheral apertures may be dimensioned to receive a respective fastener to secure the implant to bone. The transfer guide may include one or more alignment members that may extend inwardly from the guide body. Each of the one or more alignment members may be dimensioned to be insertable into a respective one of the peripheral apertures to limit relative rotation between the transfer guide and the implant.

In a further implementation, the central aperture may be dimensioned to receive a coupling member. The coupling member may include a passage. The passage may be dimensioned to receive a guide pin insertable through the central aperture and into bone to set a position of the implant.

In a further implementation, the coupling member may be spaced apart from the transfer members in an installed position.

In a further implementation, the guide body may be dimensioned to encircle and at least partially receive the periphery of the baseplate.

A method of installing an orthopaedic implant according to an exemplary aspect of this disclosure may include positioning one or more transfer members to contact bone. The one or more transfer members may be coupled to an implant. The method may include positioning the implant relative to the bone based on the positioning of the one or more transfer members.

In a further implementation, the implant may include a baseplate and an augment that may extend outwardly from the baseplate. The step of positioning the implant may occurs such that a surface of the augment may contact the bone.

In a further implementation, the surface of the augment may be dimensioned to substantially follow a surface contour of the bone based on a predetermined surgical plan.

In a further implementation, the baseplate may include a central aperture and a plurality of peripheral apertures circumferentially distributed about the central aperture. Each of the peripheral apertures may be aligned with a respective passage through the augment. The method may include positioning a respective fastener in each respective peripheral aperture and then into the bone to secure the implant.

In a further implementation, the method may include inserting one or more alignment members in a respective one of the peripheral apertures to limit relative rotation between the one or more transfer members and the baseplate.

In a further implementation, the method may include establishing a surgical plan. The surgical plan may be based on a surface profile of the bone. The surgical plan may include at least one dimension that may be associated with the one or more transfer members relative to the surface profile.

In a further implementation, each of the one or more transfer members may include a respective contact surface. The method may include forming the contact surface to substantially follow the surface profile of the bone based on the surgical plan.

In a further implementation, the method may include coupling a transfer guide to the implant. The transfer guide may include a guide body that may interface with the implant. The one or more transfer members may extend from the guide body.

In a further implementation, the method may include the step of positioning one or more transfer members may include moving the one or more transfer members between a first position and a second position relative to the guide body based on the at least dimension.

In a further implementation, the guide body may include a passage. The method may include positioning a guide pin through the passage in the guide body, then through the implant, and then into the bone.

In a further implementation, the method may include integrally forming the one or more transfer members with the guide body based on the at least one dimension subsequent to the step of establishing the surgical plan.

In a further implementation, the transfer guide may include a plurality of fixation members. The step of coupling the transfer guide to the implant may include positioning the plurality of fixation members relative to the implant to establish a snap-fit connection.

In a further implementation, the method may include integrally forming the one or more transfer members with the implant.

In a further implementation, each of the one or more transfer members may be coupled to the implant at a respective breakable connection. The method may include severing the breakable connection in response to a predetermined quantity of force applied to the respective transfer member.

In a further implementation, the bone may be a portion of a glenoid.

FIG. 1 illustrates an exemplary planning system 20 that may be utilized for planning surgical procedures. The system 20 may be used for planning orthopaedic procedures, including pre-operatively, intra-operatively and/or post-operatively to create, edit, execute and/or review surgical plans. The system 20 may be utilized for various orthopaedic and other surgical procedures, such as an arthroplasty to repair a joint. The system 20 may be utilized in the placement of an implant, such as an implant incorporated into a shoulder prosthesis, for example. Although the planning systems and methods disclosed herein primarily refer to repair of a glenoid or humerus during an anatomic or reverse shoulder reconstruction, it should be understood that the planning system 20 may be utilized in the repair of other locations of the patient and other surgical procedures including repair of other bones and joints such as a wrist, hand, hip, knee or ankle and repair of fractures and other deformities.

The system 20 may include a host computer 21 and one or more client computers 22. The host computer 21 may be configured to execute one or more software programs. In some implementations, the host computer 21 may be more than one computer jointly configured to process software instructions serially or in parallel.

The host computer 21 may be in communication with one or more networks such as a network 23 comprised of one or more computing devices. The network 23 may be a private local area network (LAN), a private wide area network (WAN), the Internet, or a mesh network, for example.

The host computer 21 and each client computer 22 may include one or more of a computer processor, memory, storage means, network device and input and/or output devices and/or interfaces. The input devices may include a keyboard, mouse, etc. The output device may include a monitor, speakers, printers, etc. The memory may, for example, include UVPROM, EEPROM, FLASH, RAM, ROM, DVD, CD, a hard drive, or other computer readable medium which may store data and/or other information relating to the planning and implementation techniques disclosed herein. The host computer 21 and each client computer 22 may be a desktop computer, laptop computer, smart phone, tablet, or any other computing device. The interface may facilitate communication with the other systems and/or components of the network 23.

Each client computer 22 may be configured to communicate with the host computer 21 directly via a direct client interface 24 or over the network 23. In another implementation, the client computers 22 are configured to communicate with each other directly via a peer-to-peer interface 25.

The system 20 may include, or may be coupled to, one or more imaging devices 26. Each client computer 22 may be coupled to one or more imaging devices 26, for example. Each imaging device 26 may be configured to capture or acquire one or more images 30 of patient anatomy residing within a scan field (e.g., window) of the imaging device 26. The imaging device 26 may be configured to capture or acquire two dimensional (2D) and/or three dimensional (3D) greyscale and/or color images 30. Various imaging devices 26 may be utilized, such as an X-ray machine, computerized tomography (CT) machine or magnetic resonance imaging (MRI) machine that obtains one or more images of a patient.

The client computers 22 may be configured to execute one or more software programs, such as a various surgical tools. Each client computer 22 may be operable to access and locally and/or remotely execute a planning environment 27. The planning environment 27 may be a standalone software package or may be incorporated into another surgical tool. The planning environment 27 may be configured to communicate with the host computer 21 either over the network 23 or directly through the direct client interface 24.

The planning environment 27 may be configured to interact with one or more of the imaging devices 26 to capture or acquire images 30 of patient anatomy. The planning environment 27 may provide a display or visualization of one or more images 30, bone models 31, implant models 32 and/or transfer models 48 via one or more graphical user interfaces (GUI). Each image 30, bone model 31, implant model 32, transfer model 48 and other data and information may be stored in one or more files or records according to a specified data structure.

The system 20 may include at least one storage system 28, which may be operable to store or otherwise provide data to other computing devices. The storage system 28 may be a storage area network device (SAN) configured to communicate with the host computer 21 and/or the client computers 22 over the network 23, for example. In implementations, the storage system 28 may be incorporated within or directly coupled to the host computer 21 and/or client computers 22. The storage system 28 may be configured to store one or more of computer software instructions, data, database files, configuration information, etc.

In some implementations, the system 20 may be a client-server architecture configured to execute computer software on the host computer 21, which may be accessible by the client computers 22 using either a thin client application or a web browser executing on the client computers 22. The host computer 21 may load the computer software instructions from local storage, or from the storage system 28, into memory and may execute the computer software using the one or more computer processors.

The system 20 may include one or more databases 29. The databases 29 may be stored at a central location, such as the storage system 28. In another implementation, one or more databases 29 may be stored at the host computer 21 and/or may be a distributed database provided by one or more of the client computers 22. Each database 29 may be a relational database configured to associate one or more images 30, bone models 31, implant models 32 and/or transfer models 48 to each other and/or a surgical plan 33. Each surgical plan 33 may be associated with the anatomy of a respective patient. Each image 30, bone model 31, implant model 32, transfer model 48 and surgical plan 33 may be assigned a unique identifier or database entry. The database 29 may be configured to store data and other information corresponding to the images 30, bone models 31, implant models 32, transfer models 48 and surgical plans 33 in one or more database records or entries, and/or may be configured to link or otherwise associate one or more files corresponding to each respective image 30, bone model 31, implant model 32, transfer model 48 and surgical plan 33. Images 30, bone models 31, implant models 32, transfer models 48 and associated surgical plans 33 stored in the database(s) 29 may correspond to respective patient anatomies from prior surgical cases, and may be arranged into one or more predefined categories such as sex, age, ethnicity, defect category, procedure type, surgeon, facility or organization, etc.

Each image 30 and bone model 31 may include data and other information obtained from one or more medical devices or tools, such as the imaging devices 26. The bone model 31 may include coordinate information relating to an anatomy of the patient obtained or derived from image(s) 30 captured or otherwise obtained by the imaging device(s) 26. Each implant model 32, transfer model 48 may include coordinate information associated with a predefined design or a design established or modified by the planning environment 27. The planning environment 27 may incorporate and/or interface with one or more modeling packages, such as a computer aided design (CAD) package, to render the models 31, 32, 48 as two-dimensional (2D) and/or three-dimensional (3D) volumes or constructs, which may overlay one or more of the images 30 in a display screen of a GUI.

The implant models 32 may correspond to implants and components of various shapes and sizes. Each implant may include one or more components that may be situated at a surgical site including screws, anchors and/or grafts. Each implant model 32 may correspond to a single component or may include two or more components that may be configured to establish an assembly. Each implant and associated component(s) may be formed of various materials, including metallic and/or non-metallic materials. Each bone model 31, implant model 32 and transfer model 48 may correspond to 2D and/or 3D geometry, and may be utilized to generate a wireframe, mesh and/or solid construct in a display.

Each surgical plan 33 may be associated with one or more of the images 30, bone models 31, implant models 32 and/or transfer models 48. The surgical plan 33 may include various parameters associated with the images 30, bone models 31, implant models 32 and/or transfer models 48. For example, the surgical plan 33 may include parameters relating to bone density and bone quality associated with patient anatomy captured in the image(s) 30. The surgical plan 33 may include parameters including spatial information relating to relative positioning and coordinate information of the selected bone model(s) 30, implant model(s) 32 and/or transfer model(s) 48.

The surgical plan 33 may include one or more revisions to a bone model 31 and information relating to a position of an implant model 32 and/or transfer model 48 relative to the original and/or revised bone model 31. The surgical plan 33 may include coordinate information relating to the revised bone model 31 and a relative position of the implant model 32 and/or transfer model 48 in predefined data structure(s). The planning environment 27 may be configured to make one or more revisions to a transfer model 48 automatically or in response to user interaction with the user interface. Revisions to each bone model 31, implant model 32, transfer model 48 and/or surgical plan 33 may be stored in the database 29 automatically and/or in response to user interaction with the system 20.

One or more surgeons and other users may be provided with a planning environment 27 via the client computers 22 and may simultaneously access each image 30, bone model 31, implant model 32, transfer model 48 and surgical plan 33 stored in the database(s) 29. Each user may interact with the planning environment 27 to create, view and/or modify various aspects of the surgical plan 33. Each client computer 22 may be configured to store local instances of the images 30, bone models 31, implant models 32, transfer models 48 and/or surgical plans 33, which may be synchronized in real-time or periodically with the database(s) 29. The planning environment 27 may be a standalone software package executed on a client computer 22 or may be provided as one or more services executed on the host computer 21, for example.

Figure 2:
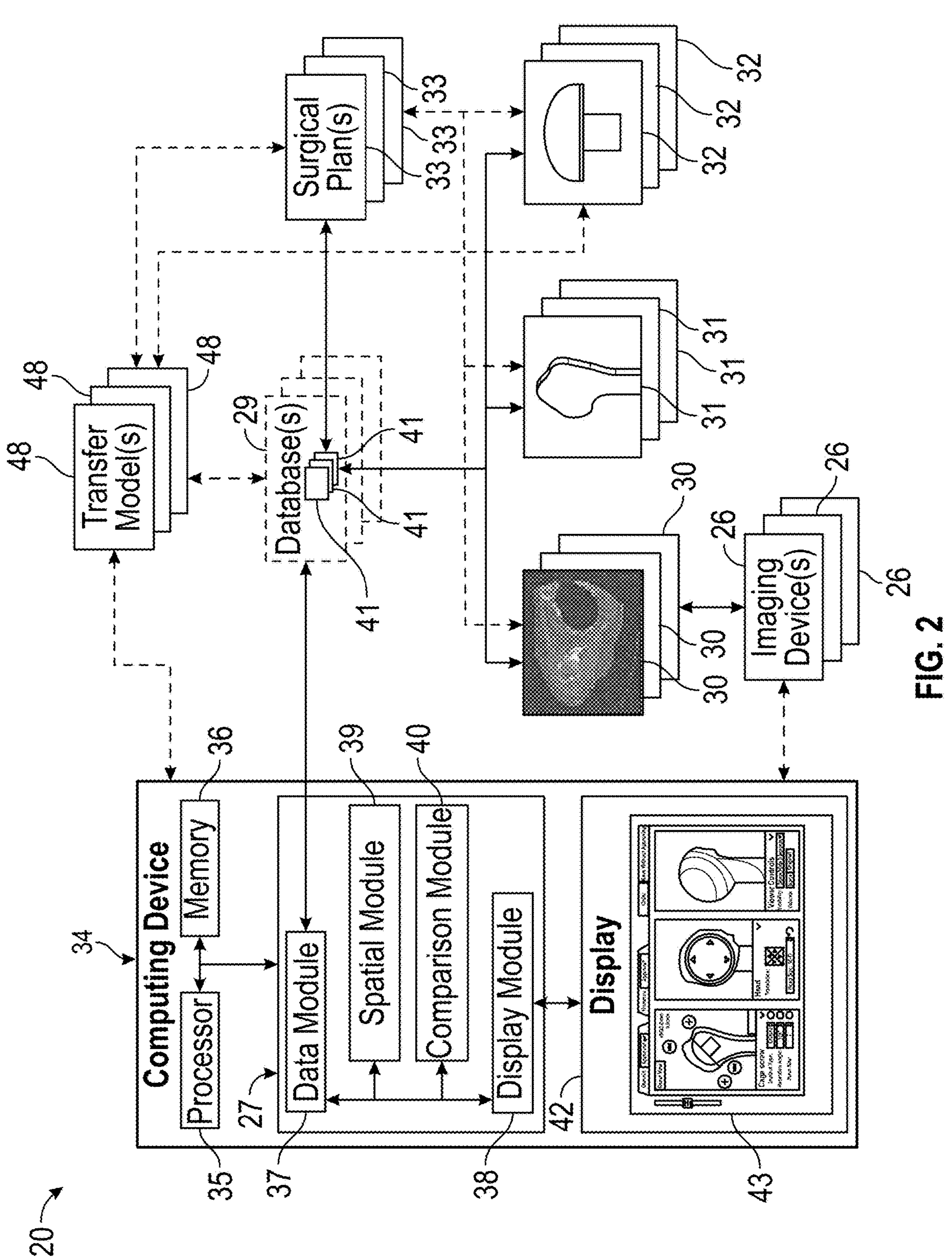
FIG. 2 illustrates aspects of the exemplary planning system of FIG. 1.

Referring to FIG. 2, with continuing reference to FIG. 1, the system 20 may include a computing device 34 including at least one processor 35 coupled to memory 36. The computing device 34 may include any of the computing devices disclosed herein, including the host computer 21 and/or client computer 22. The processor 35 may be configured to execute a planning environment 27 for creating, editing, executing and/or reviewing one or more surgical plans 33 and any associated bone models 31, implant models 32 and transfer models 48 during pre-operative, intra-operative and/or post-operative phases of a surgery.

The planning environment 27 may include at least a data module 37, a display module 38, a spatial module 39 and a comparison module 40. Although four modules are shown, it should be understood that fewer or more than four modules may be utilized and/or one or more of the modules may be combined to provide the disclosed functionality.

The data module 37 may be configured to access, retrieve and/or store data and other information in the database(s) 29 corresponding to one or more images 30 of patient anatomy, bone model(s) 31, implant model(s) 32, transfer model(s) 48 and/or surgical plan(s) 33. The data and other information may be stored in one or more databases 29 as one or more records or entries 41. In some implementations, the data and other information may be stored in one or more files that are accessible by referencing one or more objects or memory locations referenced by the records 41.

The memory 36 may be configured to access, load, edit and/or store instances of one or more images 30, bone models 31, implant models 32, transfer models 48 and/or surgical plans 33 in response to one or more commands from the data module 37. The data module 37 may be configured to cause the memory 36 to store a local instance of the image(s) 30, bone model(s) 31, implant model(s) 32, transfer model(s) 48 and/or surgical plan(s) 33, which may be synchronized with the records 41 in the database(s) 29.

The data module 37 may be configured to receive data and other information corresponding to at least one or more images 30 of patient anatomy from various sources such as the imaging device(s) 26. The data module 37 may be configured to command the imaging device 26 to capture or acquire the images 30 automatically or in response to user interaction.

The display module 38 may be configured to display data and other information relating to one or more surgical plans 33 in at least one graphical user interface (GUI) 43, including one or more of the images 30, bone models 31, implant models 32 and/or transfer models 48. The computing device 34 may incorporate or be coupled to a display device 42. The display module 38 may be configured to cause the display device 42 to display information in the user interface 43. A surgeon or other user may interact with the user interface 43 via the planning environment 27 to view one or more images 30 of patient anatomy 46 and/or any associated bone models 31, implant models 32 and transfer models 48. The surgeon or other user may interact with the user interface 43 via the planning environment 27 to create, edit, execute and/or review one or more surgical plans 33.

Figure 3A:
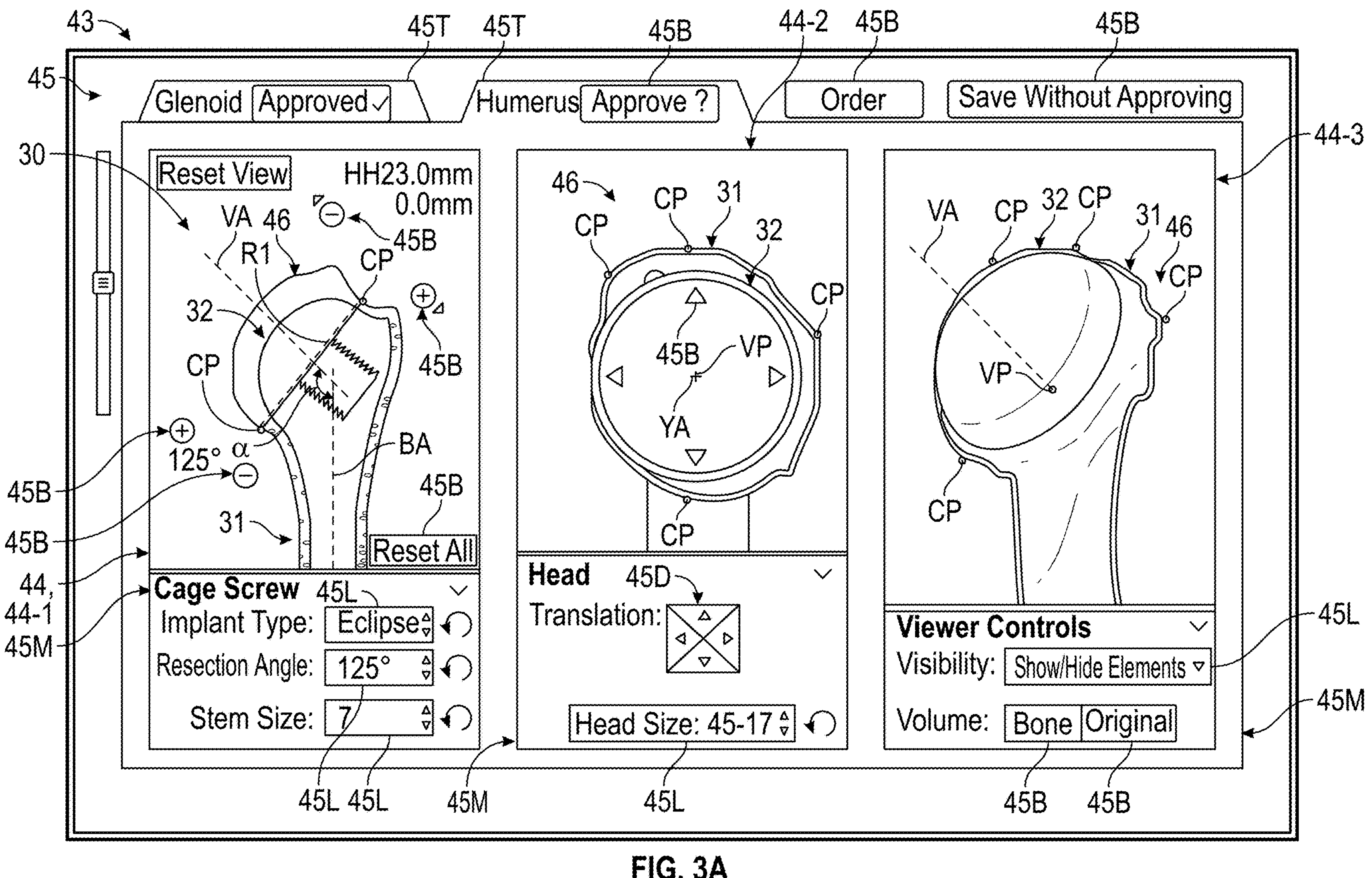
FIG. 3A illustrates an exemplary user interface of the planning system of FIG. 2.
Figure 3B:
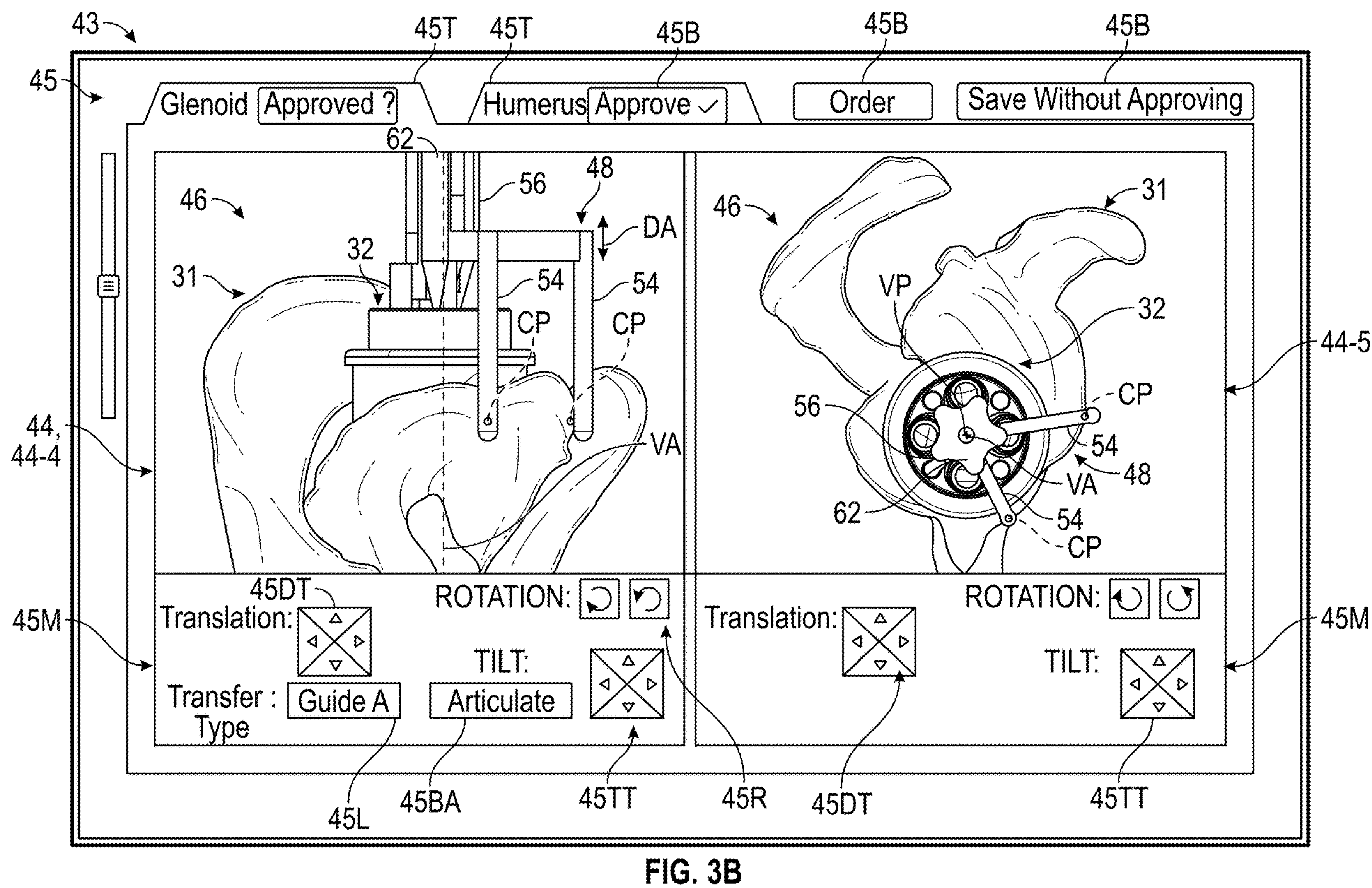
FIG. 3B illustrates another exemplary user interface of the planning system of FIG. 2.

Referring to FIG. 3A-3B, with continuing reference to FIG. 2, the user interface 43 may include one or more display windows 44 and one or more objects 45. The display windows 44 may include first, second and third display windows 44-1, 44-2, 44-3, as illustrated in FIG. 3A, and may include fourth and fifth display windows 44-4, 44-5 as illustrated in FIG. 3B. Although five display windows 44 are shown, it should be understood that fewer or more than five display windows 44 may be utilized in accordance with the teachings disclosed herein.

A surgeon or user may interact with the user interface 43 including the objects 45 and/or display windows 44 to retrieve, view, edit, store, etc., various aspects of a surgical plan 33, such as the selected image(s) 30, bone model(s) 31, implant model(s) 32 and/or transfer model(s) 48. The objects 45 may include graphics such as menus, tabs and buttons accessible by user interaction, such as tabs 45T, buttons 45B, drop-down lists 45L, and directional indicator 45D. The objects 45 may be organized in one or more menu items 45M associated with the respective display windows 44. Geometric objects, including selected image(s) 30, bone model(s) 31, implant model(s) 32, transfer model(s) 48 and/or other information relating to the surgical plan 33, may be displayed in one or more of the display windows 44 as illustrated in FIGS. 3A-3B. Each transfer model 48 may include one or more transfer members 54, which may be associated with a transfer guide 56 as illustrated in windows 44-4, 44-5.

The surgeon may interact with the objects 45 to specify various aspects of a surgical plan 33. For example, the surgeon may select one of the tabs 45T to view or specify aspects of the surgical plan 33 for one portion of a joint, such as a glenoid (see, e.g., FIG. 3B), and may select another one of the tabs 45T to view or specify aspects of the surgical plan 33 for another portion of the joint, such as a humerus (see, e.g., FIG. 3A).

The surgeon may interact with the menu items 45M to select and specify various aspects of the bone models 31, implant models 32 and/or transfer models 48 from the database 29. For example, the display module 38 may be configured to display one or more bone models 31 together with the respective image(s) 30 of the patient anatomy 46 and implant models 32 selected in response to user interaction with the user interface 43, as illustrated in FIG. 3A. The user may interact with the drop-down lists 45L associated with the first display window 44-1 to specify implant type, resection angle and implant size. The resection angle menu item may be associated with a resection plane R1 (shown in dashed lines in window 44-1 for illustrative purposes).

The user may interact with buttons 45B to change (e.g., increase or decrease) the resection angle. The user may interact with buttons 45B adjacent the selected implant model 32 to change (e.g., increase or decrease) a size of a component of the selected implant model 32. The buttons 45B may be overlaid onto or may be situated adjacent to the display windows 44. The user may interact with the directional indicator 45D to move a portion of the selected implant model 32 in different directions (e.g., up, down, left, right) in the second display window 44-2. The surgeon may drag or otherwise move the selected implant model 32 to a desired position in the second display window 44-2 utilizing a mouse, for example. The surgeon may interact with one of the drop-down lists 45L to specify a type and/or size of a component of the selected implant model 32.

The display module 38 may be configured to superimpose one or more of the bone models 31, and implant models 32 over one or more of the images 30, as illustrated by window 44-1. The implant model 32 may include one or more components that establish an assembly. At least a portion of the implant model 32 may be configured to be at least partially received in a volume of a selected one of the bone models 31. The implant model 32 may have an articulation surface dimensioned to mate with an articular surface of an opposed bone or implant.

The display windows 44 may be configured to display the images 30, bone models 31, implant models 32 and/or transfer model(s) 48 at various orientations. The display module 38 may be configured to display two dimensional (2D) representation(s) of the selected bone model(s) 31, implant model(s) 32 and/or transfer model(s) 48 in the first and/or second display windows 44-1, 44-2, and may be configured to display 3D representation(s) of the selected bone model 31, implant model 32 and/or transfer model(s) 48 in the third display window 44-3, for example. The surgeon may interact with the user interface 43 to move the selected bone model 31, selected implant model 32 and/or selected transfer model 48 in 2D space (e.g., up, down, left, right) and/or 3D space. In other implementations, the display module 38 may be configured to display a 2D representation of the selected bone model(s) 31, selected implant model(s) 32 in the third display window 44-3.

The display module 38 may be configured such that the selected image(s) 30, bone model(s) 31, implant model(s) 32 and/or transfer model(s) 48 may be selectively displayed and hidden (e.g., toggled) in one or more of the display windows 44 in response to user interaction with the user interface 43, which may provide the surgeon with enhanced flexibility in reviewing aspects of the surgical plan 33. For example, the surgeon may interact with the drop-down lists 45L to selectively display and hide components of the selected implant model 32 in the third display window 44-3.

The selected bone model 31 may correspond to a bone associated with a joint, including any of the exemplary joints disclosed herein, such as a humerus as illustrated in FIG. 3A. The display module 38 may be configured to display a sectional view of the selected bone model 31 and selected implant model 32 in the first viewing window 44-1, for example. The sectional view of the bone model(s) 31 may be presented or displayed together with the associated image(s) 30 of the patient anatomy 46.

The spatial module 39 may be configured to establish the resection plane R1 along the selected bone model 31. A volume of the selected implant model 32 may be at least partially received in a volume of the selected bone model 31 along the resection plane R1. The resection plane R1 may be defined by a resection angle.

The spatial module 39 may be configured to cause the display module 38 to display an excised portion of the selected bone model 31 to be displayed in the first display window 44-1 in a different manner than a remainder of the bone model 31 on an opposed side of the resection plane R1. For example, the excised portion of the bone model 31 may be hidden from display in the first display window 44-1 such that the respective portion of the image 30 of the patient anatomy 46 is shown, as illustrated in FIG. 3A. In other implementations, the excised portion of the selected bone model 31 may be displayed in a relatively darker shade. The spatial module 39 may determine the excised portion by comparing coordinates of the bone model 31 with respect to a position of the resection plane R1, for example. The user may interact with one or more buttons 45B to toggle between a volume of previous and revised (e.g., resected) states of the selected bone model 31.

The planning environment 27 may be configured such that changes in one of the display windows 44 are synchronized with each of the other windows 44. The changes may be synchronized between the display windows 44 automatically and/or manually in response to user interaction.

The surgeon may utilize various instrumentation and devices to implement each surgical plan 33, including preparing the surgical site and securing one or more implants to bone or other tissue to restore functionality to the respective joint. Each of the transfer models 48 may be associated with a respective instrument or device (e.g., transfer guide) or a respective implant model 32.

The surgical plan 33 may be associated with one or more positioning objects such as a guide pin (e.g., guide wire or Kirschner wire) dimensioned to be secured in tissue to position and orient the various instrumentation, devices and/or implants. The display module 38 may be configured to display a virtual position VP and virtual axis VA in one or more of the display windows 44. The virtual position VP may be associated with a specified position of the positioning object relative to the patient anatomy 46. The virtual axis VA may extend through the virtual position VP and may be associated with a specified orientation of the positioning object relative to the patient anatomy 46. The spatial module 39 may be configured to set the virtual position VP and/or virtual axis VA in response to placement of a respective implant model 32 relative to the bone model 31 and associated patient anatomy 46. The virtual position VP and/or virtual axis VA may be set and/or adjusted automatically based on a position and orientation of the selected implant model 32 relative to the selected bone model 31 and/or in response to user interaction with the user interface 43.

The spatial module 39 may be configured to determine one or more contact points CP associated with the patient anatomy 46. The contact points CP may be associated with one or more landmarks or other surface features along the bone model 31 and/or other portions of the patient anatomy 46. Each contact point CP may be established along an articular surface or non-articular surface of a joint. The spatial module 39 may be configured to set the contact points CP based on the virtual position VP, virtual axis VA and/or position and orientation of the respective implant model 32 relative to the patient anatomy 46. The spatial module 39 may be configured to cause the display module 38 to display the contact points CP in one or more of the display windows 44, as illustrated in FIGS. 3A-3B. In implementations, the contact points CP may be set and/or adjusted automatically based on a position of the implant model 32 and/or in response to user interaction with the user interface 43. The virtual position VP, virtual axis VA and/or contact points CP may be stored in one or more records 41 in the database 29 and may be associated with the respective surgical plan 33.

The comparison module 40 may be configured to generate or set one or more parameters associated with implementing the surgical plan 33. The parameters may include one or more settings or dimensions associated with the respective transfer models 48. The parameters may be based on the virtual position VP, virtual axis VA and/or contact points CP. The comparison module 40 may be configured to determine one or more settings or dimensions associated with the respective transfer models 48 relative to the patient anatomy 46, bone model(s) 31, implant model(s) 46, virtual position VP, virtual axis VA and/or contact points CP. The dimensions and settings may be utilized to form a physical instance of each respective transfer model 48. The settings may be utilized to specify a position and orientation of each respective transfer model 48 relative to the implant model 32 and/or bone model 31. The settings may be utilized to configure one or more transfer members (e.g., objects) and related instrumentation or devices associated with the transfer model 48. The comparison module 40 may be configured to generate the settings and/or dimensions such that the transfer model 48 contacts one or more predetermined positions at or along the bone model 31 or patient anatomy 46 in an installed position when coupled to the respective implant model 32. The predetermined positions may include one or more of the contact points CP. The settings and dimensions may be communicated utilizing various techniques, including one or more graphics in the user interface 43 or output files. The settings and/or dimensions may be stored in one or more records 41 in the database 29 associated with the transfer models 48.

The user may interact with a list 45L associated with the display window 44-4 to select a transfer model 48 from the database 29. The display model 38 may be configured to display the selected transfer model 48 in the windows 44-4 and/or 44-5 at various positions and orientations. The spatial module 39 may be configured to set an initial position of the selected transfer model 48 according to the virtual position VP, virtual axis VA and/or contact points CP.

The user may interact with the user interface 43 to set or adjust a position and/or orientation of the selected transfer model 48. The user may interact with directional indicators 45DT to move the selected transfer model 48 and/or virtual position VP in different directions (e.g., up, down, left, right) in the display windows 44-4, 45. The surgeon may drag or otherwise move the selected transfer model 48 and/or virtual position VP to a desired position in the windows 44-4, 44-5 utilizing a mouse, for example. The user may interact with rotational indicators 45R to adjust a position and/or orientation of the transfer model 48 about the virtual axis VA relative to the selected bone model 31 and/or implant model 32. The user may interact with tilt indicators 45TT to adjust an orientation of the selected transfer model 48 and associated virtual axis VA at the virtual position VP relative to the selected bone model 31 and/or implant model 32. The user may interact with an articulation button 45BA and/or directional indicator DA (e.g., window 44-4) to cause the transfer members 54 to articulate or otherwise move to relative to a guide body 62 of the transfer guide 56. The transfer members 54 may be articulated or otherwise moved independently or synchronously, which may occur manually in response to user interaction and/or automatically in response to situating the transfer members 54 relative to the bone model 31 and/or implant model 32. Articulation or movement of the transfer members 54 may occur such that the articulation members 54 contact a surface of the bone model 31. Movement of the transfer members 54 may cause an adjustment to the respective contact points CP. In some implementations, a position of the transfer members 54 is fixed relative to the transfer guide 56 and/or implant 52.

Various transfer members may be utilized with the planning environment 27 to implement the surgical plan(s) 33, including any of the transfer members disclosed herein. Each transfer member may be associated with a respective transfer model 48. The disclosed transfer members may be incorporated into transfer guides, implants and/or assemblies to set a position and orientation of the respective implant prior to fixing or otherwise securing the implant at a surgical site.

Figures 4, 5:
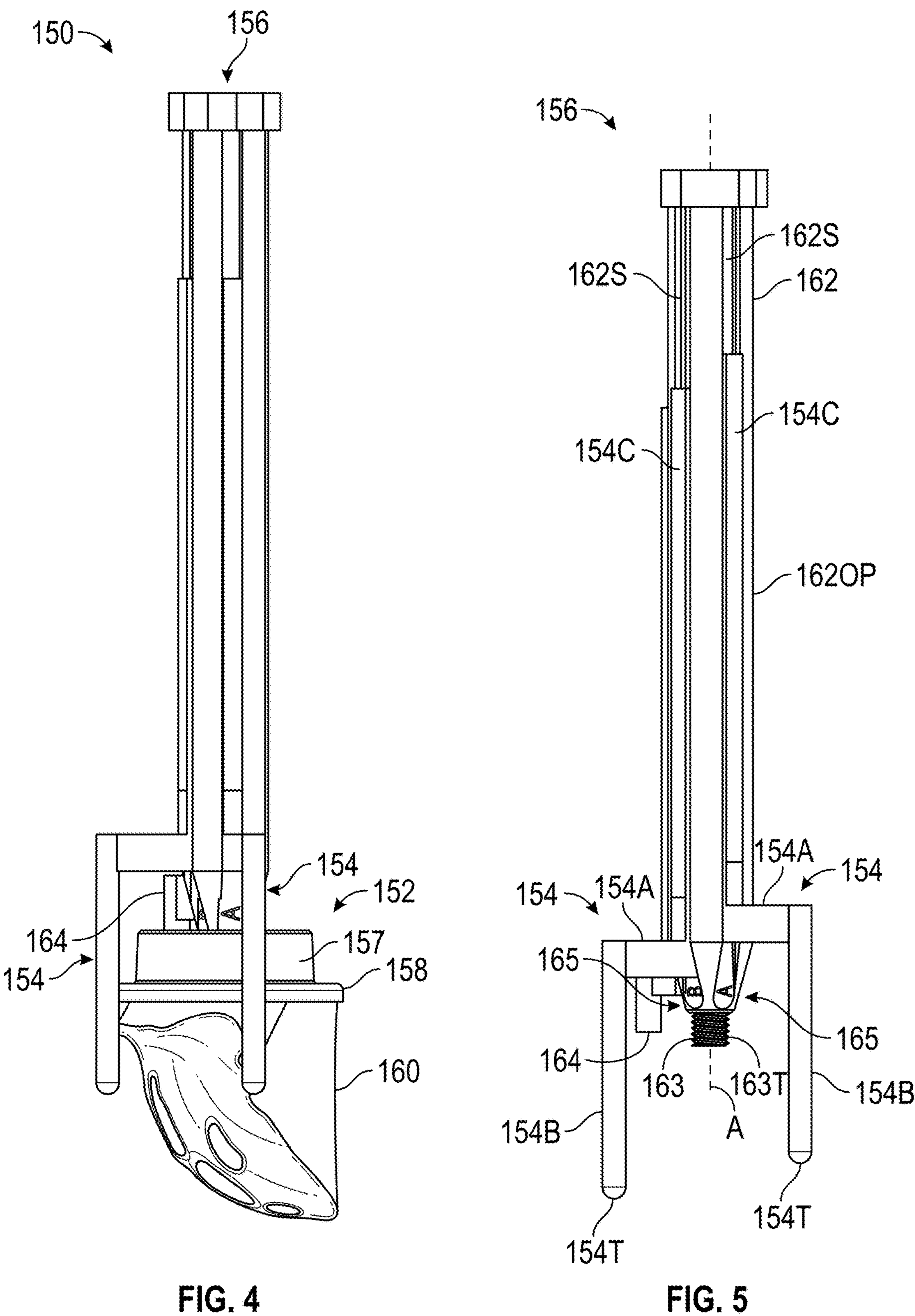
FIG. 4 illustrates an exemplary orthopaedic assembly including an implant, transfer guide and transfer members.
FIG. 5 illustrates an isolated view of the transfer guide of FIG. 4.

FIG. 4 illustrates an exemplary assembly 150 for an orthopaedic procedure. The assembly 150 may be utilized to restore functionality to shoulders and other joints, such as the repair of a glenoid or humerus during an anatomic or reverse shoulder reconstruction. The assembly 150 may be utilized in the repair of other locations of the patient and other surgical procedures including repair of other joints such as a wrist, hand, hip, knee or ankle and repair of fractures and other deformities. In this disclosure, like reference numerals designate like elements where appropriate and reference numerals with the addition of one-hundred or multiples thereof designate modified elements that are understood to incorporate the same features and benefits of the corresponding original elements.

The assembly 150 may include an orthopaedic implant 152 and one or more transfer members (e.g., objects) 154. The implant 152 and each transfer member 154 may be configured to abut or contact bone B or other tissue (see, e.g., FIGS. 10-12). The assembly 150 may include a transfer guide 156 configured to interface with the implant 152. The transfer guide 156 may incorporate one or more of the transfer members 154 as illustrated in FIGS. 4-7. Although two transfer members 154 are shown, it should be understood that fewer or more than two transfer members 154 may be utilized in accordance with the teachings disclosed herein.

Figure 10:
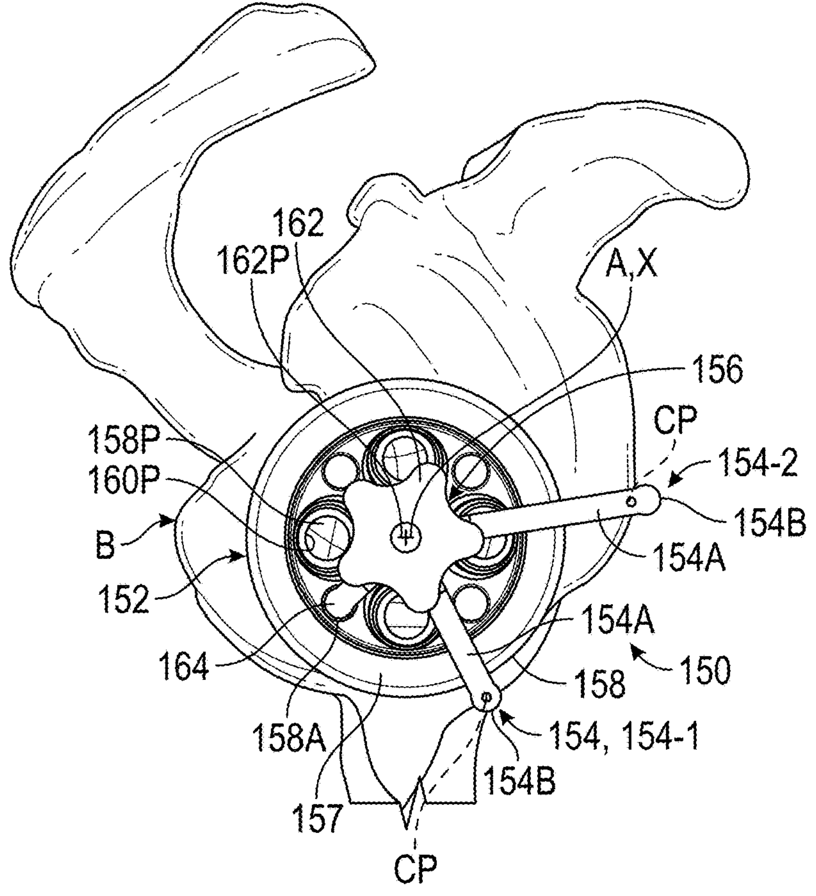
FIG. 10 illustrates an axial view of the assembly of FIG. 4 positioned at a surgical site.
Figures 11, 12:
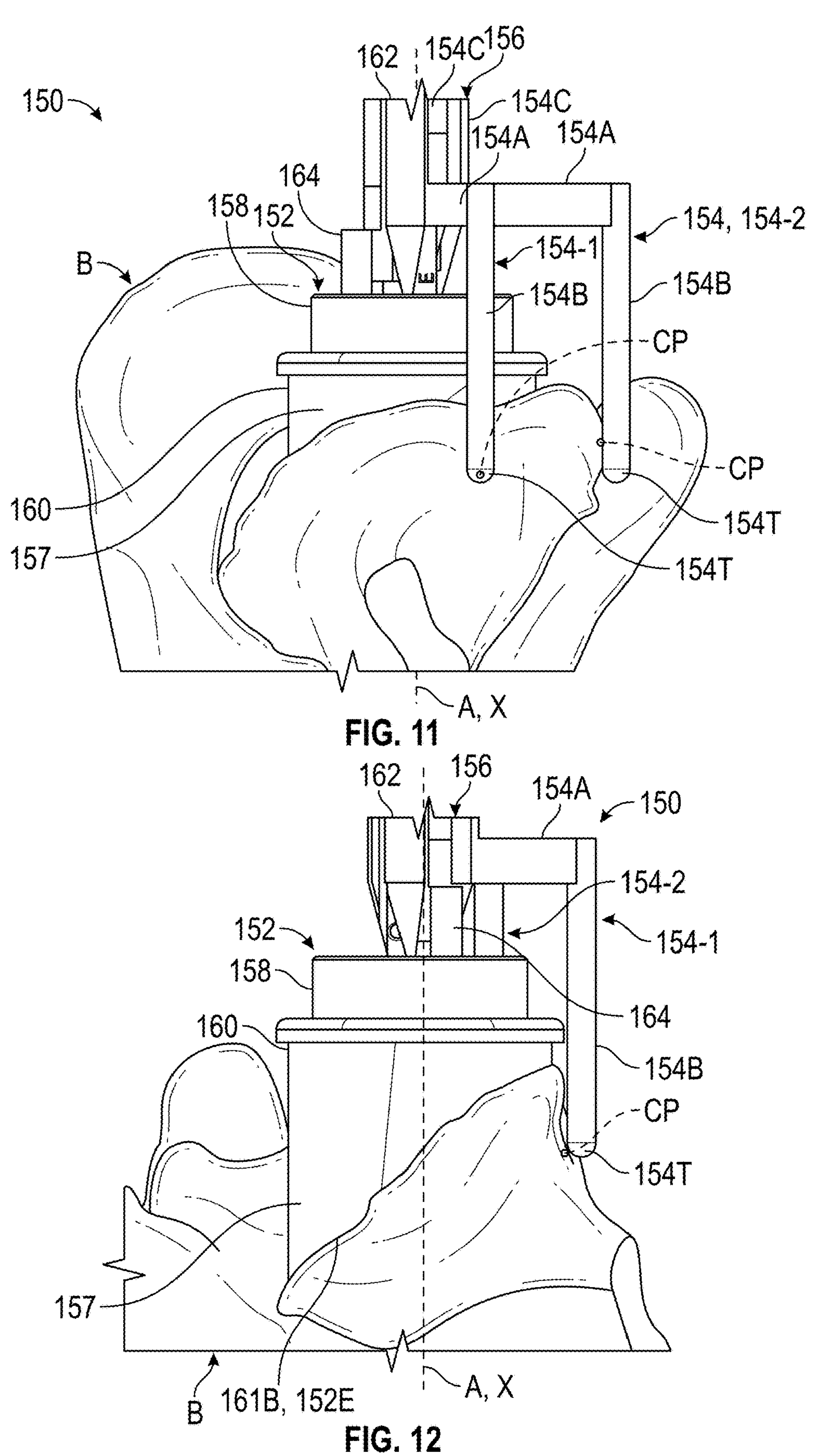
FIG. 11 illustrates a side view of the assembly of FIG. 10.
FIG. 12 illustrates another side view of the assembly of FIG. 10.

A surgeon or user may position and orient the implant 152 based on a position of the transfer members 154 and/or transfer guide 156 relative to tissue such as bone B (see, e.g., FIGS. 10-12). The bone B may be a portion of a glenoid or another bone associated with a joint of a patient.

Each transfer member 154 may be associated with a respective transfer model 48 (FIG. 2). The transfer model 48 may be associated with each transfer member 154 of the respective transfer guide 156 and/or implant 152. The implant 152 may be associated with a respective implant model 32 (FIG. 2). The bone B may be associated with a respective bone model 31 (FIG. 2).

Figure 8:
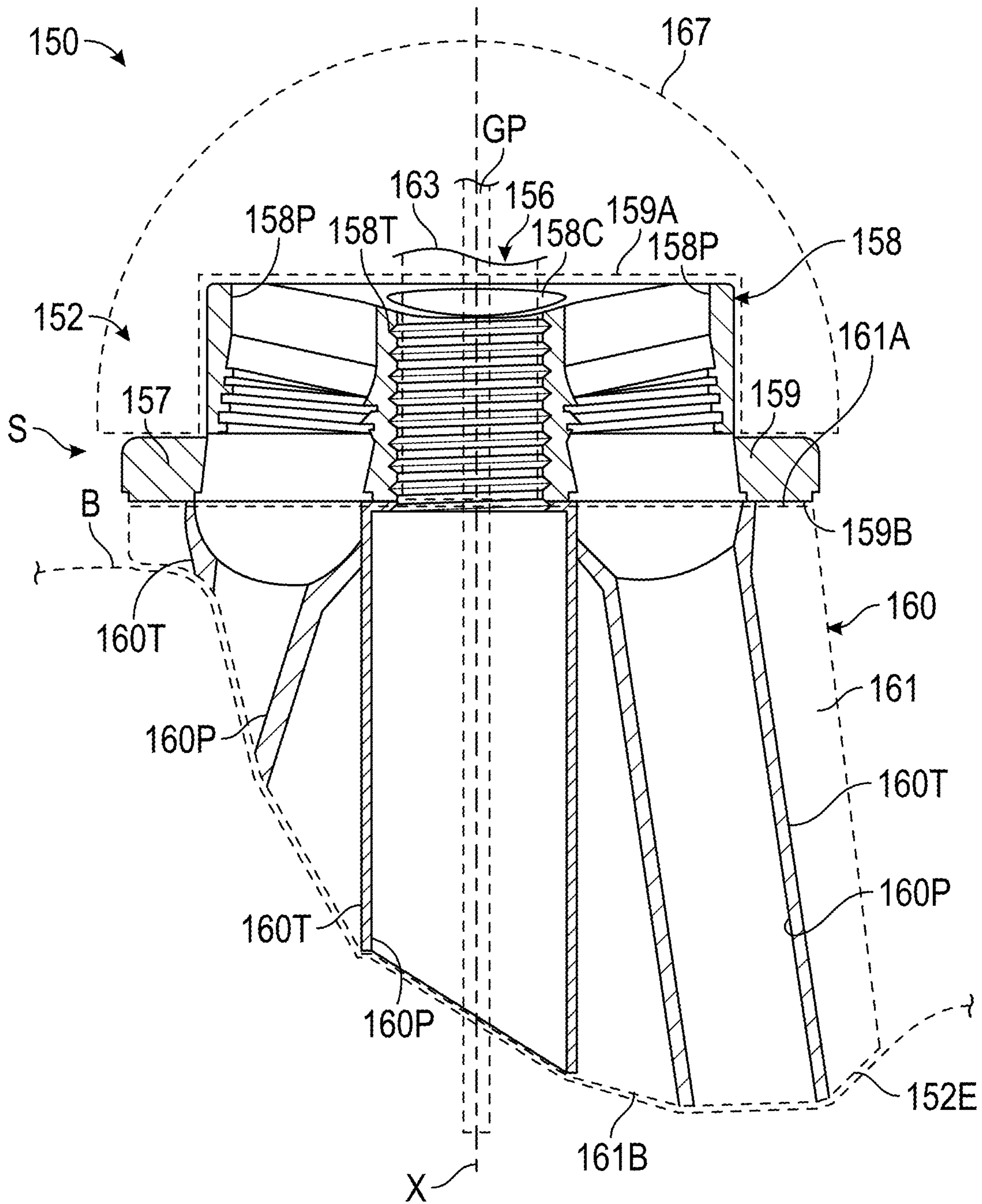
FIG. 8 illustrates a sectional view of portions of the assembly of FIG. 4.

The implant 152 may include a main body 157 dimensioned to abut against bone B at a surgical site S (see, e.g., FIGS. 8 and 11-12). The main body 157 may be dimensioned to receive one or more fasteners F (see, e.g., FIGS. 13D-13E). Each of the fasteners F may be dimensioned to be at least partially received in the bone B to secure the implant 152 at the surgical site S. Various fasteners F may be utilized with the implant 152, such as nails and compression screws.

The implant 152 may include a baseplate 158 and augment 160 that establish the main body 157. The baseplate 158 and augment 160 may be integrally formed to establish a monolithic or unitary component or may be separate and distinct components that are fixedly attached or otherwise secured to one another. The augment 160 may be formed along the baseplate 158 utilizing various techniques, such as printing the augment 160 on the baseplate 158 utilizing a printing device.

Referring to FIG. 8, with continuing reference to FIGS. 4-7, the baseplate 158 may include a plate body 159 extending along a longitudinal (e.g., central) axis X between a first (e.g., front) face 159A and a second (e.g., rear) face 159B generally opposed to the first face 159A. A perimeter of the plate body 159 may have a substantially circular or elliptical geometry. A substantially circular geometry may reduce a reaming width and complexity of preparing a surgical site to accept the implant 152.

The baseplate 158 may include a central aperture 158C and a plurality of peripheral apertures 158P. The peripheral apertures 158P may be circumferentially distributed about the central aperture 158C relative to the longitudinal axis X (see, e.g., FIGS. 13C-13F).

The augment 160 may extend outwardly from the baseplate 158 relative to the axis X. A perimeter of the augment 160 shown in dashed lines in FIG. 8 for illustrative purposes. The augment 160 may include an augment body 161 dimensioned to contact bone B. The augment body 161 may extend along the longitudinal axis X between a first (e.g., front) face 161A and a second (e.g., rear) face 161B generally opposed to the first face 161A. The front faces 159A, 161A may generally correspond to a lateral side of a patient, and the rear faces 159B, 161B may generally correspond to a medial side of the patient when implanted in a surgical site. The front face 161A of the augment 160 may extend along the rear face 159B of the baseplate 158.

The augment body 161 may extend outwardly from the rear face 159B of the baseplate 158 to establish an external surface 152E of the implant 152. The rear face 161B and/or other portions of the augment 160 establishing the external surface 152E of the implant 152 may be dimensioned to approximate a geometry of a bone defect or may have one or more surfaces having a patient-specific geometry dimensioned to substantially conform or follow a surface contour of the bone associated with a respective patient, such as a surface contour established along an articular surface of the respective bone. The rear face 159B may be dimensioned to substantially follow a surface contour of the bone B, as illustrated in FIGS. 8 and 12.

The augment 160 may establish one or more passages 160P through the augment body 161. The augment 160 may include one or more tubular members 160T extending between the rear face 159B of the baseplate 158 and an external surface 152E of the implant 152 established by the augment 160. Each tubular member 160T may establish a respective one of the passages 160P. Portions of the augment body 161 surrounding the tubular members 160T may be substantially solid or may be porous. Each of the peripheral apertures 158P and central aperture 158C may be aligned with a respective one of the passages 160P. The central aperture 158C and/or each of the peripheral apertures 158P may be dimensioned to receive a respective fastener F to secure the implant 152 to bone B along the surgical site (see FIG. 13F).

Referring to FIGS. 6-7 and 9-12, with continuing reference to FIGS. 5 and 8, the transfer guide 156 may include a guide body 162 configured to be coupled to the implant 152, as illustrated in FIGS. 9-12. The transfer guide 156 may include one or more transfer members 154 extending from the guide body 162. One or more transfer members 154 may be positioned relative to the guide body 162 based on a predetermined surgical plan. The predetermined surgical plan may be established by the planning system 20 and utilizing any of the techniques disclosed herein.

Figure 7:
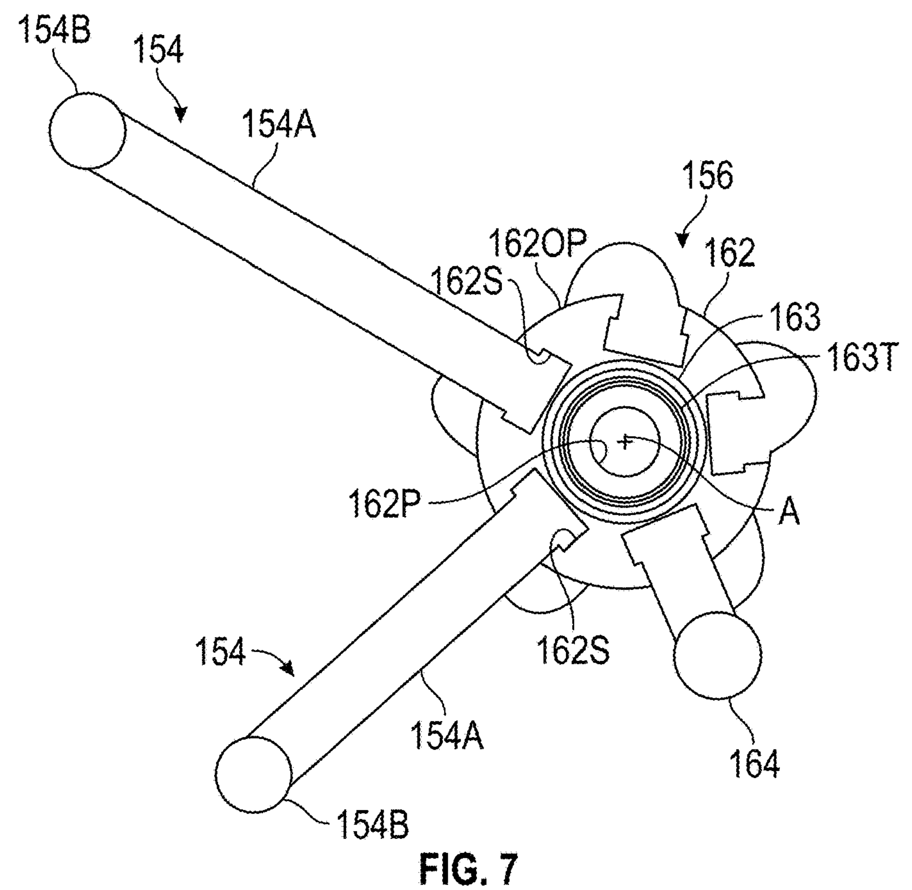
FIG. 7 illustrates an axial view of the transfer guide of FIG. 5.

The guide body 162 may include a passage 162P extending along a longitudinal (e.g., central) axis A of the transfer guide 156, as illustrated in FIGS. 7 and 10. The passage 162P may be configured to be aligned with the central aperture 162C in an installed position (see, e.g., FIGS. 13A-13B).

Figure 13A:
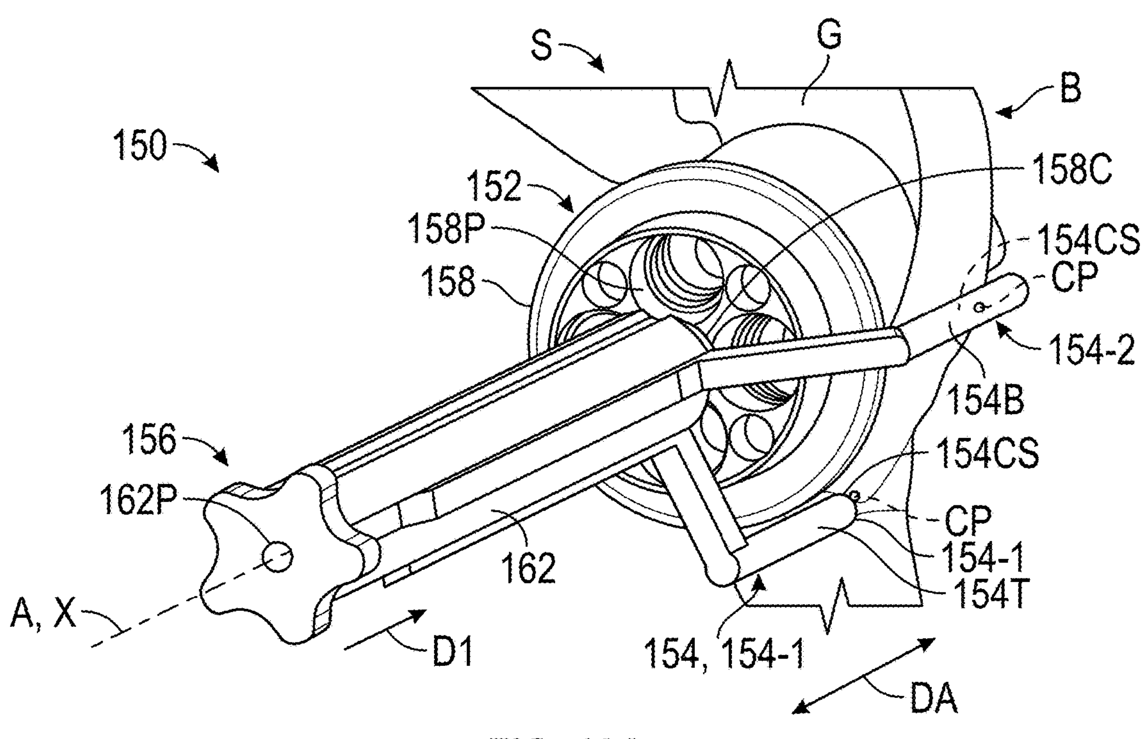
FIG. 13A illustrates the assembly of FIG. 4 including an implant, transfer members and transfer guide positioned relative to a surgical site.
Figure 13B:
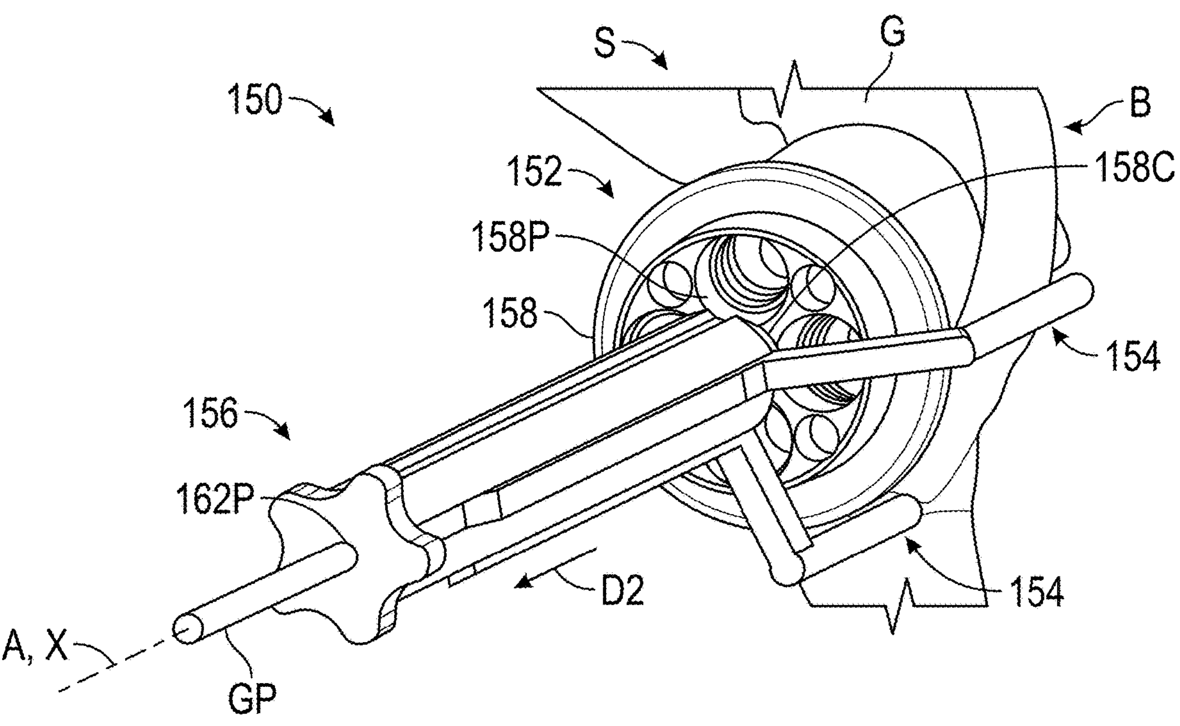
FIG. 13B illustrates a positioning object situated at the surgical site utilizing the transfer guide of FIG. 10.
Figure 13C:
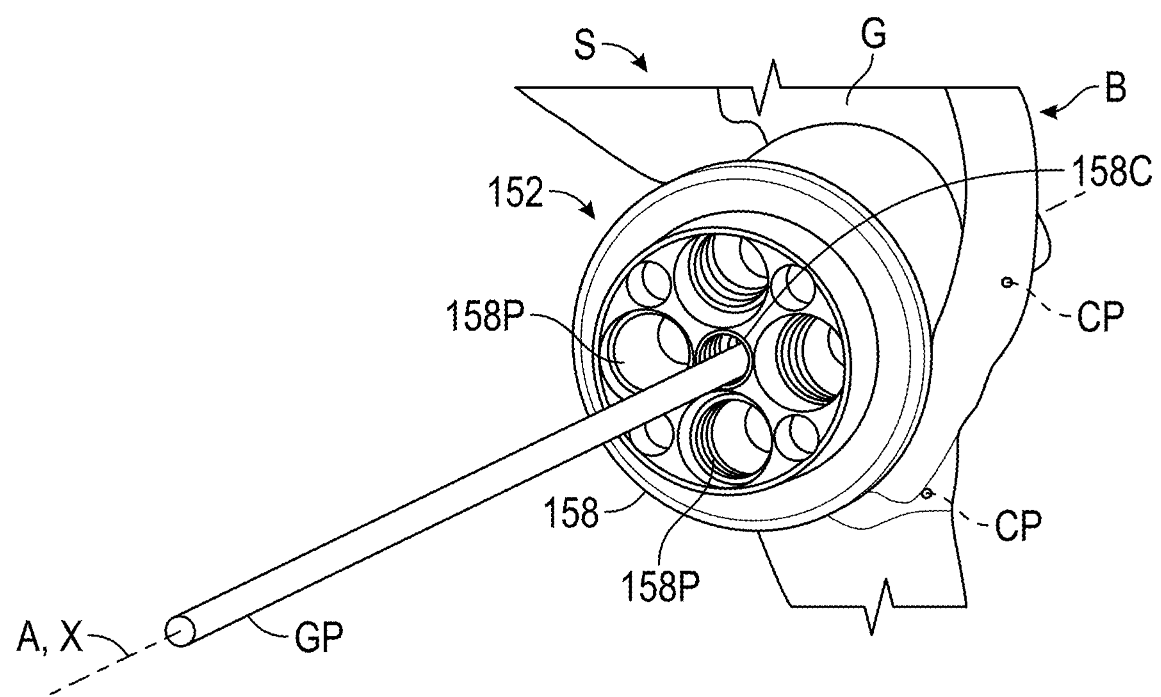
FIG. 13C illustrates the positioning object with the transfer guide of FIG. 13B removed from the surgical site.

The transfer guide 156 may be utilized to set a position and/or orientation of one or more positioning objects such as a guide pin GP, as illustrated in FIGS. 13A-13B. The central aperture 158C and respective passage 162P may be dimensioned to at least partially receive the guide pin GP to set the position and/or orientation of the guide pin GP, as illustrated in FIG. 13C. The guide pin GP may be insertable through the central aperture 158C, then through the passage 160P and then into bone B to set a position and/or orientation of the implant 152 relative to the longitudinal axis A of the transfer guide 156. The guide pin GP is illustrated in dashed lines in FIG. 8 for illustrative purposes.

Figure 6:
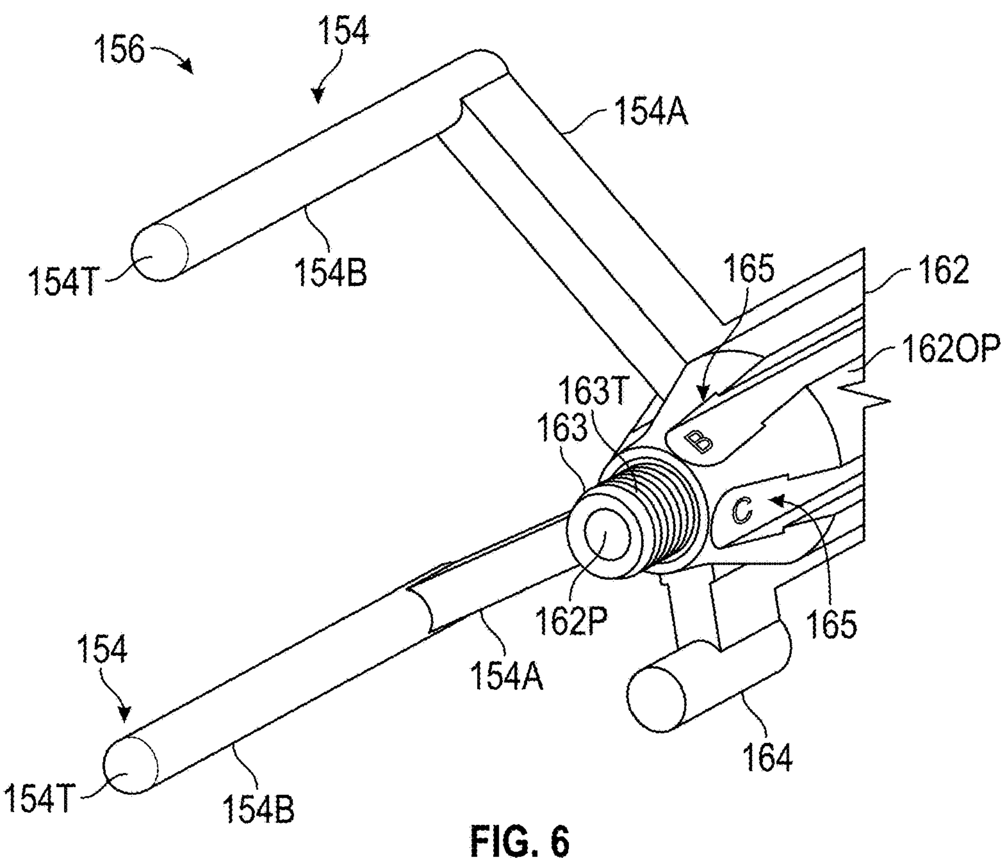
FIG. 6 illustrates a perspective view of portions of the transfer guide of FIG. 5.

Various techniques may be utilized to secure the transfer guide 156 to the implant 152. The guide body 162 may include second threads 163T (FIGS. 6-7) that mate with first threads 158T which may be disposed along the central aperture 158C of the baseplate 158 (FIG. 8) to mechanically attach the transfer guide 156 to the implant 152. In implementations, the transfer guide 156 may include a coupling feature 163 (FIGS. 5-7). The coupling feature 163 is illustrated in dashed lines in FIG. 8 for illustrative purposes. The coupling feature 163 may be a protrusion that extends outwardly from a proximal end portion of the guide body 162. The coupling feature 163 may be at least partially receivable in the central aperture 158C to secure the transfer guide 156 to the implant 152. The first threads 163T may be disposed along the coupling feature 163.

Figure 9:
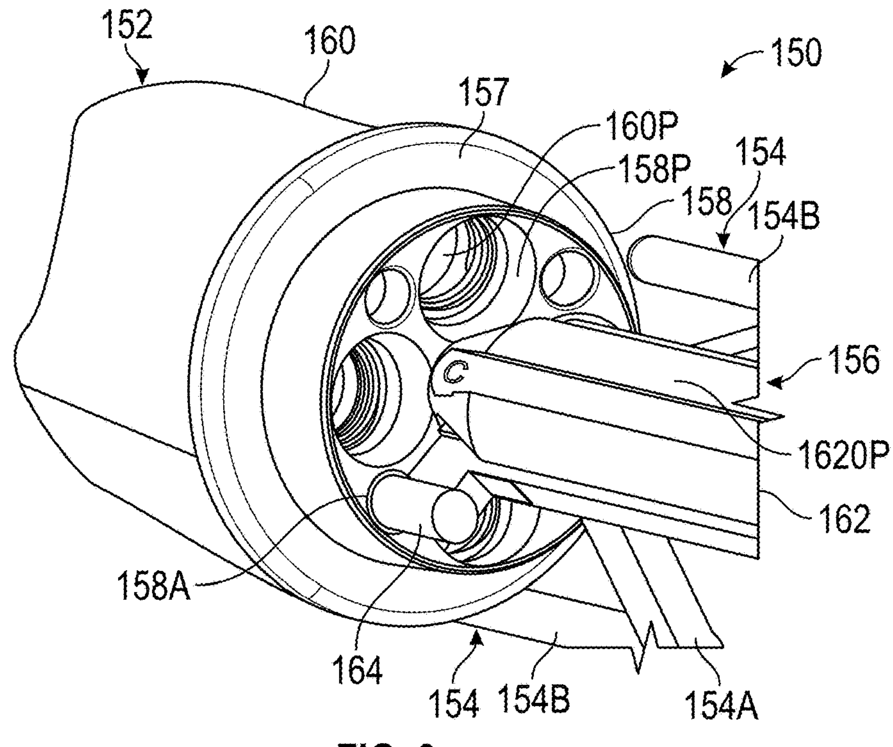
FIG. 9 illustrates a perspective view of portions of the assembly of FIG. 4.

The transfer guide 156 may include at least one alignment member 164 for positioning the transfer guide 156 relative to the implant 152. The alignment member 164 may be a protrusion dimensioned to be insertable into an aperture 158A along the baseplate 158 to position the transfer guide 156 and the implant 152 relative to each other, as illustrated in FIGS. 9-10. The alignment member 164 may be dimensioned to be insertable into the aperture 158A limit relative rotation between the transfer guide 156 and implant 152 relative to the longitudinal axis X of the implant 152. The aperture 158A may be the central aperture 158C, one of the peripheral apertures 158P, or another aperture along the baseplate 158. Although only one alignment member 164 is shown, it should be understood that more than one alignment member 164 may be utilized (see, e.g., FIG. 18).

Various techniques may be utilized to configure the transfer members 154. The transfer guide 156 may include a plurality of transfer members 154 circumferentially distributed about an outer periphery 162OP of the guide body 162 relative to the axis A, as illustrated by FIGS. 6-7.

Each of the transfer members 154 may include a first portion 154A, second portion 154B and third portion 154C (FIG. 5). The first portion 154A may extend radially outward from the guide body 162 relative to the axis A. The second portion 154B may extend axially between the first portion 154A and a terminal end portion 154T relative to the axis A. The first portion 154A and second portion 154B may establish a substantially L-shaped geometry. The terminal end portion 154T or another surface (e.g., outer periphery) of the second portion 154B of the transfer member 154 may be configured to contact bone B or other tissue along the respective contact point CP (see, e.g., FIGS. 10-12 and 13A). Each contact point CP may be established along an articular surface or non-articular surface of a joint. The terminal end portion 154T may have various geometries, such as a generally semi-spherical or rounded geometry. The third portion 154C may extend axially from the first portion 154A relative to the axis A.

Each of the transfer members 154 may be fixed at a single position or may be configured to be moveable relative to the guide body 162 between a first position (e.g., FIG. 4), a second position (e.g., FIG. 5) and one or more intermediate positions. The second portion 154B of one or more transfer members 154 may be dimensioned to be at least partially axially aligned with the augment 160 relative to the axis A in the second position and/or one or more of the intermediate positions, as illustrated in FIGS. 11-12.

The third portion 154C may be translatable along a respective slot 162S established in the outer periphery 162OP of the guide body 162 to set a position of the terminal end portion 154T of the transfer member 154 relative to the guide body 162 (see, e.g., FIG. 5).

Figure 5A:
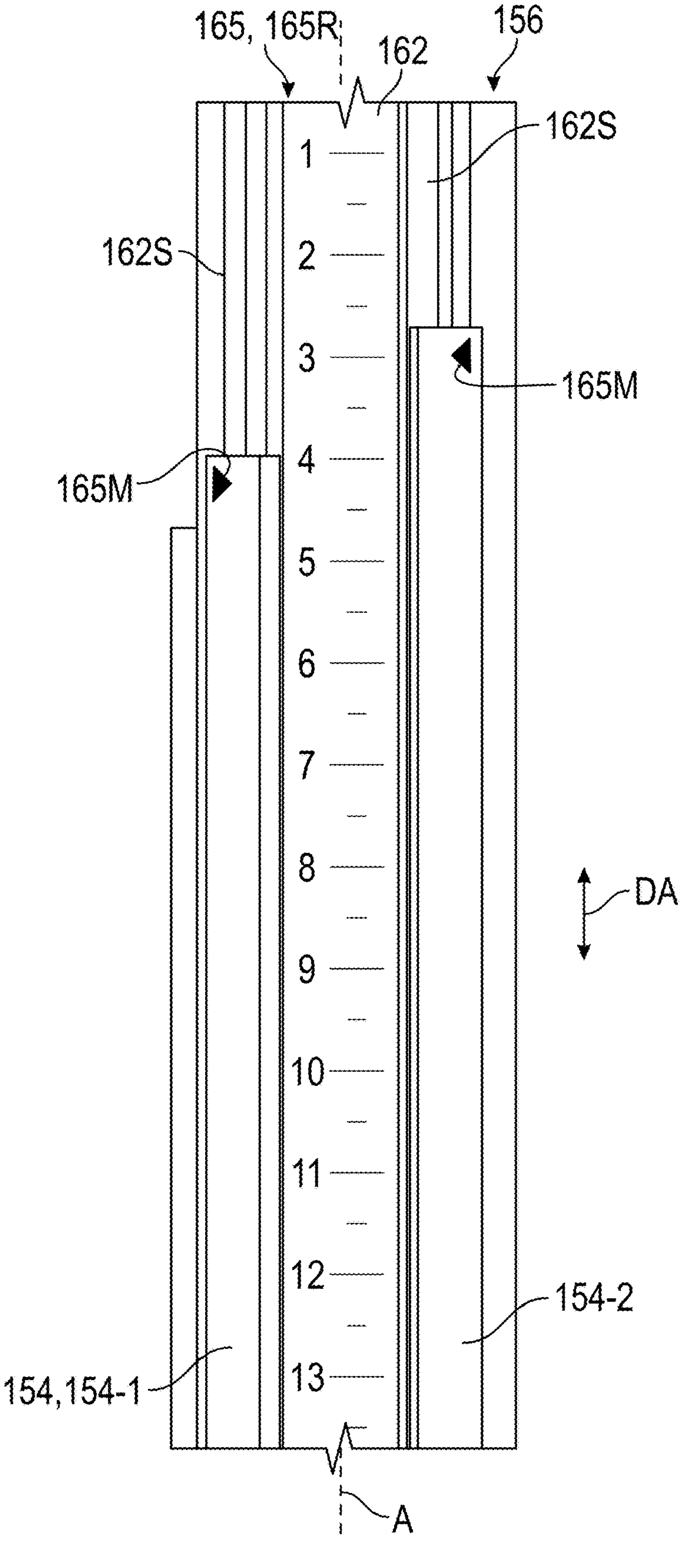
FIG. 5A illustrates aspects of the transfer guide of FIG. 5.

The transfer guide 156 may include one or more indicia 165 associated with the transfer members 154, as illustrated in FIG. 5. The surgeon or other user may utilize the indicia 165 to independently set a position of each of the transfer members 154 based on a predetermined surgical plan associated with a patient anatomy, such as one of the surgical plans 33 (FIG. 2). The indicia 165 may be associated with respective ones of the transfer members 154, and may include lettering or another indicator that may be utilized to discretely identify each of the respective transfer members 154. The indicia 165 may be formed along the guide body 162 adjacent to each of the slots 162S, or may be formed along the respective transfer members 154. In implementations, the indicia 165 may include a ruler 165M including a series of graduations which may be aligned with a marker 165M to indicate a position of the respective transfer member 154 relative to the guide body 162 and/or an axial position of the transfer member 154 relative to the longitudinal axis A, as illustrated by the transfer members 154-1, 154-2 of FIG. 5A. The transfer members 154-1, 154-2 may be independently moved along the slot 162S in a direction DA to set the position of each transfer member 154-1, 154-2 relative to the longitudinal axis A.

Various materials may be utilized to form the implants, transfer members and transfer guides disclosed herein, including metallic materials such as metals and alloys. The transfer members and/or associated transfer guides may be made of metallic and non-metallic materials including polymers and thermoplastics.

Figure 13D:
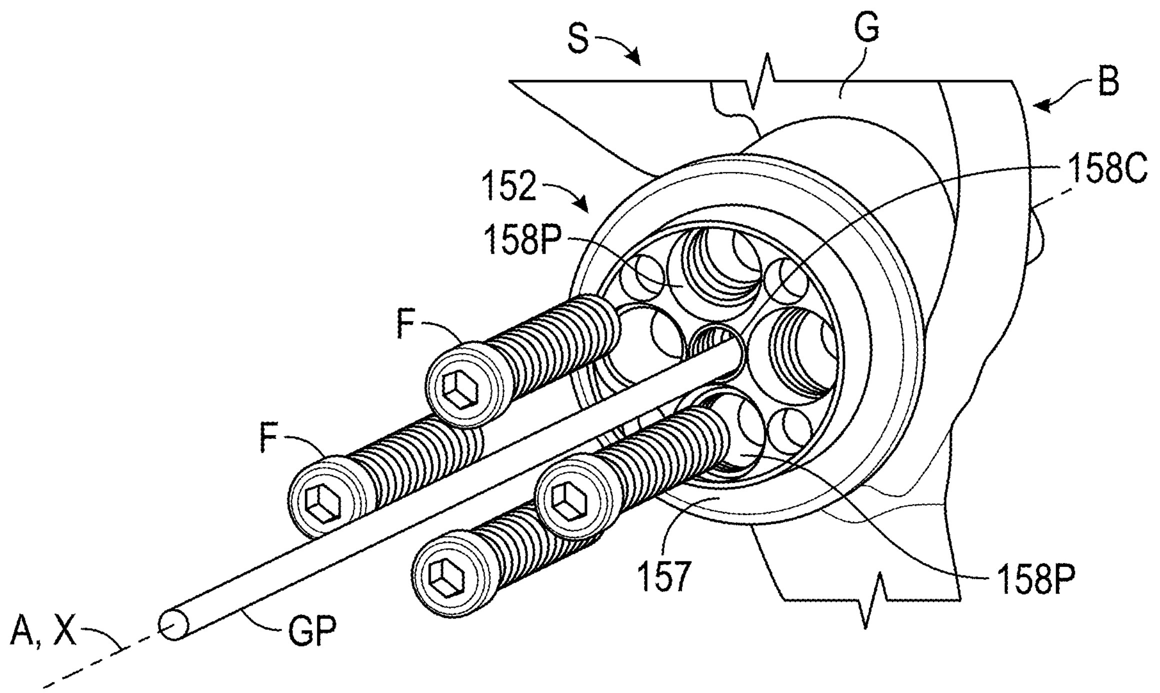
FIG. 13D illustrates fasteners positioned relative to the implant of FIG. 13A.
Figure 13E:
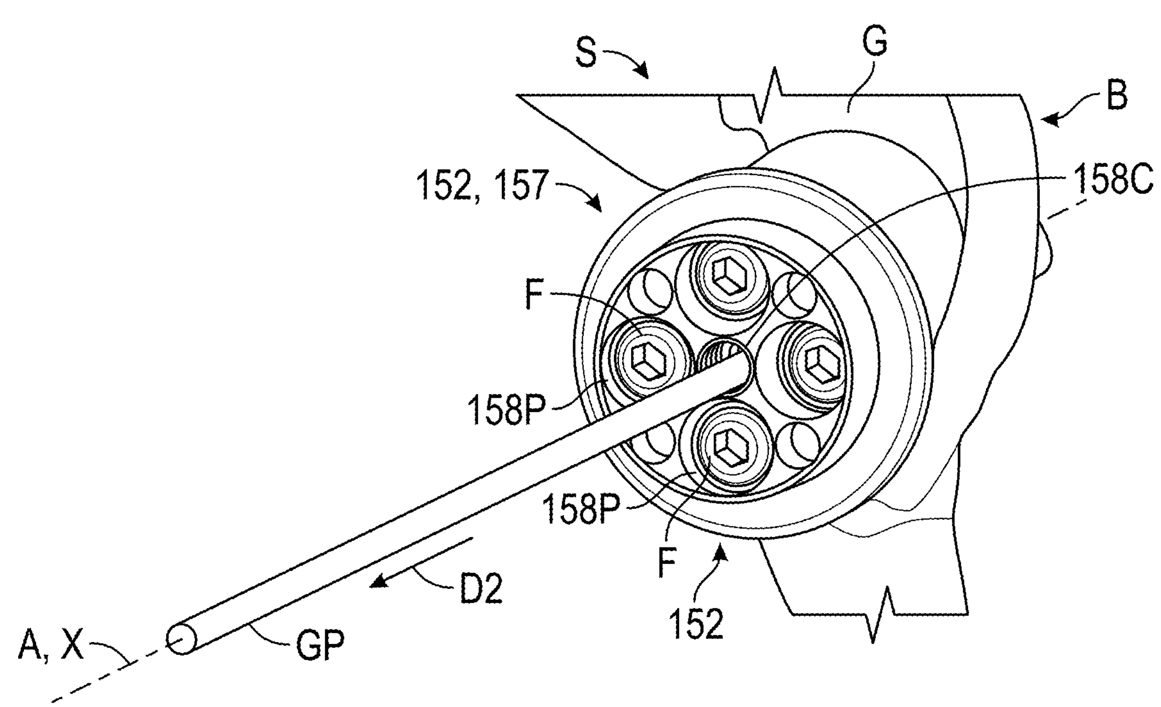
FIG. 13E illustrates the implant secured with the fasteners of FIG. 13D.
Figure 13F:
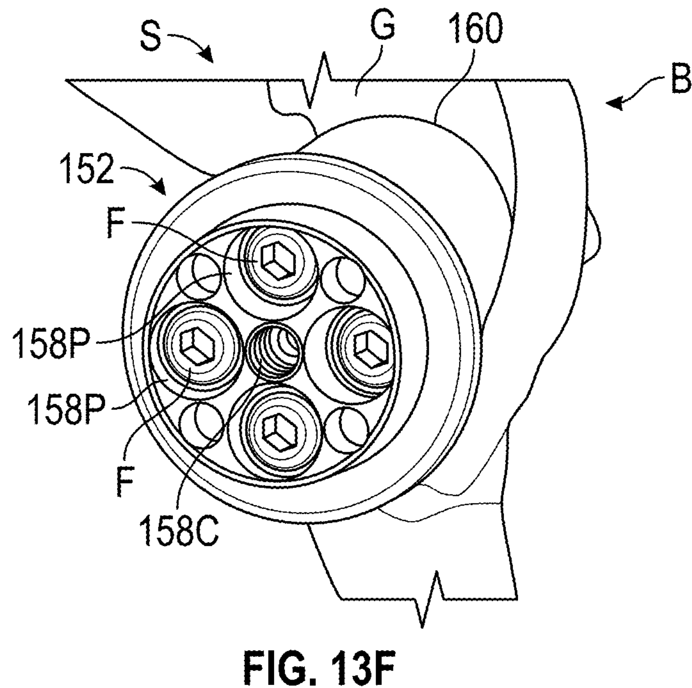
FIG. 13F illustrates the positioning object of FIG. 13E removed from the implant.
Figure 14:
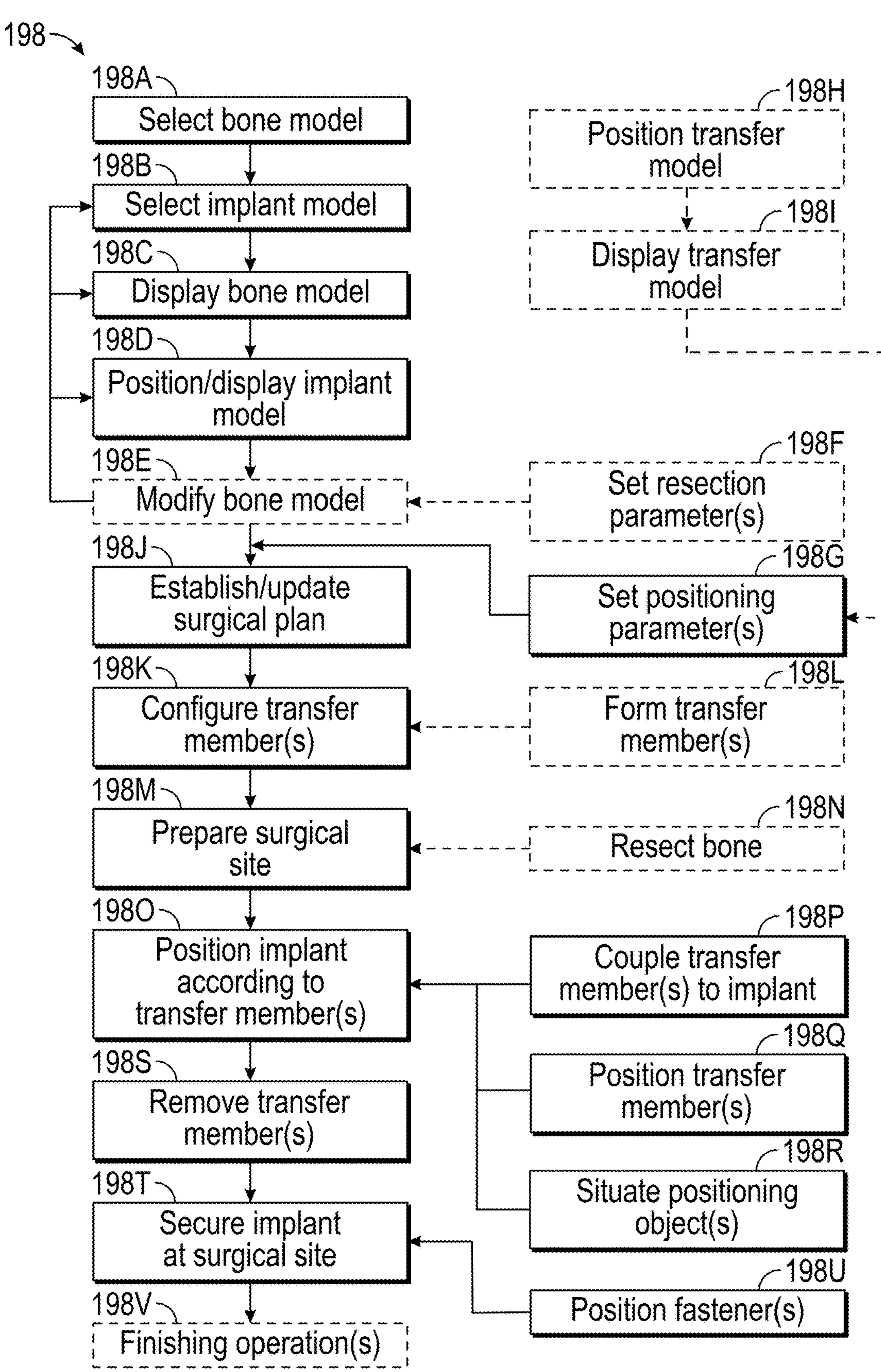
FIG. 14 illustrates an exemplary method of planning and implementing an orthopaedic procedure.

FIG. 14 illustrates an exemplary method of planning and implementing an orthopaedic procedure in a flowchart 198. The method may be utilized pre-operatively, intra-operatively and/or post-operatively to create, edit, execute and/or review a respective surgical plan, including installing one or more orthopaedic implants. The method may be utilized to perform an arthroplasty for restoring functionality to shoulders and other joints. Although the method 198 primarily refers to a shoulder reconstruction, it should be understood that the method and disclosed implants may be utilized in other locations of the patient and other surgical procedures, including any of the joints and procedures disclosed herein. The method 198 may be utilized with any of the planning systems, assemblies, implants, transfer members, transfer guides and instruments and devices disclosed herein, including assemblies 150, 250, 350, 450, 550, 650, 750 and/or 950. Fewer or additional steps than are recited below could be performed within the scope of this disclosure, and the recited order of steps is not intended to limit this disclosure. The planning system 20 and any of associated modules may be configured to execute each of the steps of the method 198. Reference is made to the planning system 20 and graphical user interface 43 of FIGS. 2-3 and the assembly 150 of FIGS. 13A-13F for illustrative purposes.

A bone model(s) 31 may be selected from one or more bone models 31 by interacting with the user interface 43 at step 198A. An implant model 32 may be selected from one or more implant models 32 by interacting with the user interface 43 at step 198B. Available bone models 31, implant models 32 and surgical plans 33 in the database(s) 29 may be presented in one or more lists in the user interface 43 may be selected in response to user interaction. The selected bone model 31 may correspond to a bone associated with a shoulder or other joint, such as a humeral head of a humerus as illustrated in FIG. 3A or a glenoid as illustrated in FIG. 3B. A selected one of the bone models 31 may be initially positioned and displayed in one or more windows 44 of the user interface 43 at step 198C. Each selected bone model 31 and selected implant model 32 may be displayed in the display windows 44-1, 44-2 and 44-3 according to any of the techniques disclosed herein, including different orientations and 2D/3D views.

The selected implant model 32 may be positioned relative to the selected bone model 31 at step 198D. Step 198D may include automatically positioning the implant model 32 relative to the bone model 31 based on one or more predetermined parameters or settings and/or landmarks associated with the selected bone model 31. Step 198D may include moving the selected implant model 32 relative to the selected bone model 31 in response to user interaction with the user interface 43. A position of the selected implant model 32 may be adjusted in one or more iterations and prior to, during and/or subsequent to any of the steps of method 198.

One or more modifications to the selected bone model 31 may be made at step 198E. The modifications may be made in response to user interaction with the user interface 43, for example. Step 198E may include setting one or more resection parameters at step 198F. The resection parameters may include a resection angle ($\alpha$) and/or resection plane R1 associated with the resection angle ($\alpha$), as illustrated in FIG. 3A. The resection angle ($\alpha$) may be established relative to an axis BA of the respective bone model 31. Step 198F may include selecting a resection angle ($\alpha$) to define a resection plane R1 along the selected bone model 31. The resection parameters may be stored in the respective surgical plan 33 (FIG. 2). Step 198D may include positioning the selected implant model 32 along the resection plane R1 such that a volume of the selected implant model 32 is at least partially received in a volume of the selected bone model 31, as illustrated in FIG. 3A.

At step 198G, one or more positioning parameters may be set relating to the transfer model 48 and associated transfer member(s), such as the transfer members 154. The positioning parameters may include any of the parameters disclosed herein, including one or more settings or dimensions associated with the transfer model 48. The parameters may be generated or set based on a virtual position VP, virtual axis VA and/or one or more contact points CP (see, e.g., FIGS. 3A-3B). The settings and dimensions may be communicated utilizing various techniques. Step 198G may include storing the settings and/or dimensions in one or more records 41 in the database 29 associated with the respective transfer model 48. In implementations, step 198G may include displaying the settings and/or dimensions in one or more graphics in the user interface 43 and/or storing the settings and/or dimensions in an output file.

Step 198G may include displaying a geometry of the selected transfer model 48 in one or more display windows 44 of the user interface 43, as illustrated in FIG. 3B. Step 198G may include positioning the geometry of the transfer model 48 relative to a geometry of the selected bone model 31 and/or implant model 32 at step 198H, as illustrated in FIG. 3B. Step 198H may include determining the position of one or more portions of the transfer model 48 relative to the selected bone model 31 and/or implant model 32, including a surface contour associated with the selected bone model 31. Step 198G may include situating the transfer model 48 at a specified orientation and/or position relative to the selected bone model 31 and/or selected implant model 32 such that a portion of the selected transfer model 48 contacts a surface contour of the selected bone model 31 and/or selected implant model 32, as illustrated in FIG. 3B. Step 198H may including positioning a virtual representation of the transfer members 154 associated with the selected transfer model 48 such that the transfer members 154 contact the surface contour of the selected bone model 31 at respective contact points CP.

At step 198J, a surgical plan 33 may be established and/or updated according to the selected bone model 31, selected implant model 32, and selected transfer model 48 at step 198E and/or according to the parameters and settings determined at steps 198F and/or 198G. Step 198J may include updating a local instance of the surgical plan 33 and/or updating the surgical plan 33 in the database 29. One or more iterations of the step(s) of the method 198 may be performed to update the surgical plan 33. The surgical plan 33 may be based on a surface profile of a bone associated with the selected bone model 31. The surgical plan 33 may include at least one or more dimensions, settings or other parameters associated with one or more transfer members 154 relative to the surface profile of the bone, which may be determined at step 198G.

Method 198 may include one or more steps to implement a predetermined surgical plan, such as a surgical plan previously established and/or updated at step 198J.

At step 198K, one or more transfer members 154 associated with the respective transfer model 48 and surgical plan 33 may be configured. Step 198K may include transferring or otherwise communicating one or more parameters associated with the transfer model 48 including one or more settings, dimensions and/or other parameters determined at step 198G or otherwise specified in the surgical plan 33. Step 198K may include forming one or more transfer members associated with the selected transfer model 48 at step 198L, including any of the transfer members such as the transfer members 154 and according to any of the techniques disclosed herein. Exemplary techniques for forming the transfer members 154 may include injection molding, casting printing and machining techniques. Step 198L may include forming one or more portions of the transfer members 154 according to a patient-specific surface contour of the patient anatomy 46. The virtual position VP, virtual axis VA and/or contact points CP and associated dimensions, settings and other parameters established at step 198G may be utilized as design constraints in the design and formation of a physical instance of the transfer model 48 and respective transfer members 154, implant 152 and/or transfer guide 156. Step 198K may occur prior, during and/or subsequent to initially positioning the implant 152 relative to bone B. The bone B may be a portion of a glenoid G, as illustrated in FIGS. 13A-13F, or another bone and associated joint of the patient anatomy.

Implementing the surgical plan 33 may include preparing the surgical site S at step 198M. Step 198M may occur prior to placement of the selected implant 152. Step 198M may including resecting a portion of the bone B at step 198N. Step 198N may occur according to the resection parameter(s) set at step 198F.

Referring to FIGS. 13A-13F, with continuing reference to FIG. 14, implementing the surgical plan may include installing one or more orthopaedic implants such as the implant 152. The implant 152 may be installed along bone B or other tissue at a surgical site S. The bone B may be associated with a respective bone model 31 (FIG. 2). The implant 152 may be associated with a respective implant model 32 specified in the surgical plan 33 (FIG. 2).

Referring to FIG. 13A, with continuing reference to FIG. 14, the selected implant 152 may be positioned according to the transfer member(s) 154 at step 198O. Step 198O may include positioning the implant 152 relative to the bone B based on a positioning of the transfer member(s) 154. Step 198O may occur such that a surface of the augment 160 contacts the bone B. The surface of the augment 160 may be a patient-specific surface dimensioned to substantially follow a surface contour of the bone B based on the predetermined surgical plan 33, as illustrated by the rear face 161B of FIG. 8.

Step 198O may include coupling the transfer members 154 and associated transfer guide 156 to the selected implant 152 at step 198P. Various techniques may be utilized to couple each of the respective transfer members 154 to the implant 152. Step 198P may include forming the transfer member(s) together with the selected implant or a transfer guide to establish a unitary construction at step 198L, including any of the implants and transfer guides disclosed herein. Other techniques may be utilized to couple the transfer members 154 to the implant 152.

Step 198P may include mechanically attaching or releasably securing the transfer guide 156 to the implant 152. The guide body 162 may be arranged to interface with the implant 152. Step 198P may include mating the second threads 163T along the coupling feature 163 and the first threads 158T along the baseplate 158 to mechanically attach the transfer guide 156 to the implant 152 (see also FIGS. 5-8). The transfer guide 156 may include at least one alignment member 164. The alignment member 164 may be a protrusion dimensioned to be insertable into an aperture 158A along the baseplate 158 to position the transfer guide 156 and the implant 152 relative to each other. Step 198P may include inserting one or more alignment members 164 into respective apertures along the baseplate 158, such as the apertures 158A or peripheral apertures 158P (see, e.g., FIGS. 9-10), to limit relative rotation between the baseplate 158 and the transfer members 154 and associated transfer guide 156 relative to the axis X of the implant 152. The aperture 158A may be the central aperture 158C, one of the peripheral apertures 158P, or another the aperture along the baseplate 158.

Step 198O may include positioning the transfer members 154 to contact tissue such as bone B at step 198Q. Step 198Q may occur during and/or subsequent to coupling the transfer members 154 and associated transfer guide 156 to the implant 152 at step 198P. Step 198O may include positioning the implant 152 together with the transfer members 154 and associated transfer guide 156 as a unit relative to the bone B or other tissue subsequent to coupling the transfer members 154 to the implant 152 at step 198P.

Positioning the transfer member(s) 154 to contact the bone B or other tissue may occur at respective predetermined contact point(s) CP (see also FIGS. 10-12 and 13C). The contact points CP may be defined according to the surgical plan 33 and may be distributed along a surface contour of the bone B, including along an articular surface or non-articular surface of a joint. The contact points CP may correspond to one or more landmarks defined by the patient anatomy, such as the glenoid rim. Each of the transfer members 154 may include a respective contact surface 154CS. The contact surface 154CS may be dimensioned with respect to one or more parameters of the surgical plan 33 determined at step 198G according to the respective contact points CP. One or more of the transfer members 154 may extend outwardly from the guide body 162 such that the contact surface 154CS contacts a surface contour of the bone B at the respective contact points CP. Each contact point CP may be a single point or a localized region along the tissue. The transfer members 154 may be dimensioned or configured according to the parameters or settings from the surgical plan 33 such that each of the contact surfaces 154CS of the transfer members 154 substantially mates with the bone B at only one predetermined position along the bone B to situate the implant 152 at the predetermined position and/or orientation specified in the surgical plan 33.

Various indicia 165 may be utilized to establish the position of the transfer members 154. In implementations, positioning the transfer members 154 at step 198Q may include aligning the marker 165M associated with the transfer member 154 and the adjacent ruler 165M to select a value along the ruler 165M (see FIG. 5A). The value may correspond to one or more settings determined in step 198G and/or otherwise included in the surgical plan established at step 198J.

Step 198O may include moving the transfer members 154 in a direction DA between a first position and a second position relative to the guide body 162 and/or implant 152 based on the dimensions(s), setting(s) and/or other parameters determined at step 198G such that the transfer members 154 contact bone B at the respective contact points CP. Direction DA may be substantially parallel to the axis A of the transfer guide 156. One or more of the transfer members 154 may contact the bone B at the terminal end portion 154T, as illustrated by transfer member 154-1, and/or may contact the bone B along the periphery of the second portion 154B of the transfer member 154, as illustrated by transfer member 154-2 (see also FIGS. 10-12). The transfer member 154-2 may be dimensioned such that the terminal end portion 154T overhangs the bone B outwardly of the respective contact point CP (see, e.g., FIG. 11). The terminal end portion 154T may overhang the bone B such that the contact point CP is established outwardly of, and is spaced apart from, an articular surface of the bone B or joint. The rear face 161B may be have a patient-specific geometry dimensioned to substantially follow a surface contour of a bone B associated with the articular surface of the bone B or joint (see, e.g., FIG. 12). In other implementations, the transfer members may be established at fixed positions relative to the guide body and/or implant (see, e.g., assemblies 250, 350, 450, 55, 650, 750 and 950).

Step 198O may occur such that the transfer member(s) 154 limit movement of the implant 152 relative to the bone B. Step 198O may occur such that the transfer member(s) 154 fix or set a position and/or orientation of the implant 152 relative to the bone B, which may correspond to the parameters established at step 198G, including a predetermined virtual position VP, virtual axis VA and/or contact point(s) CP associated with the surgical plan 33.

Referring to FIG. 13B, with continuing reference to FIG. 14, step 198O may include situating one or more positioning objects relative to the surgical site S at step 198R. The positioning objects may include one or more guide pins, as illustrated by guide pin GP. Step 198R may include positioning the guide pin GP at least partially into and through the passage 162P in the guide body 162, then through the implant 152 (FIG. 13C), and then into the bone B. The guide pin GP may enter the bone B at a position and/or orientation substantially equal to the predetermined virtual position VP and/or virtual axis VA associated with the surgical plan 33. The implant 152 may be spaced apart from each of the contact points CP in response to positioning the guide pin GP in the bone B.

Referring to FIG. 13C, with continuing reference to FIG. 14, the transfer members 154 and associated transfer guide 156 may be removed from the implant 152 at the surgical site S at step 198S. Step 198S may include moving the transfer guide 156 in a second direction D2 (FIG. 13B). The second direction D2 may be substantially parallel to the axis A and may be opposed to the first direction D1 (FIG. 13A).

Referring to FIGS. 13D-13E, the implant 152 may be secured to the bone B at the surgical site S at step 198T. Various techniques may be utilized to secure the implant 152. Step 198T may include positioning one or more fasteners F in respective peripheral apertures 158P and then into the bone B to secure the implant 152 at the surgical site S at step 198U. The guide pin GP may be removed from the implant 152 by moving the guide pin GP in the direction D2 subsequent to securing the implant 152 with the fasteners F, as illustrated in FIG. 13F. A fastener may be positioned in the central aperture 158C subsequent to removing the guide pin GP. Fasteners F may include any of the fasteners disclosed herein, such as compression screws.

At step 198V, one or more finishing operations may be performed at the surgical site S. Step 198V may include coupling an articulation member 167 to the baseplate 158, as illustrated in FIG. 8 (shown in dashed lines for illustrative purposes). The articulation member 167 may include an articulation surface dimensioned to cooperate with an adjacent bone or implant. The articulation surface may have various geometries including a generally concave or convex geometry. Step 198V may include closing an incision made in the patient to situate the implant 152.

Figure 15:
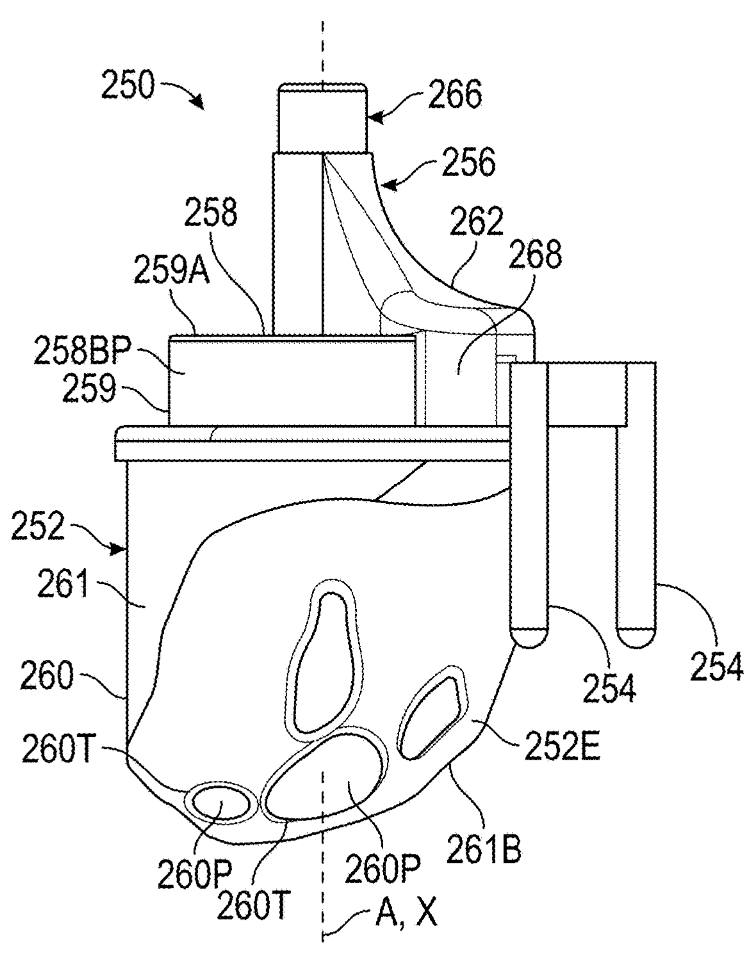
FIG. 15 illustrates another exemplary orthopaedic assembly including an implant, transfer guide and transfer members and incorporating a coupling member.
Figure 16:
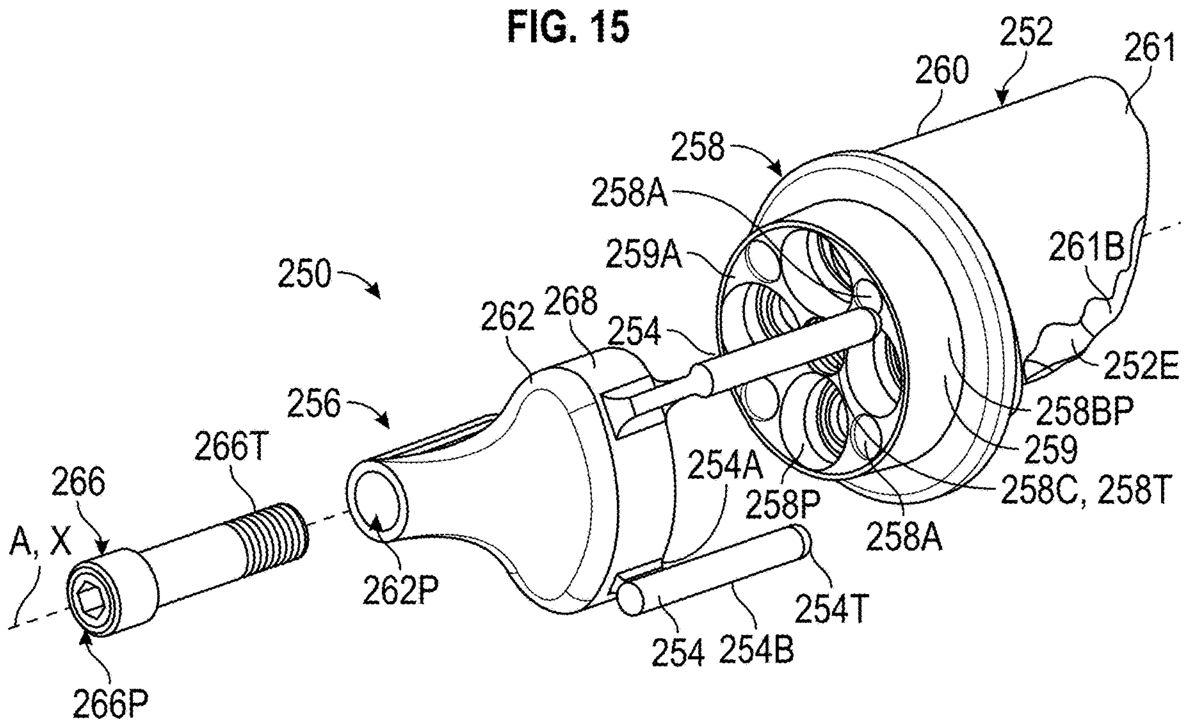
FIG. 16 illustrates an exploded view of the assembly of FIG. 15.

FIGS. 15-16 illustrate another exemplary assembly 250 for an orthopaedic procedure. The assembly 250 may be utilized to restore functionality to any of the joints and other anatomy according to any of the techniques disclosed herein. The assembly 250 may include an orthopaedic implant 252 and one or more transfer members (e.g., objects) 254. The transfer members 254 may be coupled to the implant 252. The implant 252 and transfer members 254 may be configured to abut or contact bone B or other tissue (see, e.g., FIGS. 19-20). The implant 252 and transfer members 254 may be dimensioned utilizing any of the techniques disclosed herein, including dimensions based on a predetermined surgical plan established by the planning system 20 and/or method 198.

The implant 252 may include a baseplate 258 and augment 260 extending outwardly from the baseplate 258. A rear face 261B of the augment 260 may establish an external surface 252E of the implant 252. The rear face 261B may be have a patient-specific geometry dimensioned to substantially follows a surface contour of a bone B associated with a respective patient, as illustrated in FIG. 20.

The assembly 250 may include a transfer guide 256 configured to interface with the implant 252. The transfer guide 256 may incorporate one or more of the transfer members 254. The transfer members 254 may be dimensioned to extend outwardly from a guide body 262 of the transfer guide 256. One or more of the transfer members 254 may be positioned relative to the guide body 262 based on a predetermined surgical plan.

Figure 17:
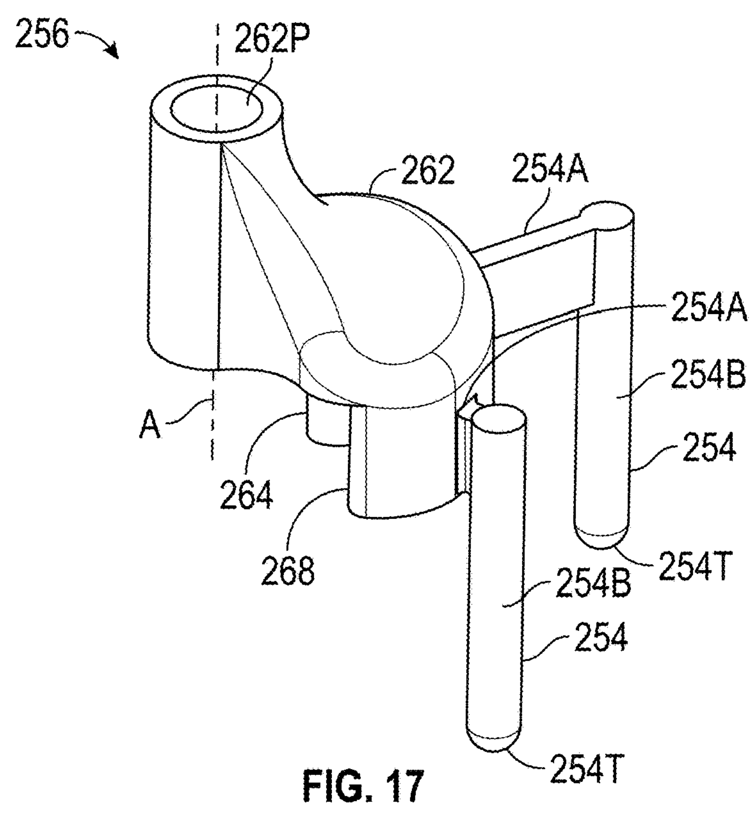
FIG. 17 illustrates a perspective view of a transfer guide of the assembly of FIG. 15.
Figure 18:
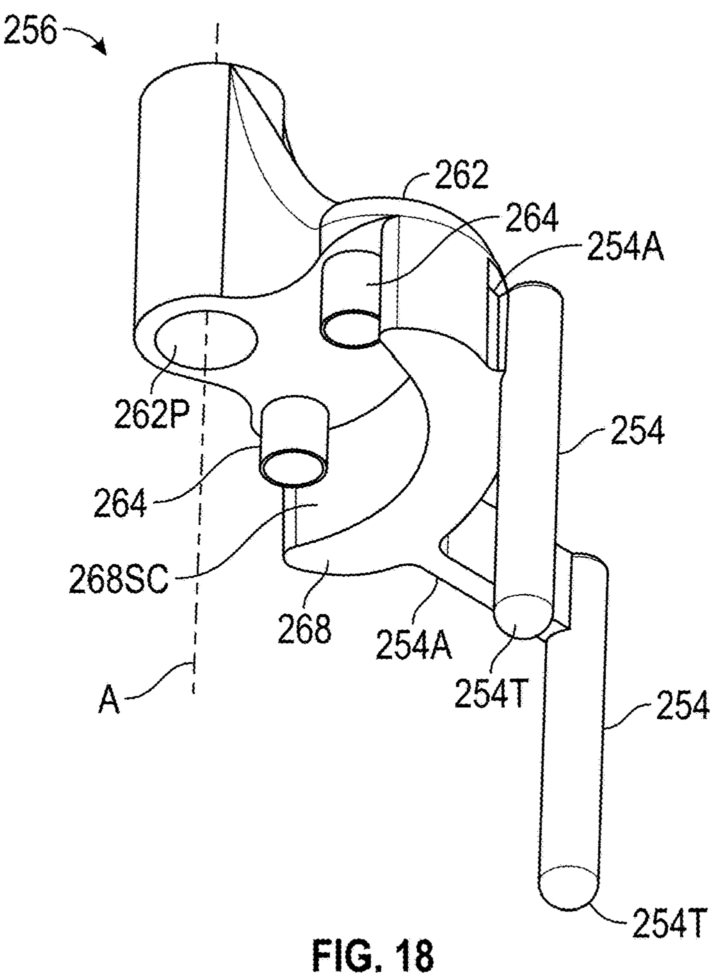
FIG. 18 illustrates another perspective view of a transfer guide of the assembly of FIG. 15.
Figure 19:
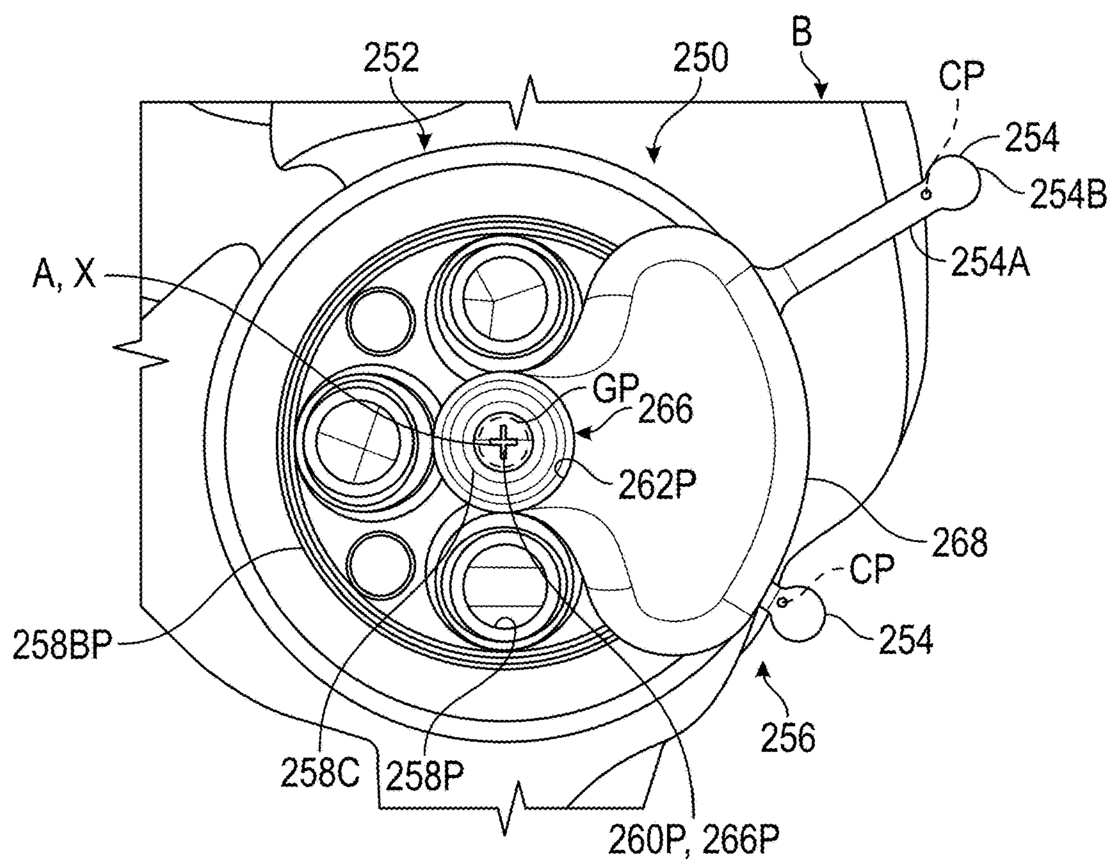
FIG. 19 illustrates an axial view of the assembly of FIG. 15 positioned at a surgical site.

Referring to FIGS. 16-18, with continuing reference to FIG. 15, each of the transfer members 254 may be integrally formed with the guide body 262 such that a position of each of the transfer members 254 is fixed relative to the guide body 262. Each of the transfer members 254 may include a first portion 254A extending radially outward from the guide body 262 and a second portion 254B extending axially between the first portion 254A and a terminal end portion 254T. The terminal end portion 254T and/or another surface of the second portion 254B may be configured to abut bone B or other tissue adjacent the implant 252, as illustrated in FIGS. 19-20. A surgeon or user may position the implant 252 based on a position of the transfer members 254 and/or transfer guide 256 relative to the bone B.

Figure 20:
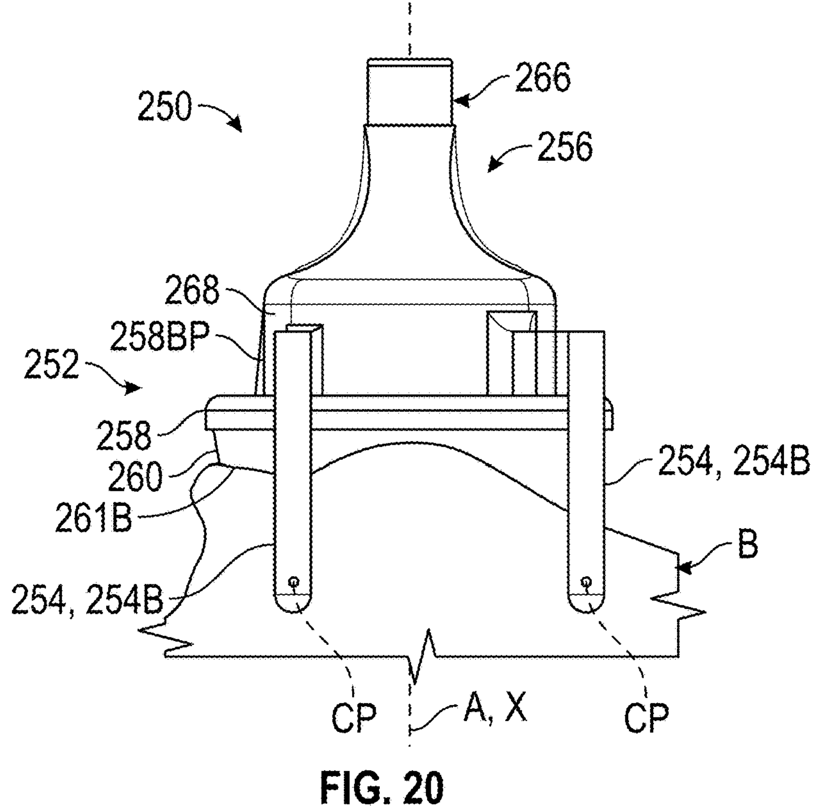
FIG. 20 illustrates a side view of the assembly of FIG. 19.

Referring to FIGS. 19-20, with continuing reference to FIGS. 15 and 17-18, the assembly 250 may include a coupling member 266 configured to secure the transfer guide 256 to the implant 252. The guide body 262 may include a passage 262P dimensioned to receive the coupling member 266, as illustrated in FIG. 19. The coupling member 266 may be circumferentially spaced apart from each of the transfer members 254 relative to a longitudinal axis A of the implant 252 in an installed position. The coupling member 266 may be a fastener insertable into the passage 262P and a central aperture 258C of the baseplate 258 to mechanically attach the transfer guide 256 to the implant 252. The coupling member 266 may include threads 266T that are dimensioned to mate with threads 258T along the central aperture 258C (FIG. 16) to mechanically attach the transfer guide 256 to the implant 252. One or more of the transfer members 254 may be dimensioned to be at least partially axially aligned with the augment 260 relative to the axis X of the implant 152 and/or axis A of the transfer guide 256 in the installed position, as illustrated in FIGS. 15 and 20.

The coupling member 266 may include a passage 266P. The passage 266P may be dimensioned to receive one or more positioning objects such as a guide pin GP. The guide pin GP may be insertable through the central aperture 258C and into the bone B to set a position of the implant 252, as illustrated in FIG. 19 and FIG. 21B. Guide pin GP is shown in dashed lines in FIG. 19 for illustrative purposes.

The transfer guide 256 may include an abutment member 268 that extends outwardly from the guide body 262. The abutment member 268 may include a surface contour 268SC (FIG. 18) dimensioned to at least partially follow a periphery 258BP along the plate body 259 of the baseplate 258 to limit relative radial movement between the transfer guide 256 and implant 252 relative to the axes A, X. The transfer guide 256 may include one or more alignment members 264 extending inwardly from the guide body 262 (FIGS. 17-18). The alignment members 264 may be spaced apart from the abutment member 268. One or more of the transfer members 254 may extend outwardly from the abutment member 268.

FIGS. 21A-21F illustrate various states of installing the implant 252 to bone B at a surgical site S utilizing the transfer members 254 and associated transfer guide 256. Any of the steps of the method 198 may be utilized to install the implant 252. Reference is made to the method 198 of FIG. 14 for illustrative purposes.

The method 198 may include integrally forming the transfer members 254 with the guide body 262 at step 198L based on one or more dimensions established at step 198G. Integrally forming the transfer members 254 with the guide body 262 may occur subsequent to the establishing a predetermined surgical plan at step 198J.

Figure 21A:
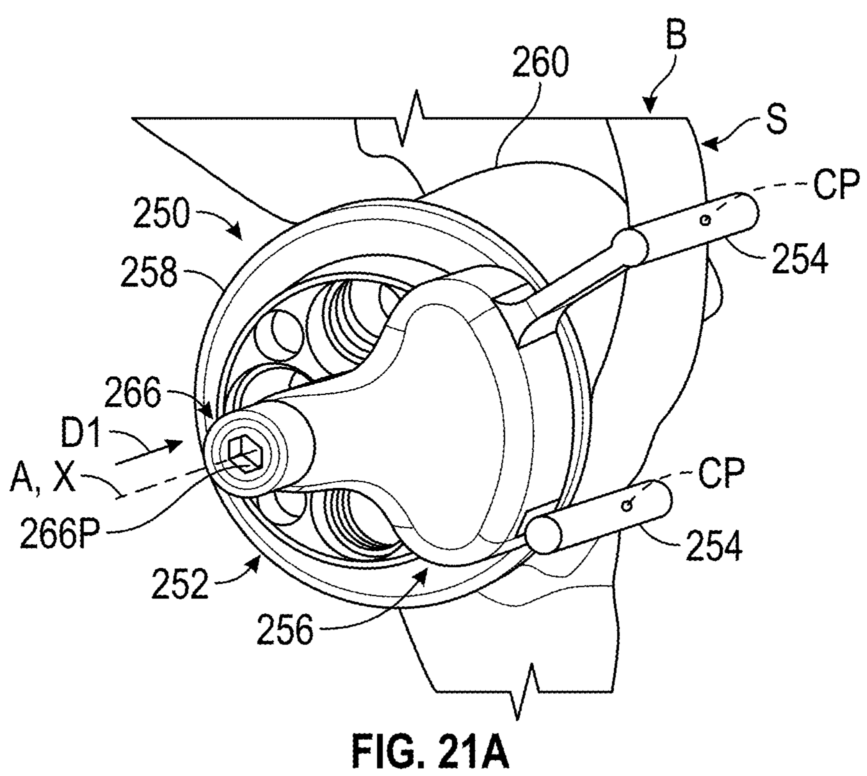
FIG. 21A illustrates the assembly of FIG. 15 including a transfer guide, coupling member and implant positioned relative to a surgical site.
Figure 21B:
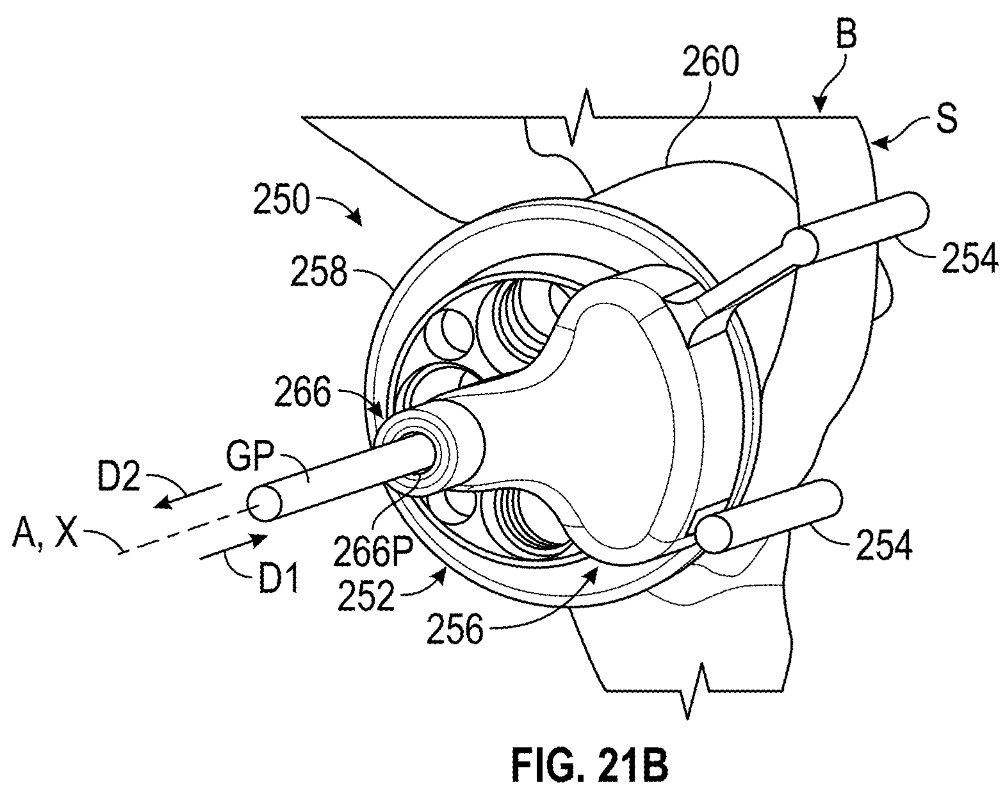
FIG. 21B illustrates a positioning object situated at the surgical site utilizing the coupling member of FIG. 21A.

Referring to FIG. 21A, with reference to FIG. 14, the implant 252 may be positioned at the surgical site S according to positioning the transfer members 254 at step 198O. Step 198O may include positioning the transfer guide 256 relative to the implant 252. The coupling member 266 may be moved in a direction D1 to mechanically attach or otherwise secure the transfer guide 256 to the implant 252 at step 198P.

Referring to FIG. 21B, with reference to FIG. 14, at least one positioning object such as a guide pin GP may be situated relative to the surgical site S at step 198R. Step 198R may include positioning the guide pin GP by moving the guide pin GP in the direction D1 and inserting the guide pin GP into the passage 266P of the coupling member 266, then through the central aperture 258P (FIG. 21C) of the baseplate 258, and then into the bone B to set a position and orientation of the implant 252. The guide pin GP may enter the bone B at a position and/or orientation substantially equal to the predetermined virtual position VP and/or virtual axis VA associated with the surgical plan established at step 198J.

Figure 21C:
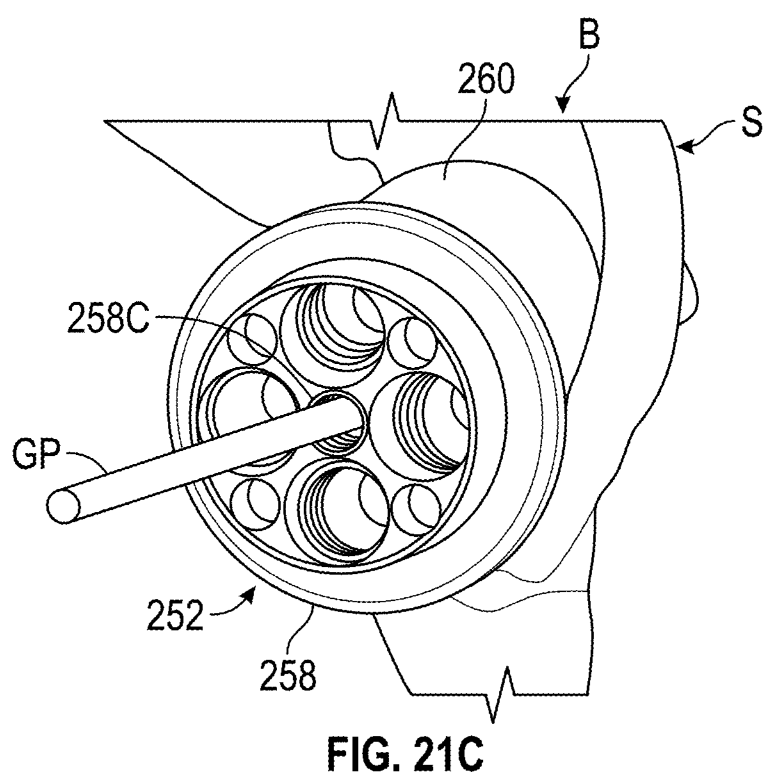
FIG. 21C illustrates the coupling member and transfer guide of FIG. 21B removed from the surgical site.

Referring to FIGS. 21B-21C, the coupling member 266 and transfer guide 256 may be uncoupled from the implant 252 and moved in a direction D2 away from the surgical site S to remove the transfer members 254 at step 198S.

Figure 21D:
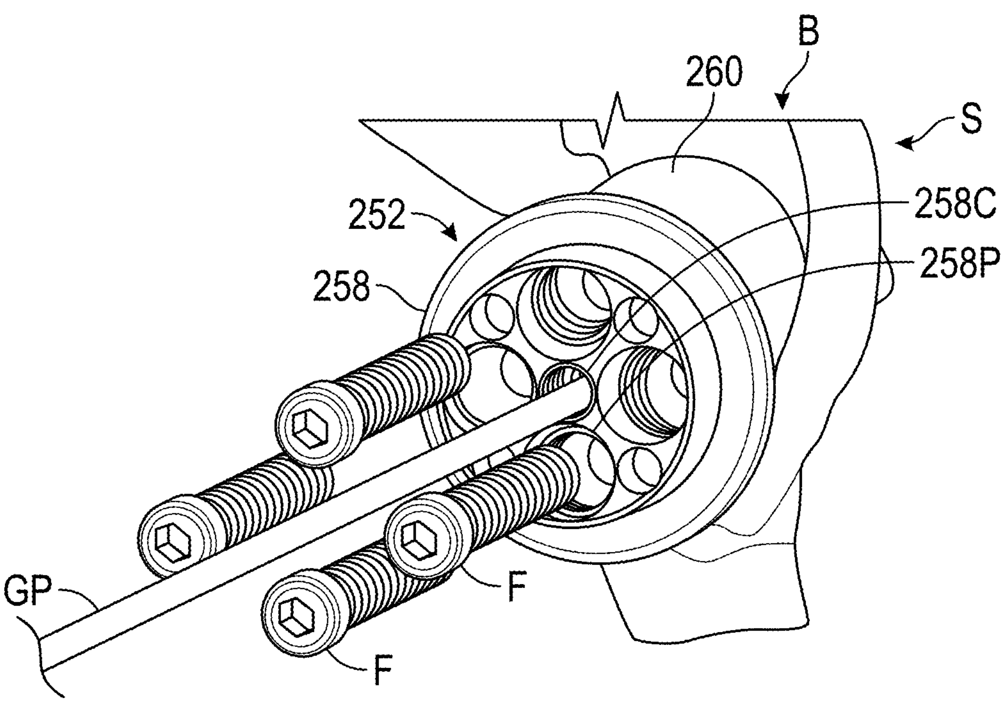
FIG. 21D illustrates fasteners positioned relative to the implant of FIG. 21C.
Figure 21E:
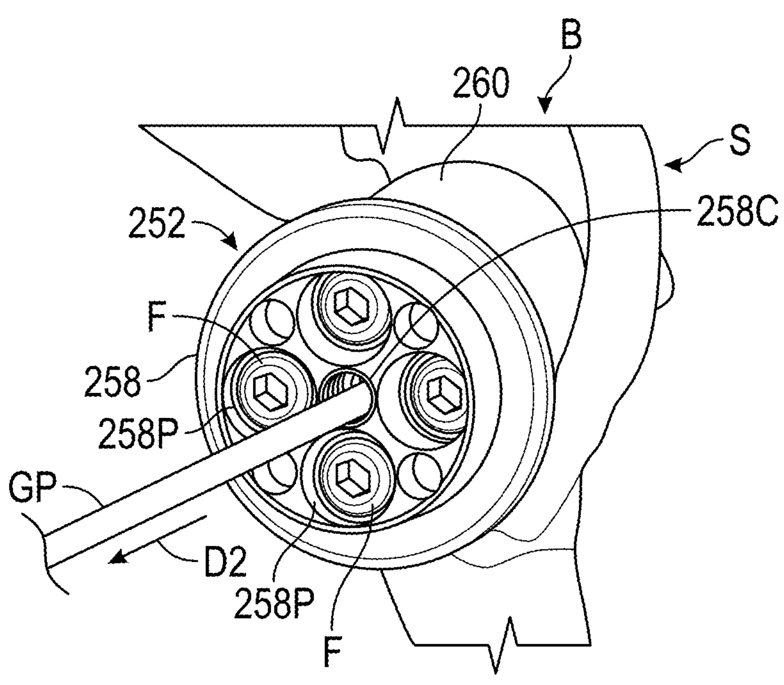
FIG. 21E illustrates the implant secured with the fasteners of FIG. 21D.
Figure 21F:
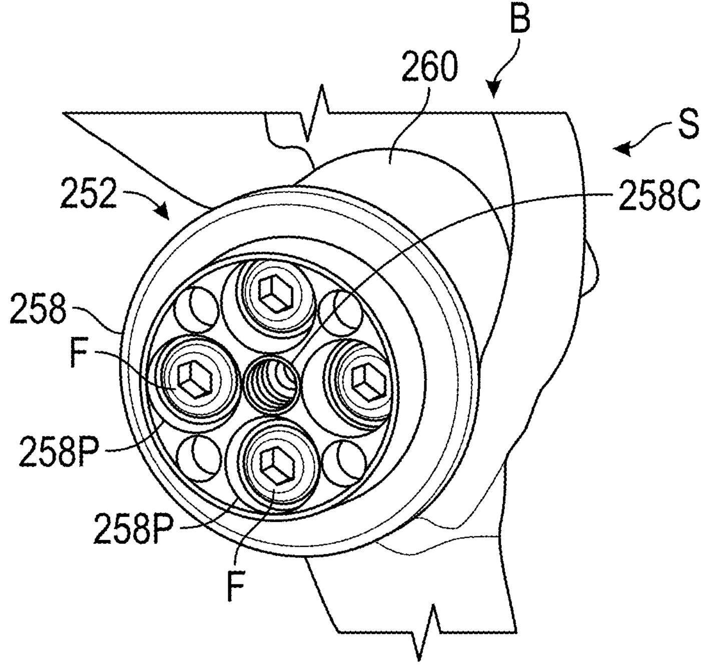
FIG. 21F illustrates the positioning object of FIG. 21E removed from the implant.

Referring to FIGS. 21D-21E, the implant 252 may be secured to the surgical site S at step 198T. One or more fasteners F may be positioned in the peripheral apertures 258P to secure the implant 252 at step 198U. The guide pin GP may be removed from the implant 252 and moved in the direction D2 away from the surgical site S, as illustrated in FIGS. 21E-21F.

Figures 22, 23:
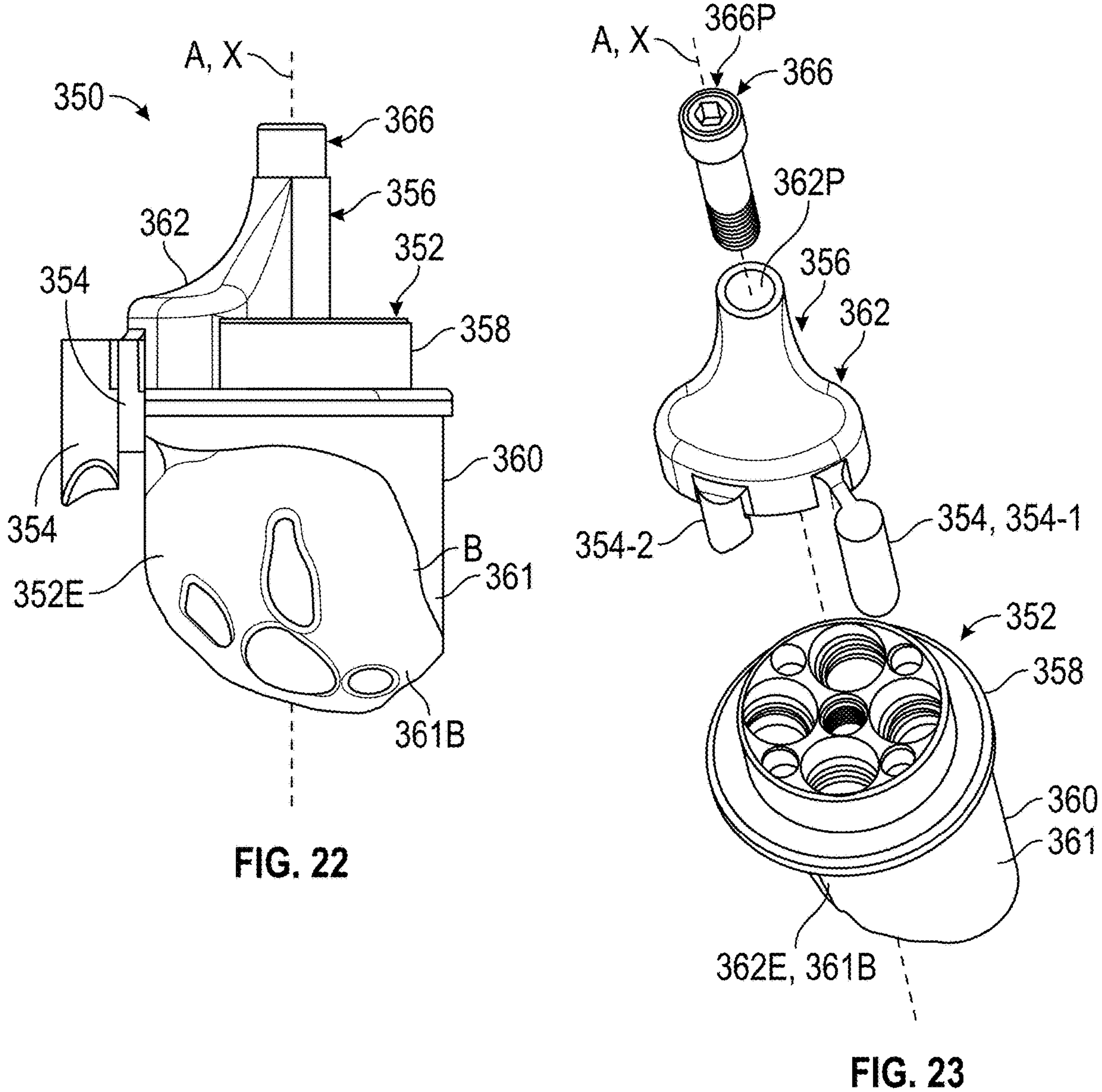
FIG. 22 illustrates another exemplary orthopaedic assembly including an implant, transfer guide and transfer members that may have a patient-specific configuration and may incorporate a coupling member.
FIG. 23 illustrates an exploded view of the assembly of FIG. 22.

FIGS. 22-23 illustrate another exemplary assembly 350 for an orthopaedic procedure. The assembly 350 may be utilized to restore functionality to any of the joints and other anatomy according to any of the techniques disclosed herein. The assembly 350 may include an orthopaedic implant 352 and one or more transfer members (e.g., objects) 354.

The implant 352 may include a baseplate 358 and augment 360 extending outwardly from the baseplate 358. A rear face 361B of the augment 360 may establish an external surface 352E of the implant 352. The rear face 361B may have a patient-specific geometry dimensioned to substantially follow a surface contour of a bone B of a patient (bone B shown in dashed lines in FIG. 22 for illustrative purposes).

The transfer members 354 may be coupled to the implant 352. The implant 352 and each transfer member 354 may be configured to abut or contact bone B or other tissue (see, e.g., FIGS. 26, 27A and 27C). The implant 352 and transfer members 354 may be dimensioned utilizing any of the techniques disclosed herein, including dimensions based on a predetermined surgical plan. The predetermined surgical plan may be established by the planning system 20 and/or method 198. The assembly 350 may include a transfer guide 356 configured to interface with the implant 352. The transfer guide 356 may incorporate one or more of the transfer members 354.

Figure 24:
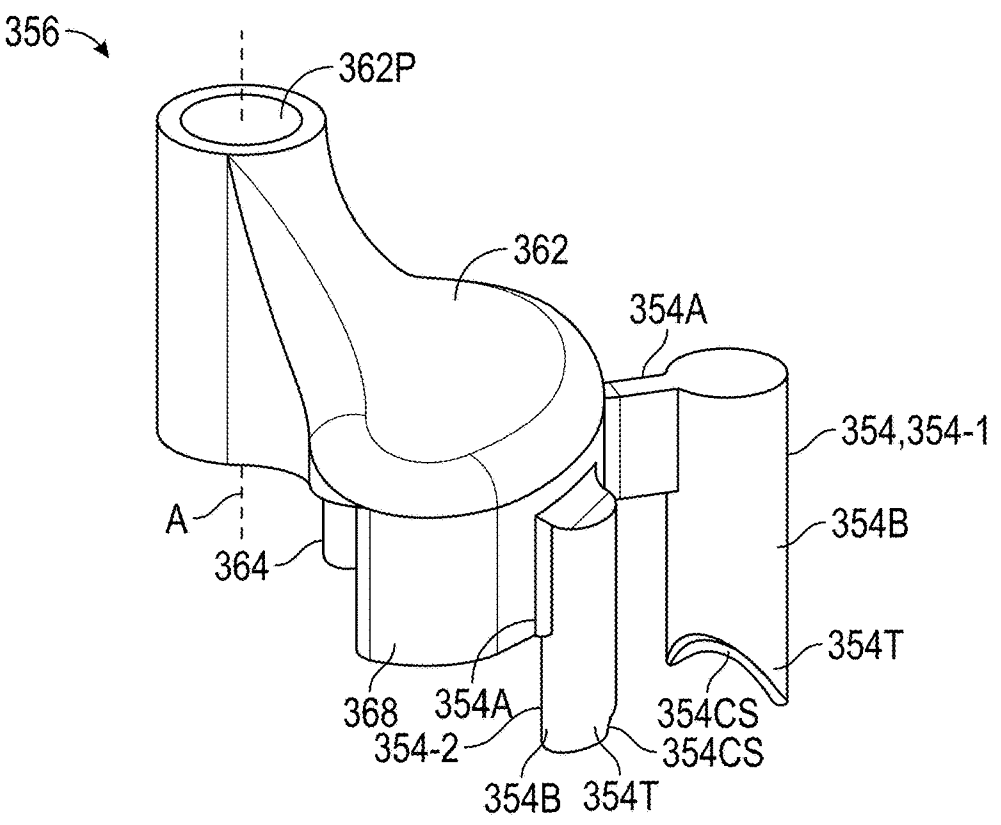
FIG. 24 illustrates a perspective view of the transfer guide of FIG. 22.
Figure 25:
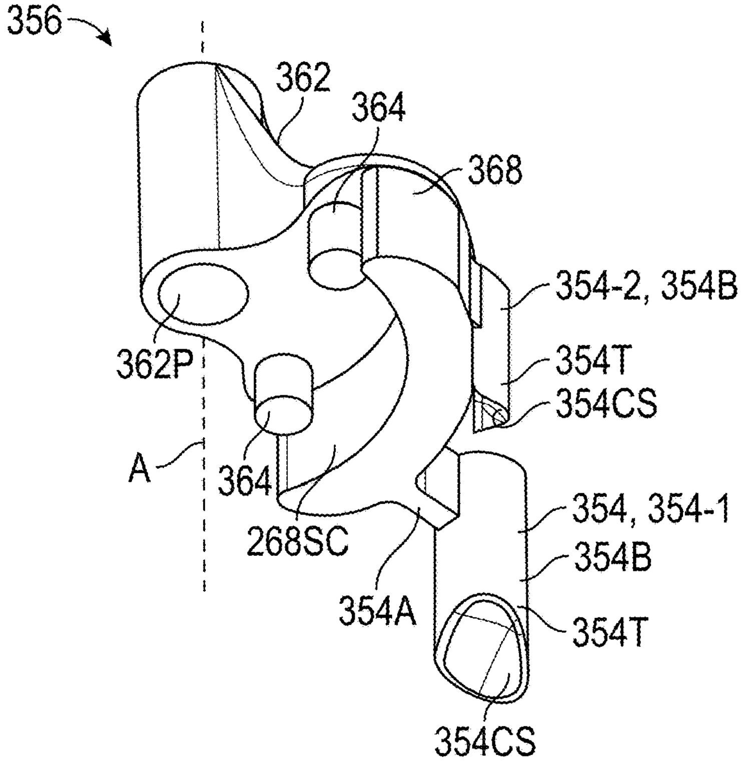
FIG. 25 illustrates another perspective view of the transfer guide of FIG. 22.
Figure 26:
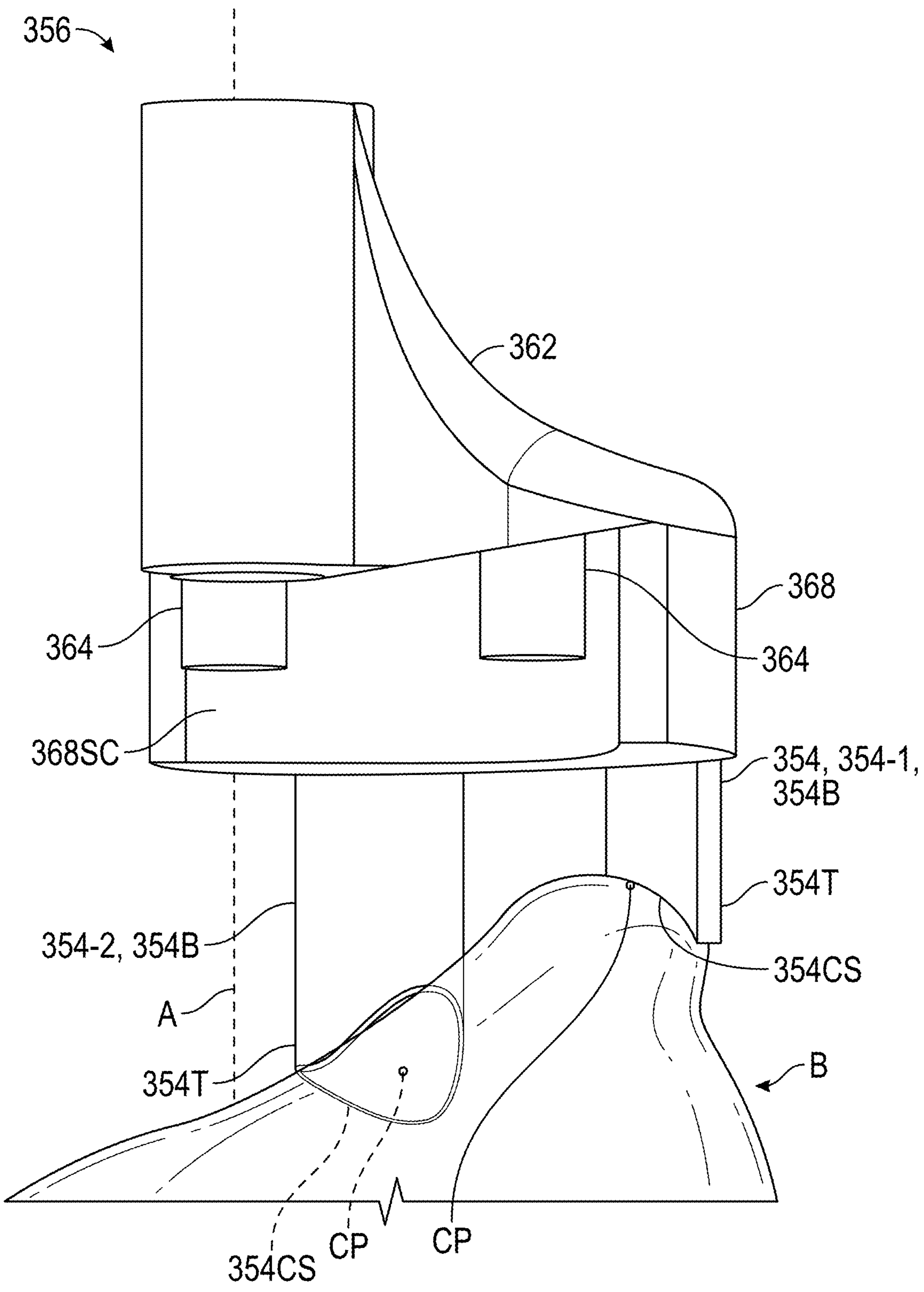
FIG. 26 illustrates a perspective view of the transfer guide of FIG. 22 situated relative to tissue.
Figure 27A:
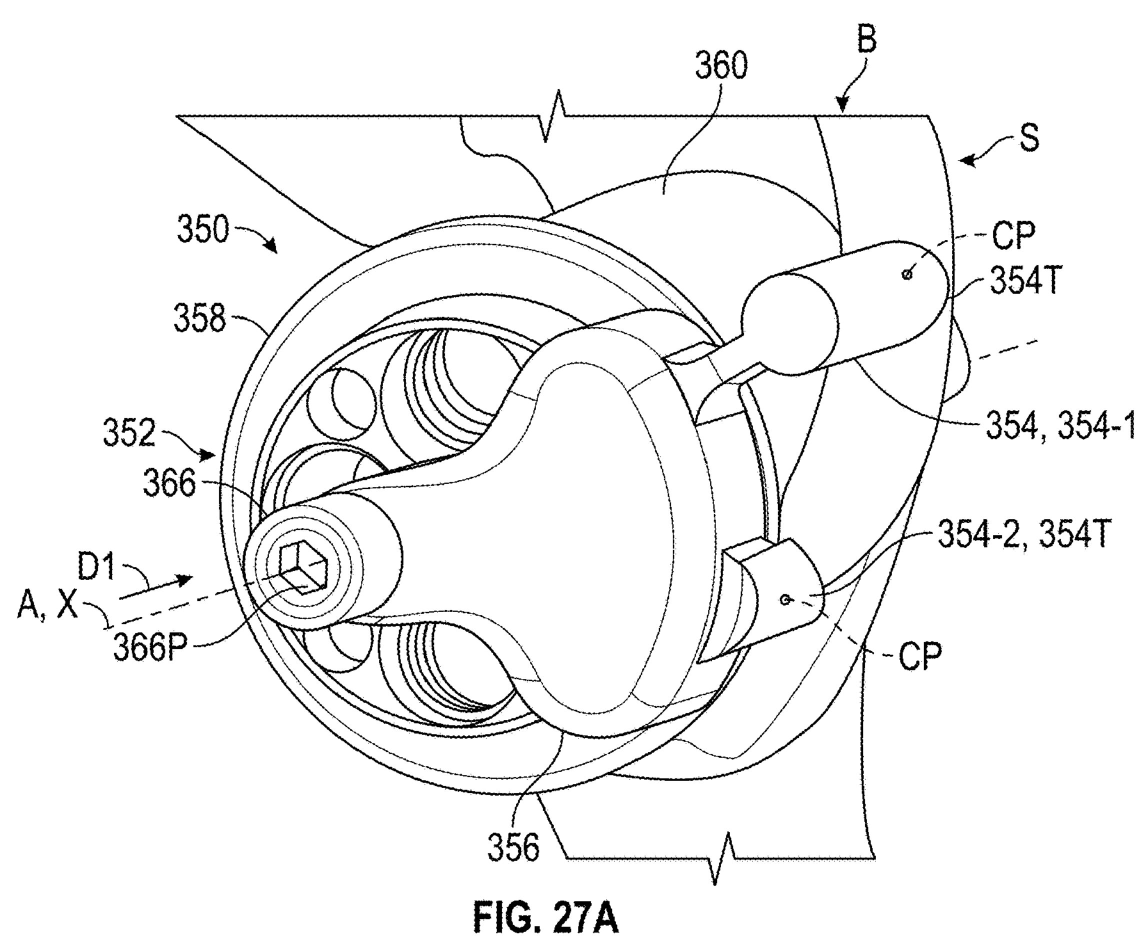
FIG. 27A illustrates the assembly of FIG. 22 including a transfer guide, coupling member and implant positioned relative to a surgical site.

Referring to FIGS. 24-26, with continuing reference to FIGS. 22-23, each of the transfer members 354 may be integrally formed with a guide body 362 such that a position of the transfer members 354 is fixed relative to the guide body 362. Each of the transfer members 354 may extend from the guide body 362 to a terminal end portion 354T. Each of the transfer members 354 may include a first portion 354A extending radially outward from an abutment member 368 or the guide body 362. Each of the transfer members 354 may include a second portion 354B extending axially between the first portion 354A and terminal end portion 354T. The second portion 354B may establish the terminal end portion 354T. The terminal end portion 354T and/or another surface of the second portion 354B may be configured to abut bone B or other tissue adjacent the implant 352, as illustrated in FIG. 26. A surgeon or user may position the implant 352 based on a position of the transfer members 354 and/or transfer guide 356 relative to the bone B.

Each of the transfer members 354 may be positioned relative to the guide body 362 based on a predetermined surgical plan, such as the surgical plan 33 (FIG. 2). In implementations, one or more surfaces of the transfer members 354 may be dimensioned based on the predetermined surgical plan.

Figure 27B:
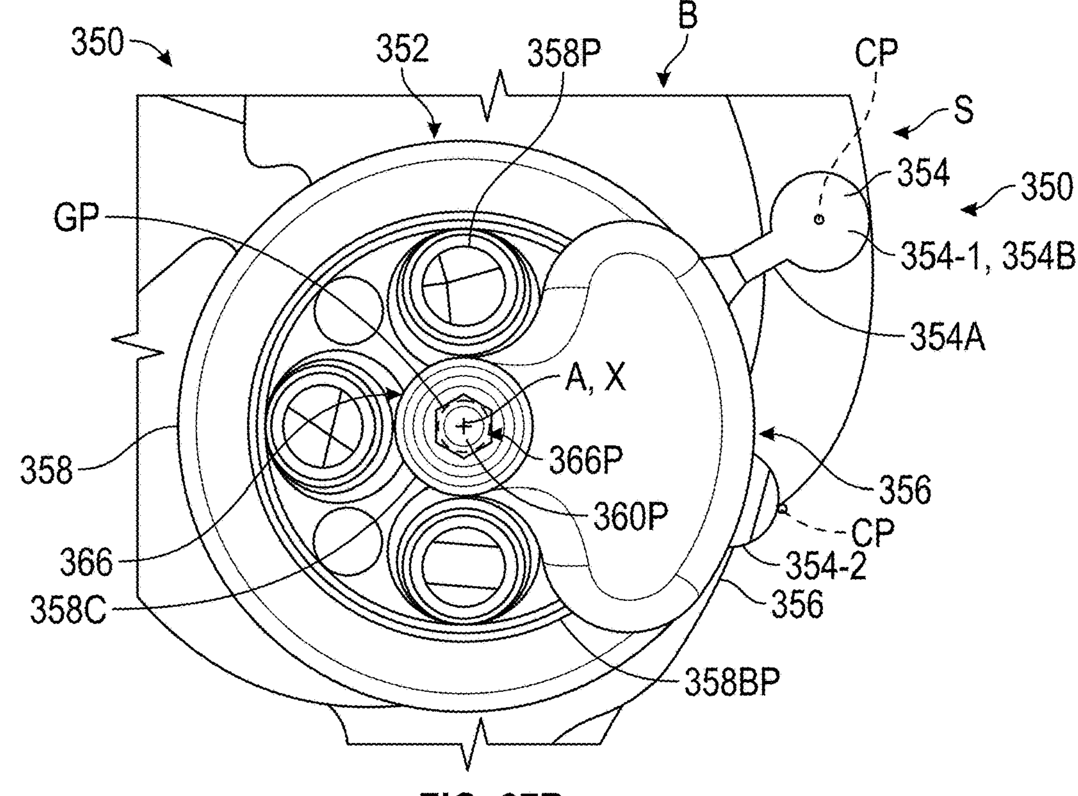
FIG. 27B illustrates an axial view of the assembly of FIG. 27A.
Figure 27C:
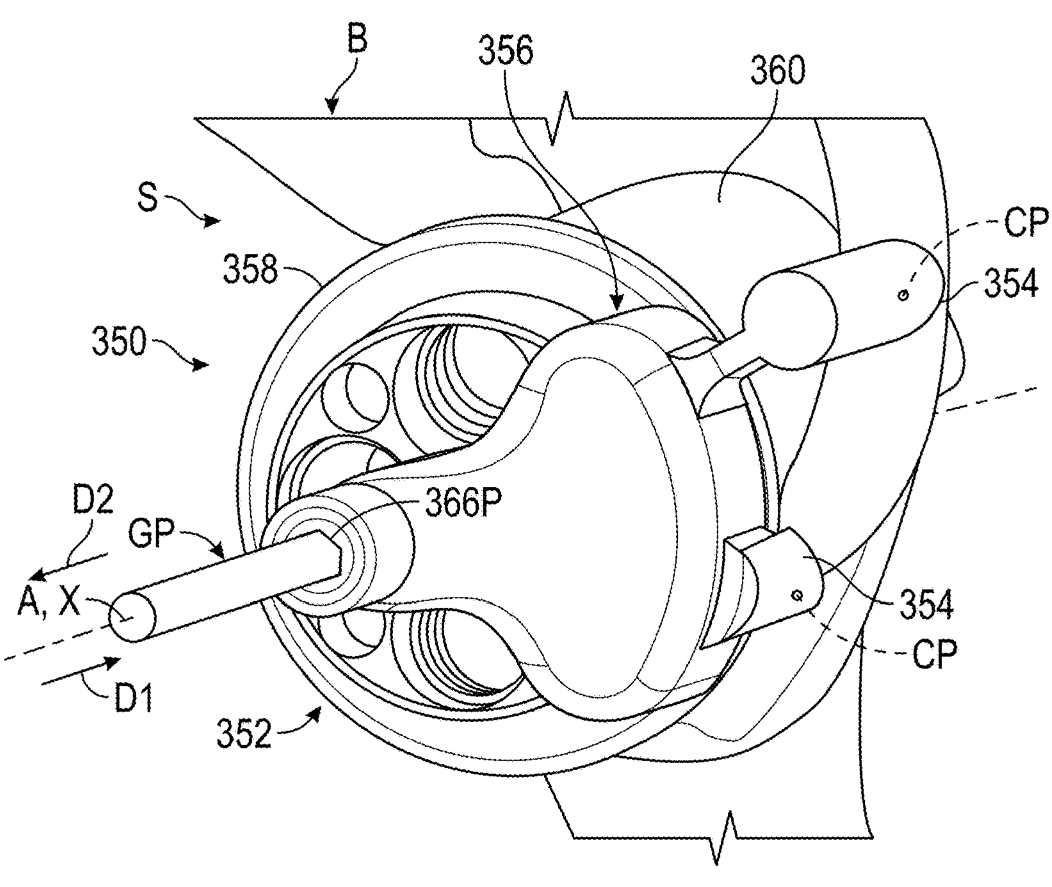
FIG. 27C illustrates a positioning object situated at the surgical site utilizing the coupling member of FIG. 27A.
Figure 27D:
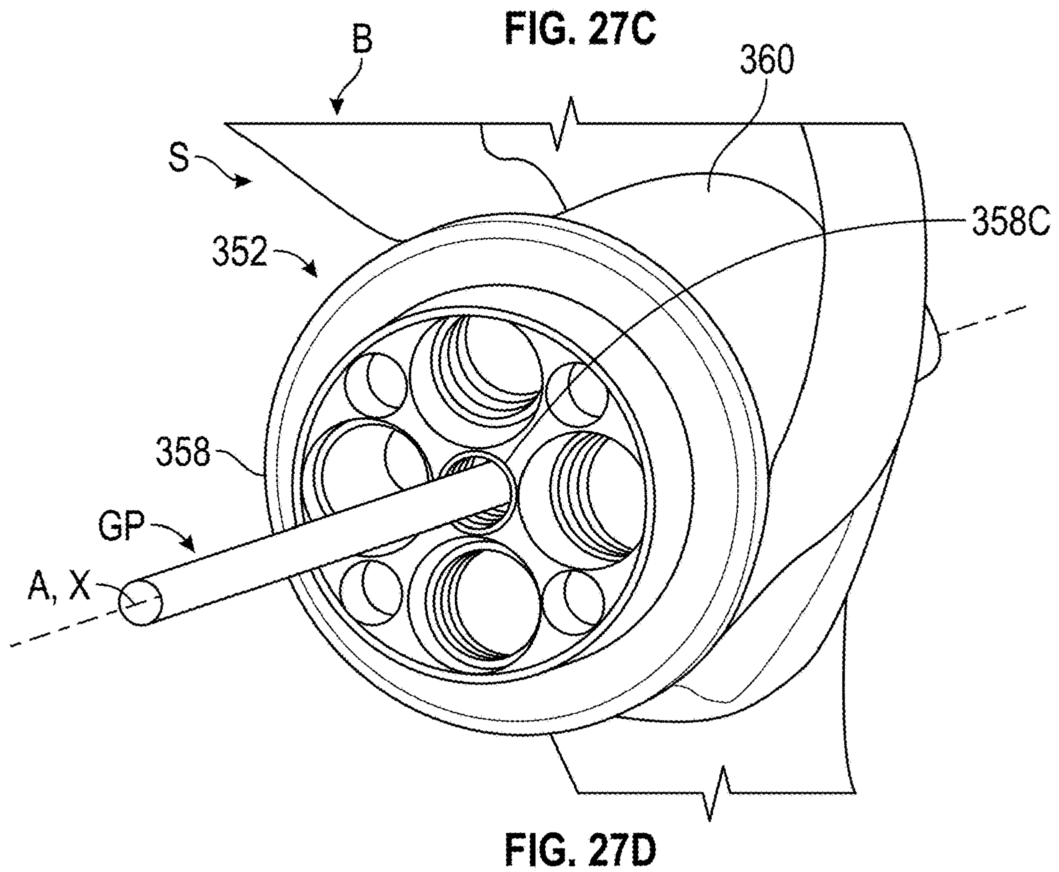
FIG. 27D illustrates the coupling member and transfer guide of FIG. 27C removed from the surgical site.
Figures 27E, 27F:
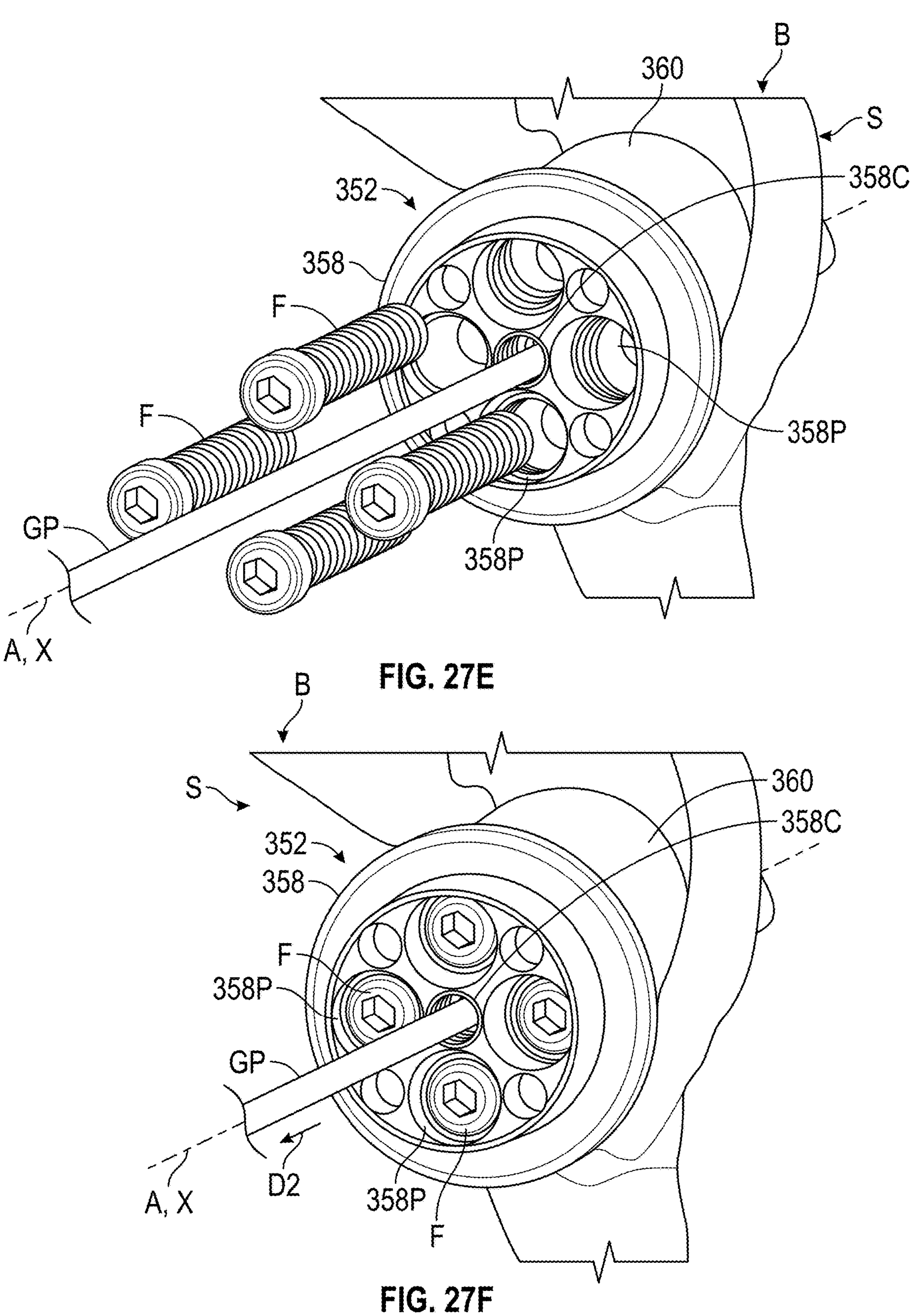
FIG. 27E illustrates fasteners positioned relative to the implant of FIG. 27D.
FIG. 27F illustrates the implant secured with the fasteners of FIG. 21E.
Figure 27G:
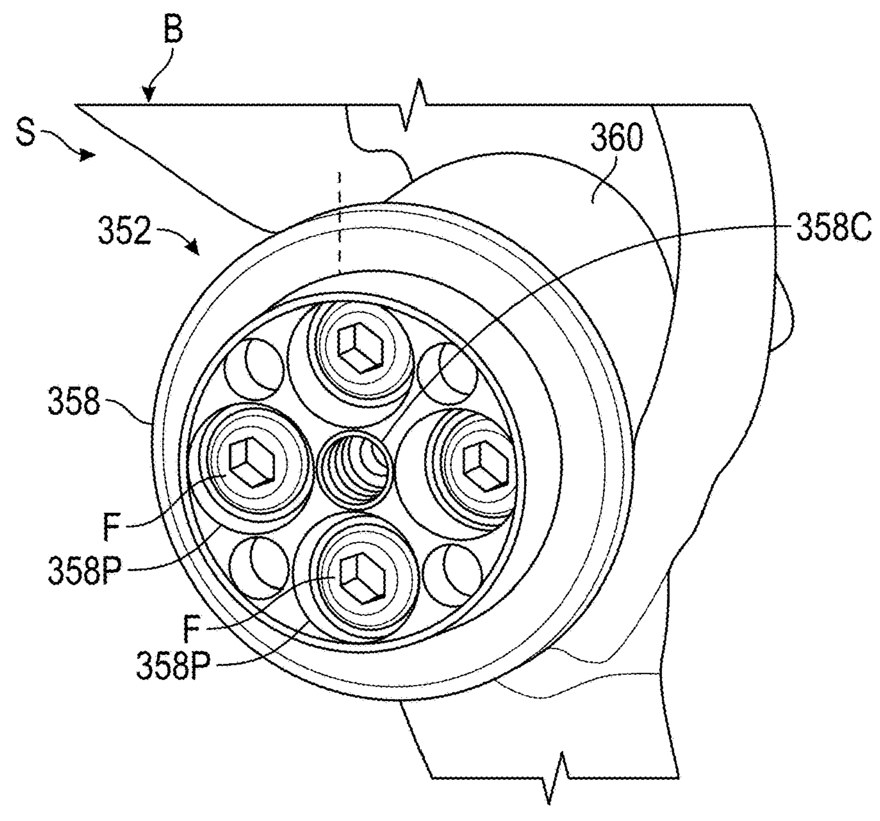
FIG. 27G the positioning object of FIG. 27F removed from the implant.

Each of the transfer members 354 may include a respective contact surface 354CS. The contact surface 354CS may extend along the terminal end portion 354T and may be dimensioned with respect to a predetermined surface contour of the bone B, as illustrated in FIG. 26. The predetermined surface contour may be associated with an articular surface of the bone B, a perimeter of the articular surface such as the glenoid rim of a patient, or another surface of the bone B. The contact surface 354CS may be dimensioned with respect to any of the techniques disclosed herein, including one or more parameters of the surgical plan 33, which may be determined at step 198G of method 198 according to respective contact points CP along the patient anatomy. The transfer members 354 may include a first transfer member 354-1 and a second transfer member 354-2. The terminal end portion 354T of the first transfer member 354-1 may have a geometry that differs from a geometry of the terminal end portion 354T of the second transfer member 354-2, including the respective the contact surfaces 354CS. The transfer members 354 may extend outwardly from the guide body 362 such that the contact surface 354CS contacts a surface contour of the bone B at the respective contact points CP. The implant 352 may be spaced apart from each of the contact points CP in response to positioning the guide pin GP in the bone B, as illustrated by FIGS. 27B-27C (guide pin GP shown in dashed lines in FIG. 27B for illustrative purposes).

FIGS. 27A-27G illustrate various states of installing the implant 352 to bone B at a surgical site S utilizing the transfer members 354 and associated transfer guide 356. The planning system 20 may be utilized to establish a surgical plan for installing the implant 352. The implant 352 may be installed utilizing any of the steps of the method 198 and/or in the same manner as the implant 252 and respective assembly 250 of FIGS. 21A-21F. The method 198 may include forming each of the contact surfaces 354CS to substantially follow the surface profile of the bone B at step 198L, which may be based on the surgical plan established at step 198J.

Figure 28:
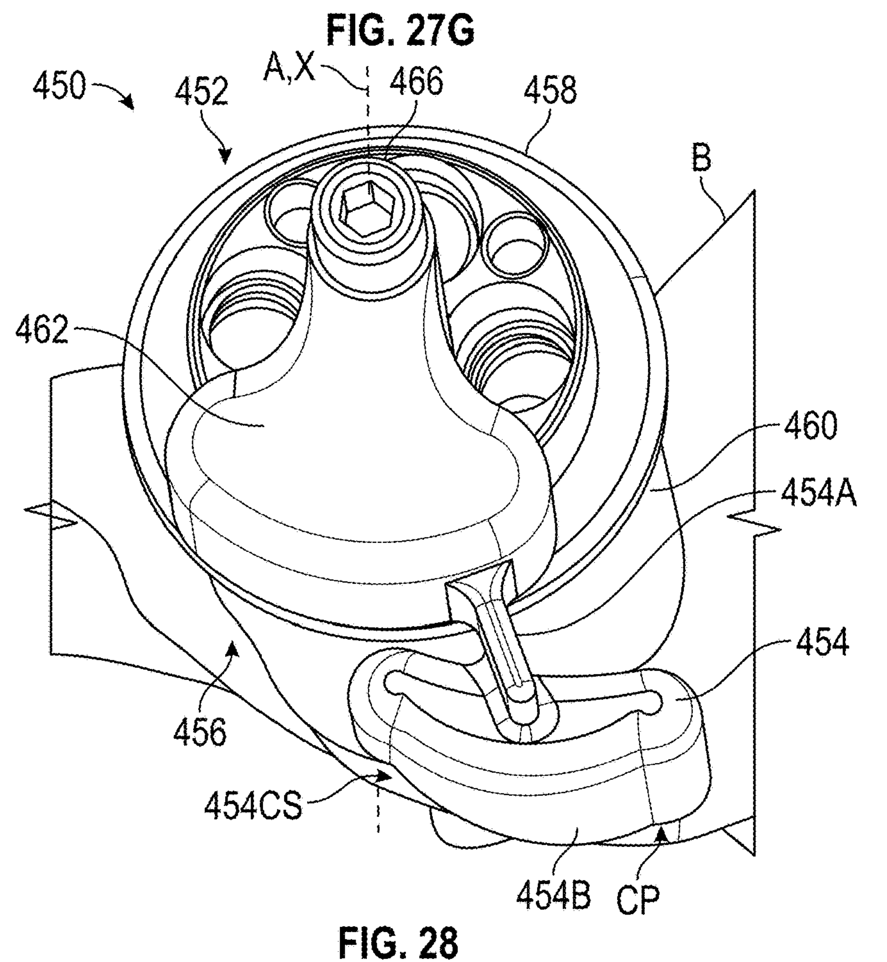
FIG. 28 illustrates another exemplary orthopaedic assembly situated at a surgical site and including an implant, transfer guide and transfer members that may have a patient-specific configuration and may incorporate a coupling member.
Figures 29, 30:
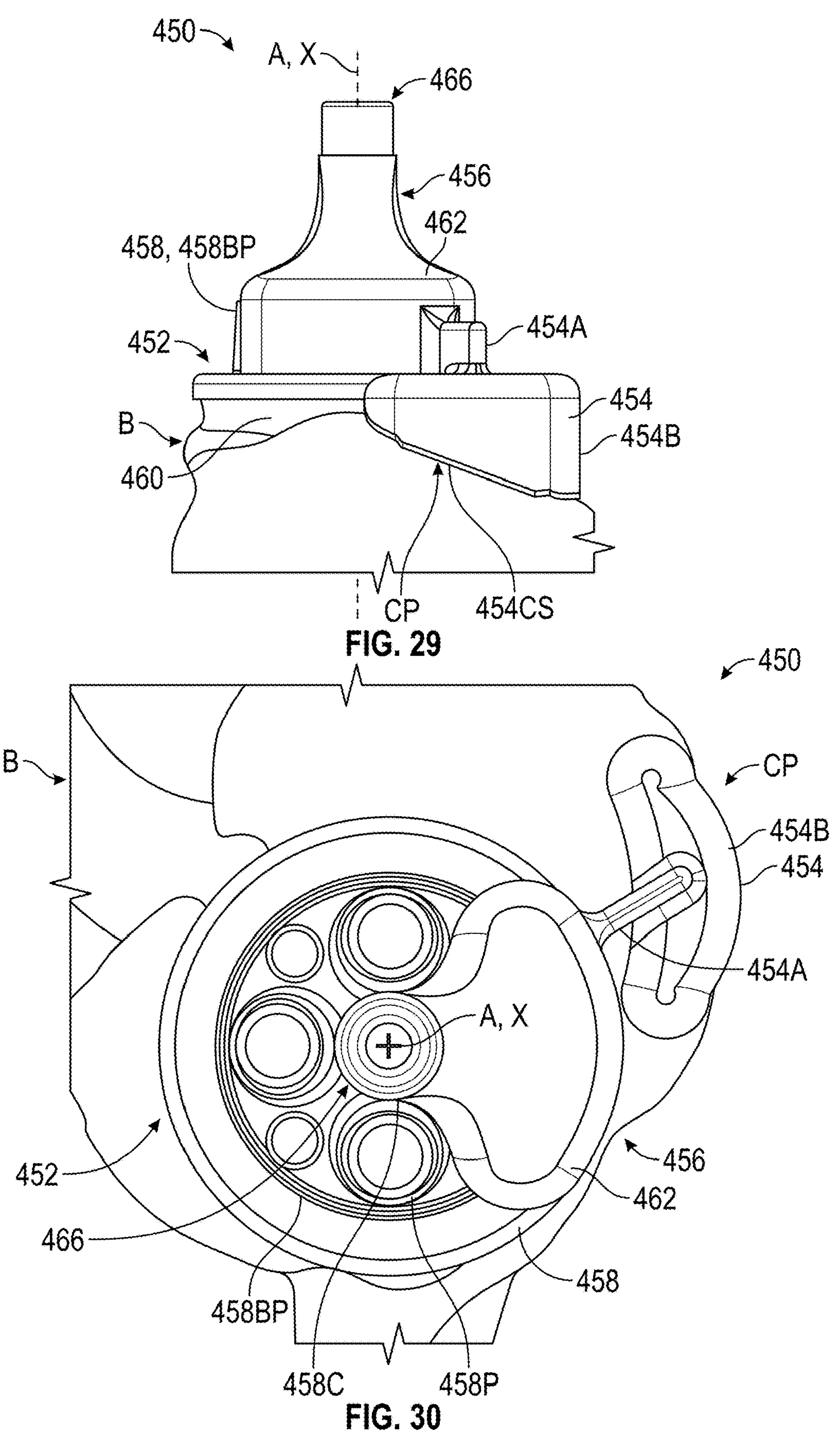
FIG. 29 illustrates a side view of the implant of FIG. 28.
FIG. 30 illustrates an axial view of the implant of FIG. 28.

The transfer members may have other geometries, as illustrated by the assembly 450 of FIGS. 28-30. The assembly 450 may include an implant 452 and a transfer guide 456. At least one transfer member 454 may extend outwardly from a guide body 462 of the transfer guide 456. The transfer member 454 may be integrally formed with the guide body 462.

The transfer member 454 may include a first portion (e.g., transfer arm) 454A and a second portion (e.g., transfer body) 454B extending from the first portion 454A. The first portion 454A may interconnect the guide body 462 and second portion 454B. The second portion 454B may be cantilevered from the first portion 454A such that the second portion 454B is spaced apart radially from the implant 352 relative to axes A, X.

The second portion 454B of the transfer member 454 may include a contact surface 454CS dimensioned to contact bone B or other tissue. The contact surface 454CS may be dimensioned with respect to a predetermined surface contour of the bone B or other tissue. In implementations, the contact surface 454CS may have a patient-specific geometry and may be dimensioned to substantially conform or follow a surface contour of the bone B associated with a respective patient at a respective contact point CP. The contact surface 454CS may be dimensioned according to a predetermined surgical plan utilizing any of the techniques disclosed herein. The implant 452 may be installed utilizing any of the steps of the method 198 and/or in the same manner as the implant 252 and respective assembly 250 of FIGS. 21A-21F.

Figure 31:
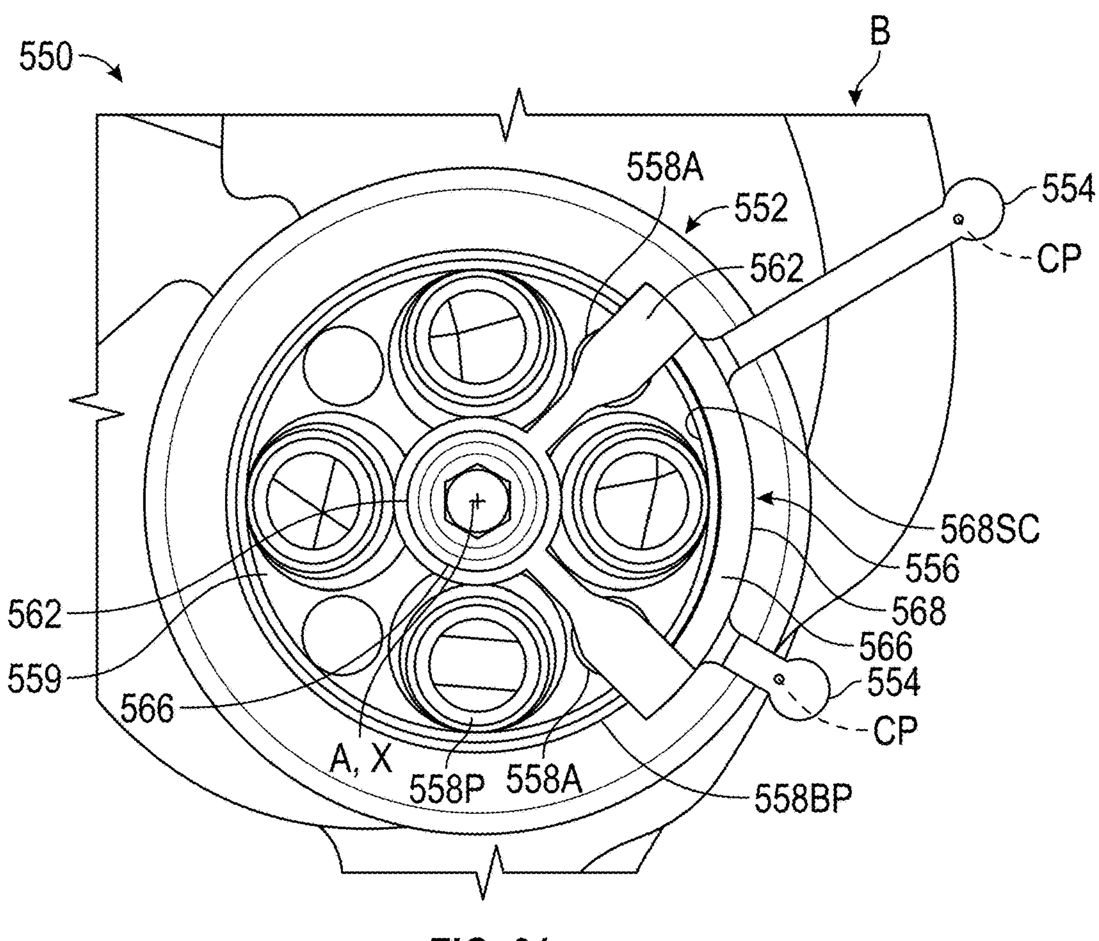
FIG. 31 illustrates another exemplary orthopaedic assembly situated at a surgical site and including an implant, transfer guide and transfer members and that may incorporate a coupling member.
Figure 32:
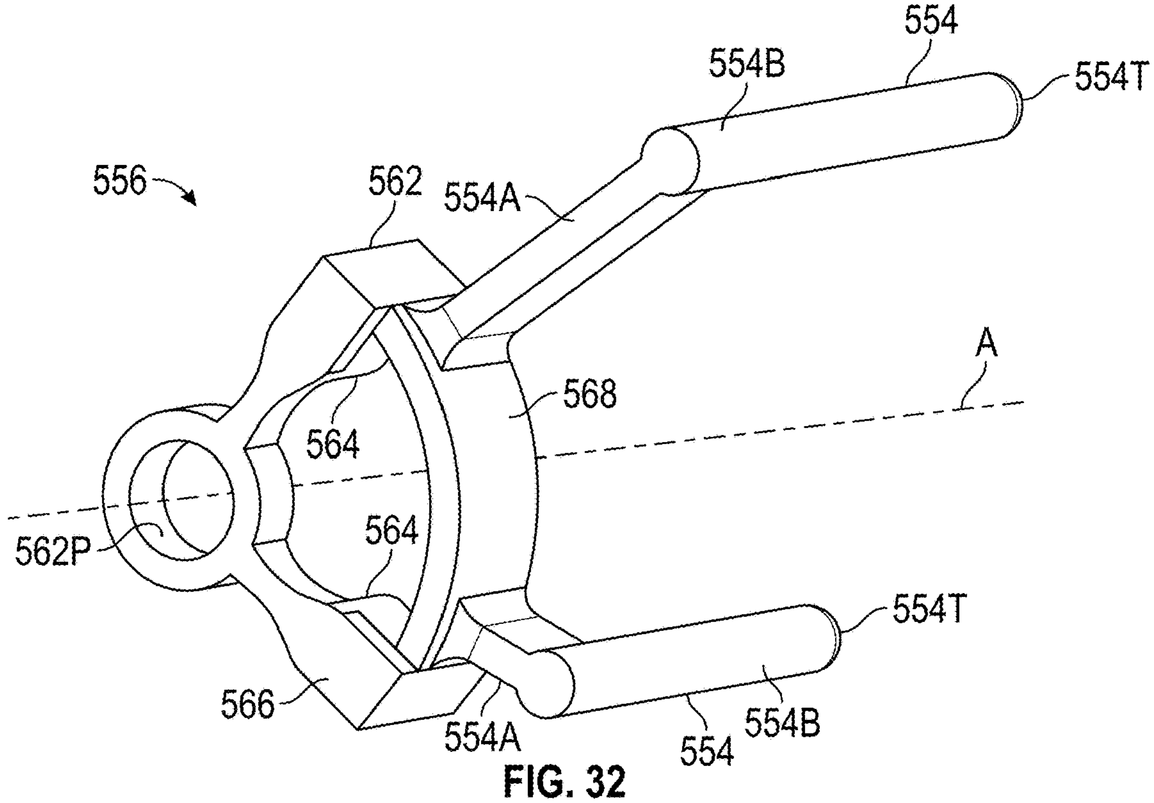
FIG. 32 illustrates a perspective view of the transfer guide of FIG. 31.
Figure 33A:
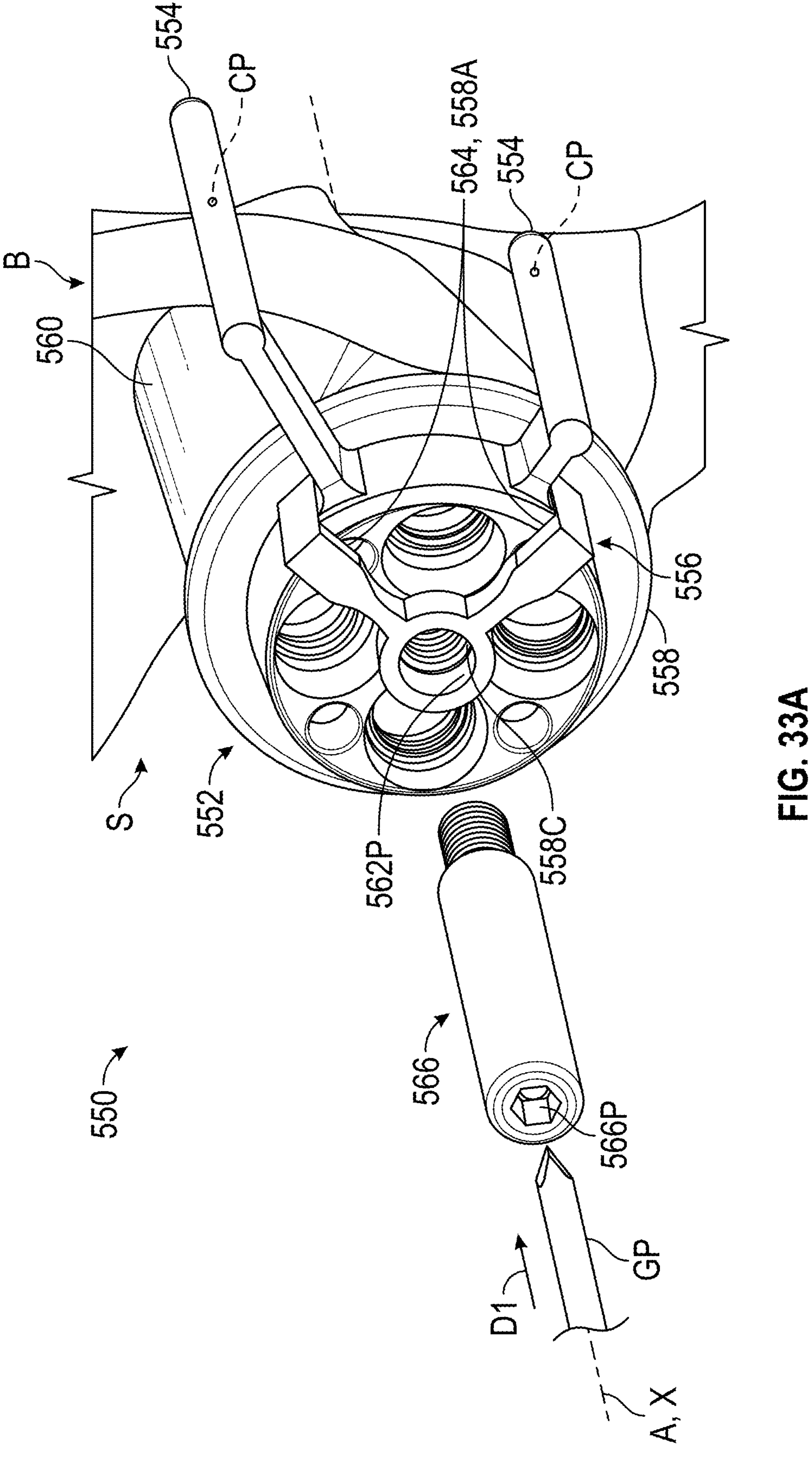
FIG. 33A illustrates the assembly of FIG. 28 including a transfer guide, coupling member and implant positioned relative to a surgical site.
Figure 33B:
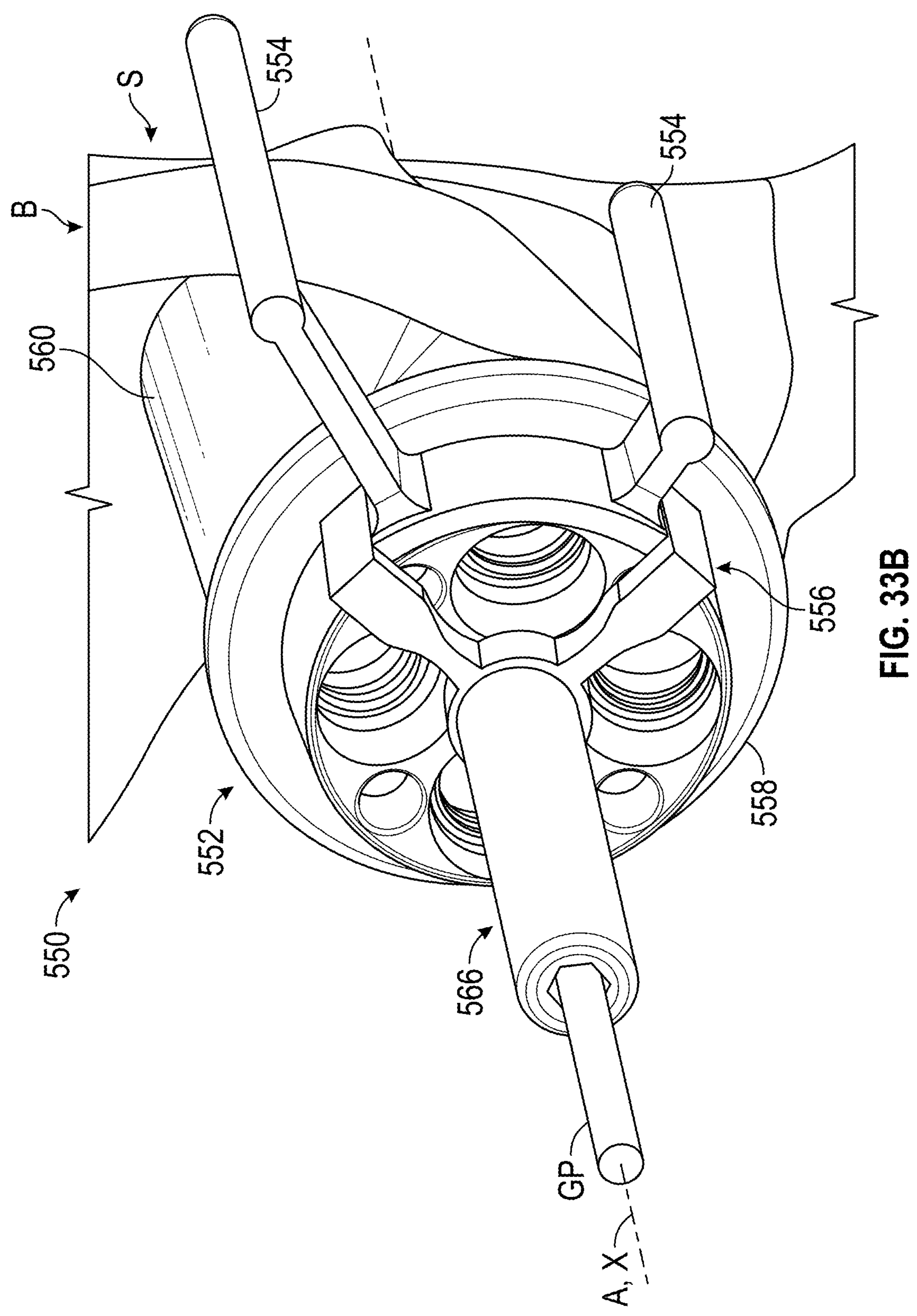
FIG. 33B illustrates a positioning object situated at the surgical site utilizing the coupling member of FIG. 33A.
Figure 33C:
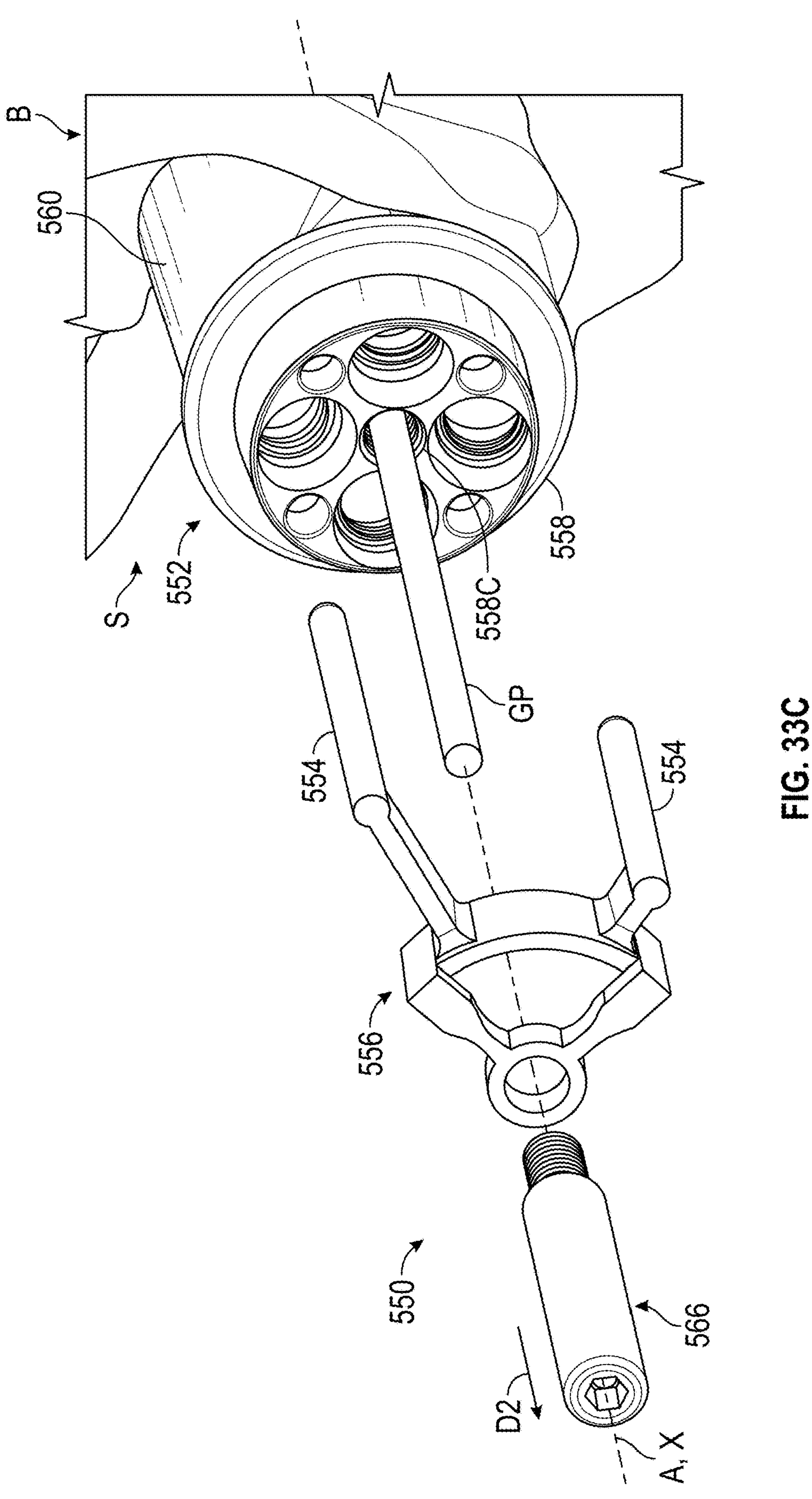
FIG. 33C illustrates the coupling member and transfer guide of FIG. 33B removed from the surgical site.
Figure 33D:
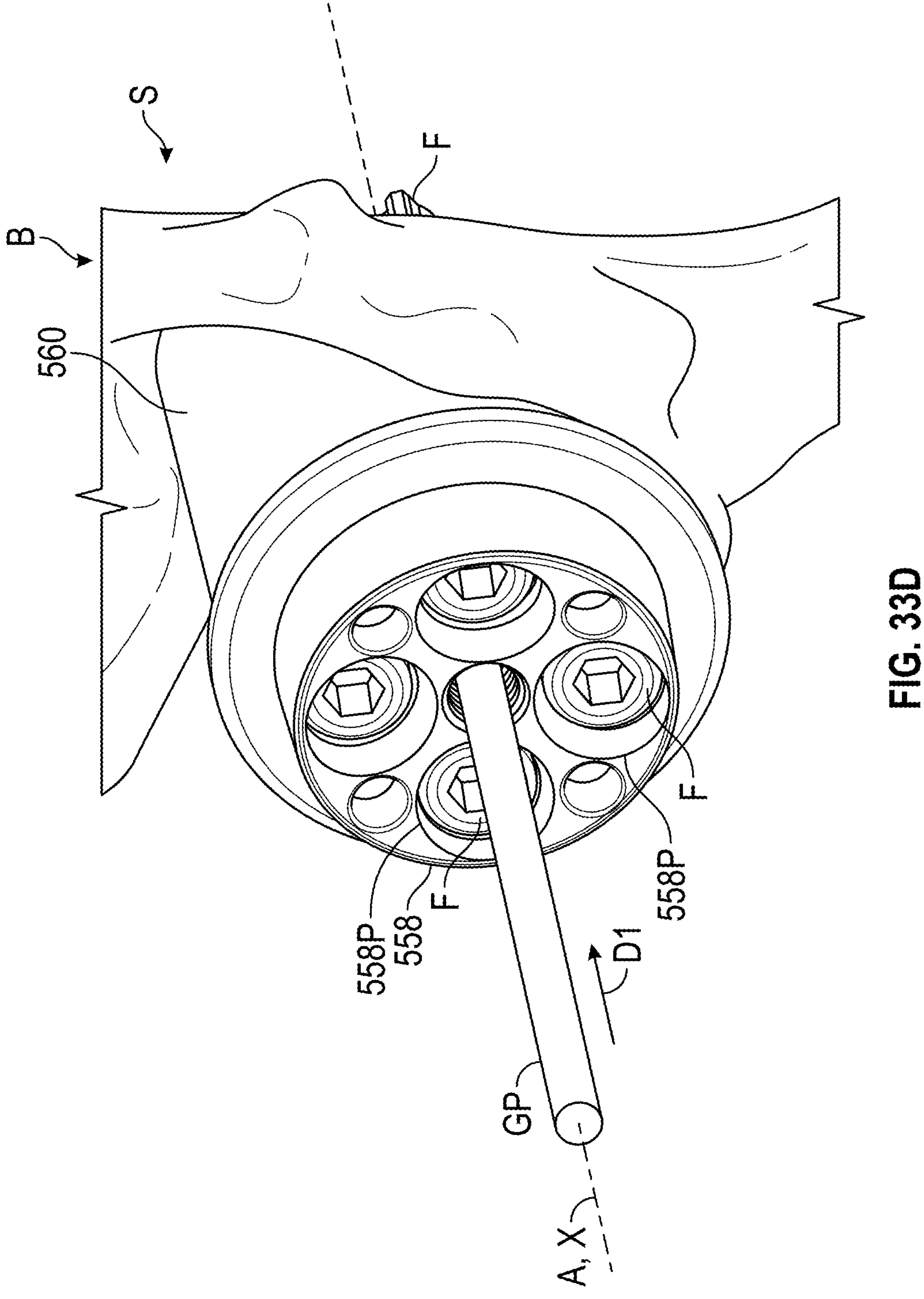
FIG. 33D illustrates the implant of FIG. 33C secured with fasteners.

The transfer members and associated transfer guide may be coupled to the implant utilizing other techniques, as illustrated by the assembly 550 of FIG. 31. The assembly 550 may include an implant 552 and a transfer guide 556. One or more transfer members 554 may extend outwardly an abutment member 568 or another portion of a guide body 562 of the transfer guide 556, as illustrated by FIGS. 31-32. The abutment member 568 may extend outwardly from the guide body 562. The abutment member 568 may have a substantially arcuate geometry and may include a surface contour 568SC dimensioned to substantially follow a periphery 558BP along the plate body 559 of the baseplate 558 to limit relative radial movement between the transfer guide 556 and implant 552 relative to the axes A, X, as illustrated in FIG. 31.

The transfer members 554 may be integrally formed with the guide body 562 and abutment member 568 of the transfer guide 556. The transfer members 554 may be dimensioned based on a predetermined surgical plan such as the surgical plan 33 (FIG. 2) utilizing any of the techniques disclosed herein. The implant 552 may be installed utilizing any of the steps of the method 198 and/or in the same manner as the implant 252 and respective assembly 250 of FIGS. 21A-21F. FIGS. 33A-33D illustrate various states of installing the implant 552 with the transfer guide 556 which may correspond to one or more steps of the method 198.

Figure 34:
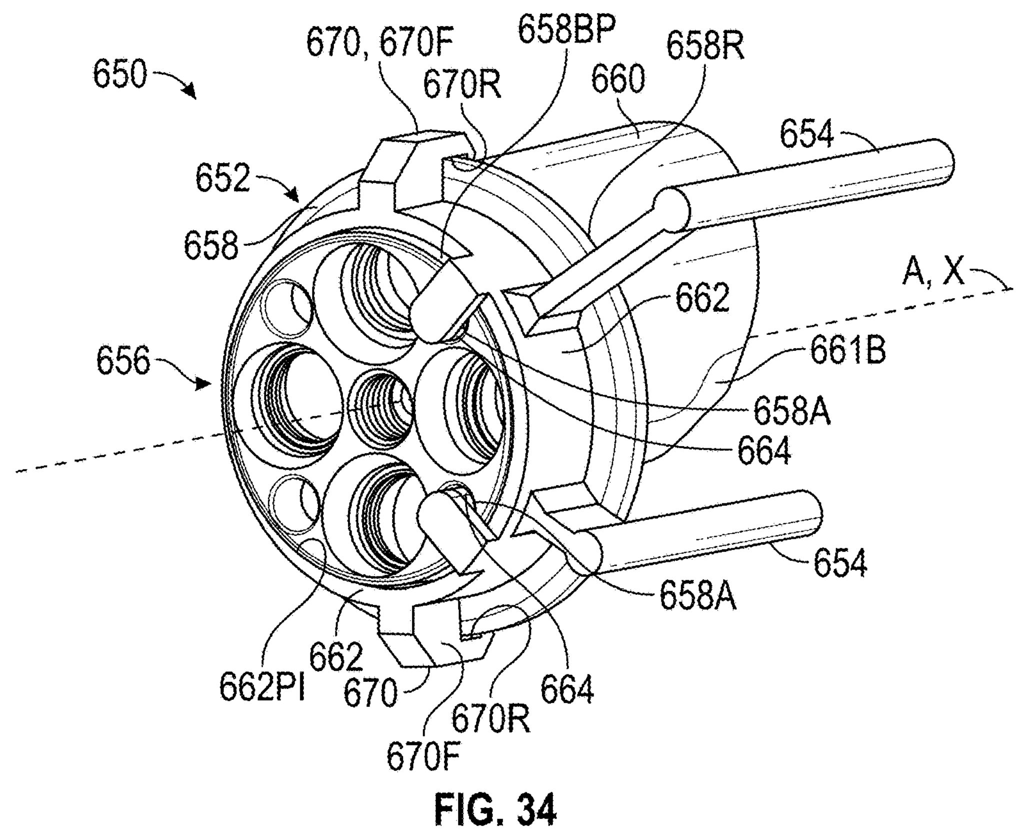
FIG. 34 illustrates another exemplary orthopaedic assembly include a transfer guide that may establish a snap-fit connection.

FIG. 34 illustrates another exemplary assembly 650 for an orthopaedic procedure. The assembly 650 may be utilized to restore functionality to any of the joints and other anatomy according to any of the techniques disclosed herein. The assembly 650 may include an orthopaedic implant 652 and one or more transfer members 654.

Figure 38A:
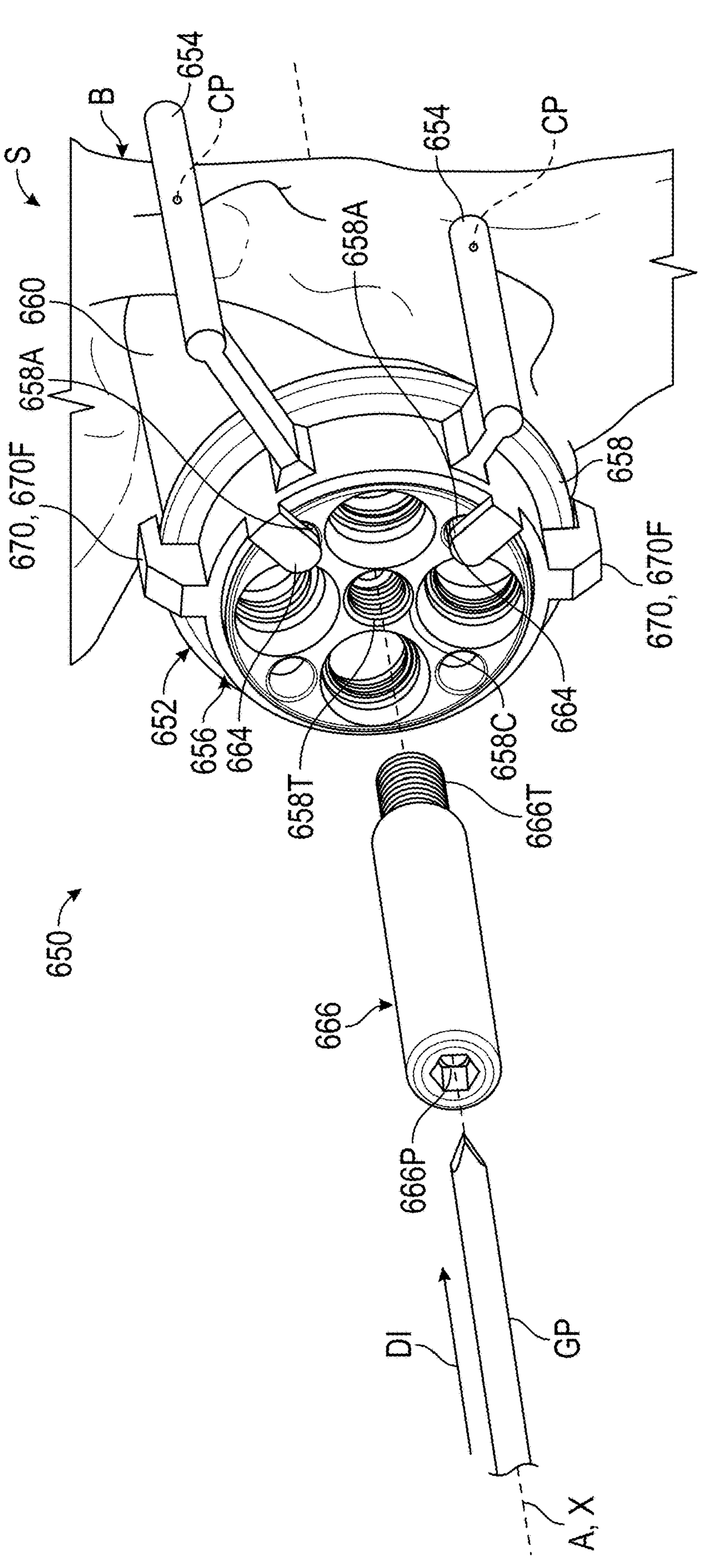
FIG. 38A illustrates the assembly of FIG. 34 including a transfer guide, positioning member and implant positioned relative to a surgical site.
Figure 38B:
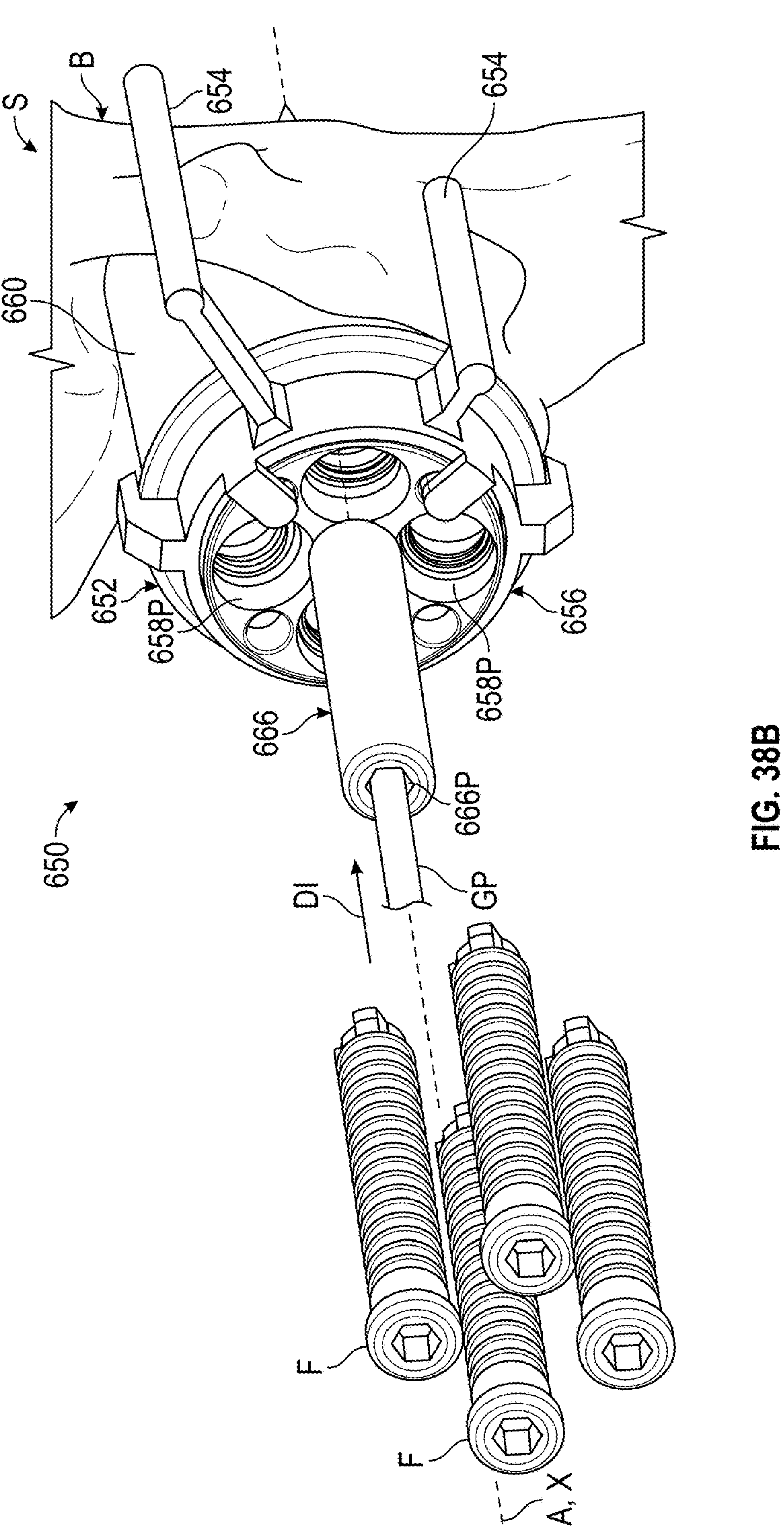
FIG. 38B illustrates fasteners and a positioning object situated at the surgical site utilizing the positioning member of FIG. 38A.
Figure 38C:
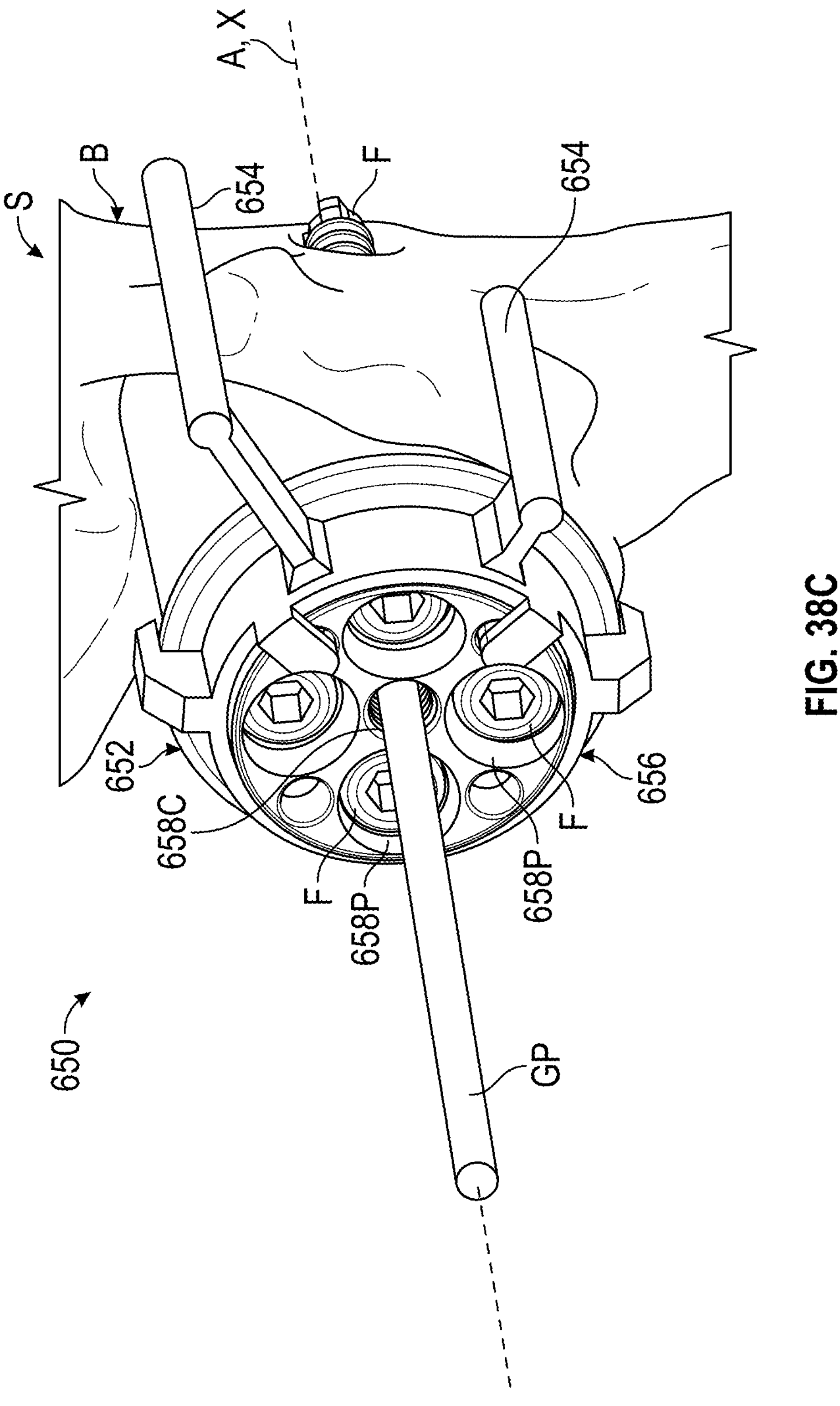
FIG. 38C illustrates the implant secured with the fasteners of FIG. 38B and the positioning member removed from the surgical site.
Figure 38D:
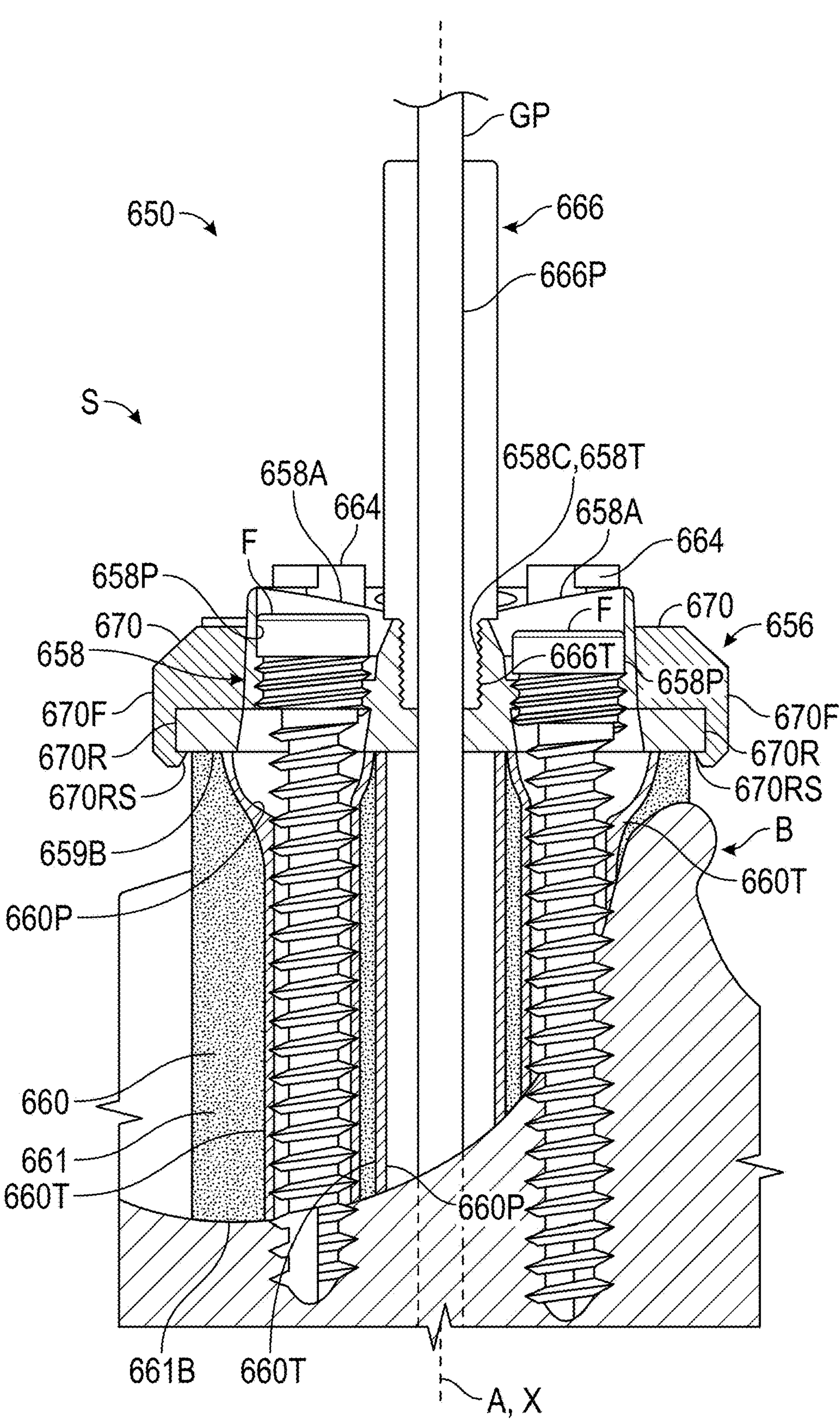
FIG. 38D illustrates a sectional view of the assembly, positioning object and fasteners of FIG. 38C and the positioning member of FIG. 38B.
Figure 38E:
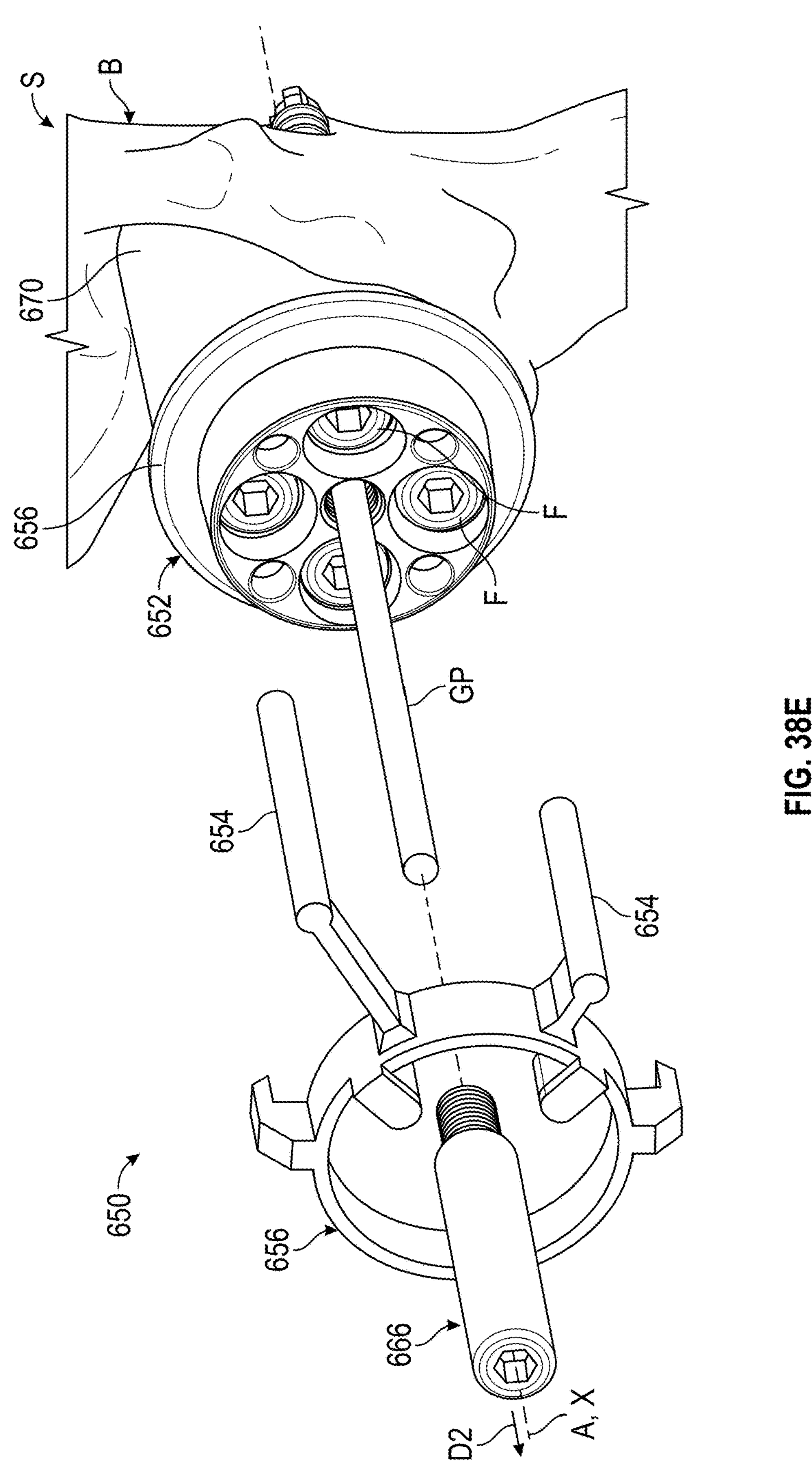
FIG. 38E illustrates the transfer guide of FIG. 38D removed from the implant.

The implant 652 may include a baseplate 658 and augment 660. The augment 660 may include a rear face 661B having a patient-specific geometry dimensioned to substantially follow a surface contour of the bone B, as illustrated in FIG. 38D.

The transfer members 654 may extend outwardly from a guide body 662 of the transfer guide 656. The transfer members 654 may be integrally formed with the guide body 662. The transfer members 654 may be positioned and dimensioned relative to the guide body 662 based on a predetermined surgical plan utilizing any of the techniques disclosed herein.

Figure 37:
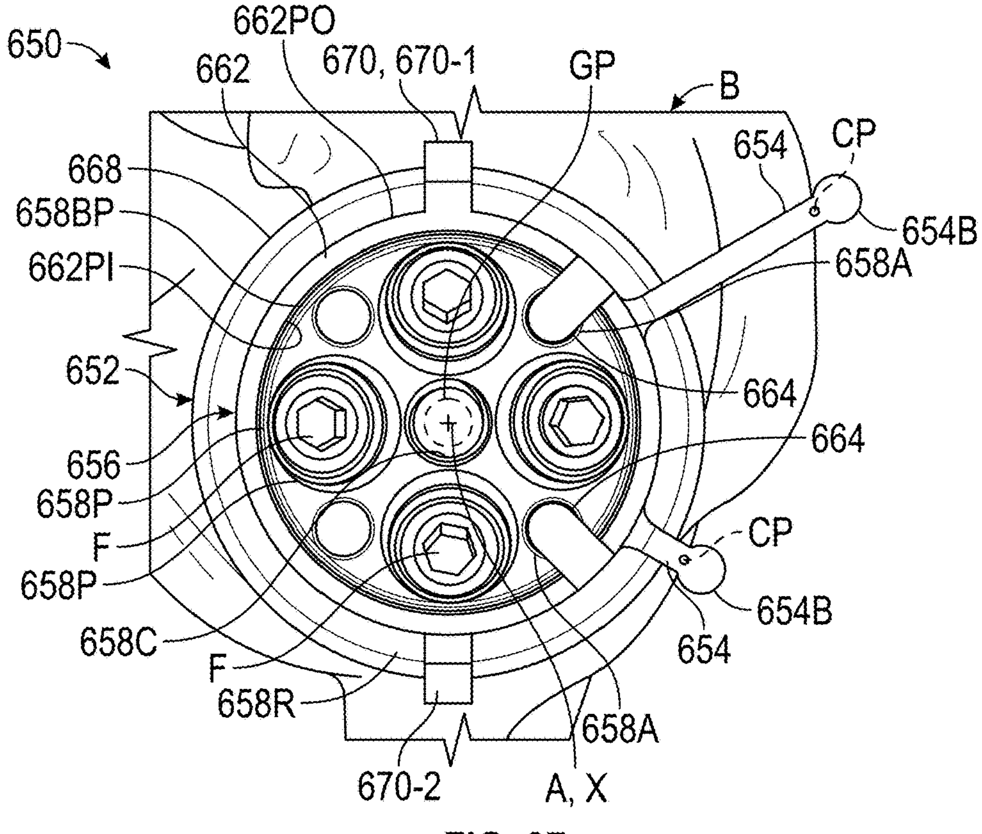
FIG. 37 illustrates an axial view of the assembly of FIG. 36.

The guide body 662 may have a substantially circular or elliptical geometry, as illustrated in FIG. 37. The guide body 662 may be dimensioned to at least partially receive a periphery 658BP of the baseplate 658. An inner periphery 662PI of the guide body 662 may be dimensioned to substantially or completely encircle a periphery 658BP of the baseplate 658.

The transfer guide 656 may include one or more alignment members 664. The alignment members 664 may extending inwardly from the guide body 662 relative to axis A. Each of the alignment members 664 may be dimensioned to be insertable into a respective aperture 658A of the baseplate 658 to limit relative rotation between the transfer guide 656 and the implant 652.

The transfer guide 656 may include one or more fixation members 670 configured to releasably secure the transfer guide 656 to the implant 652. In implementations, the fixation members 670 may be dimensioned to interface with a circumferential rim 658R of the baseplate 658 to establish a snap-fit connection. The snap-fit connection may limit at least relative axial and/or radial movement between transfer guide 656 and implant 652 relative to the axes A, X. The transfer guide 656 may include at least one pair of the fixation members 670 that are substantially circumferentially opposed to each other relative to the axis A, as illustrated by fixation members 670-1, 670-2 of FIG. 37.

Figure 35:
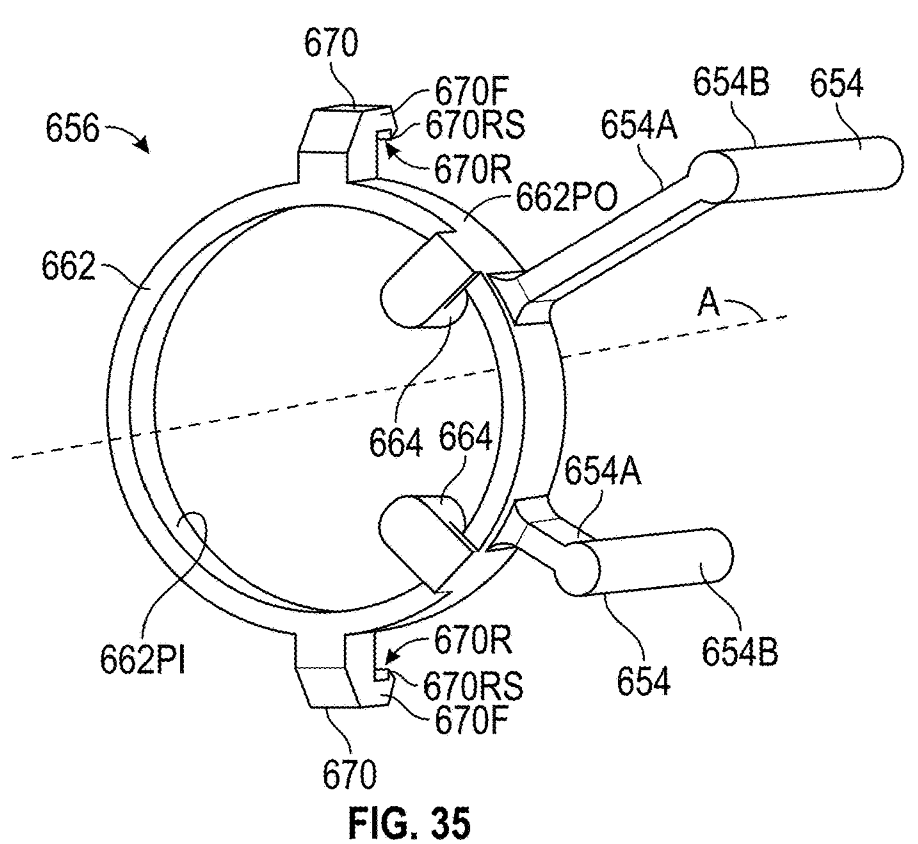
FIG. 35 illustrates a perspective view of the transfer guide of FIG. 34.
Figure 36:
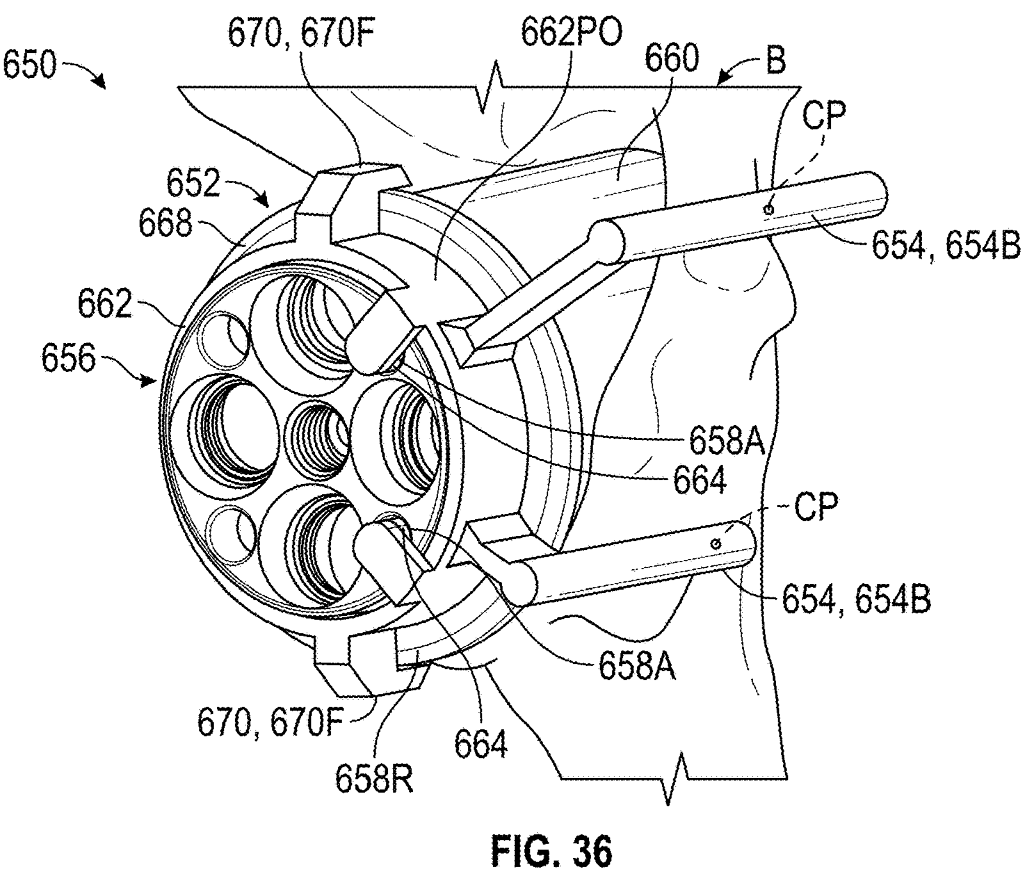
FIG. 36 illustrates a perspective view of the assembly of FIG. 34 at a surgical site.

Each of the fixation members 670 may include a flange 670F extending from an outer periphery 662PO of the guide body 662, as illustrated by FIGS. 35 and 38D. The flange 670F may have a generally C-shaped geometry dimensioned to establish a recess 670R. The recess 670R may be dimensioned to receive a portion of the circumferential rim 658R of the baseplate 658. Each of the flanges 670F may include a ramped surface 670RS dimensioned to cause the flanges 670F to deflect outwardly in response to contact with the circumferential rim 658R of the baseplate 658.

The implant 652 may be installed utilizing any of the steps of the method 198 and/or in the same manner as the implant 252 and respective assembly 250 of FIGS. 21A-21F. FIGS. 38A-33E illustrate various states of installing the implant 652 with the transfer guide 656 which may correspond to one or more steps of the method 198.

Coupling the transfer members 654 and associated transfer guide 656 to the implant 652 at step 198P may include positioning the fixation members 670 relative to the implant 652 to establish a snap-fit connection.

A coupling member (e.g., positioning member) 666 may be utilized to position one or more positioning objects such as a guide pin GP, as illustrated in FIG. 38A. Step 198P may include mating threads 666T disposed along the coupling member 666 and with threads 658T disposed along the central aperture 658C of the baseplate 658 to mechanically attach or otherwise secure the coupling member 666 to the implant 652, as illustrated in FIG. 38D. The coupling member 666 is omitted in FIG. 38C for illustrative purposes.

FIGS. 39-42 illustrate another exemplary assembly 750 for an orthopaedic procedure. The assembly 750 may be utilized to restore functionality to any of the joints and other anatomy according to any of the techniques disclosed herein. The assembly 750 may include an orthopaedic implant 752 and one or more transfer members 754 coupled to the implant 752. The implant 752 may include a baseplate 758 and augment 760 extending outwardly form the baseplate 758. The augment 760 may be dimensioned to contact bone or other tissue. The assembly 750 may omit a separate transfer guide, which may reduce a complexity in preparing for and performing a surgical procedure according to a predetermined surgical plan, such as reducing separate instrumentation and packaging.

Figures 47A, 47B, 47C, 47D:
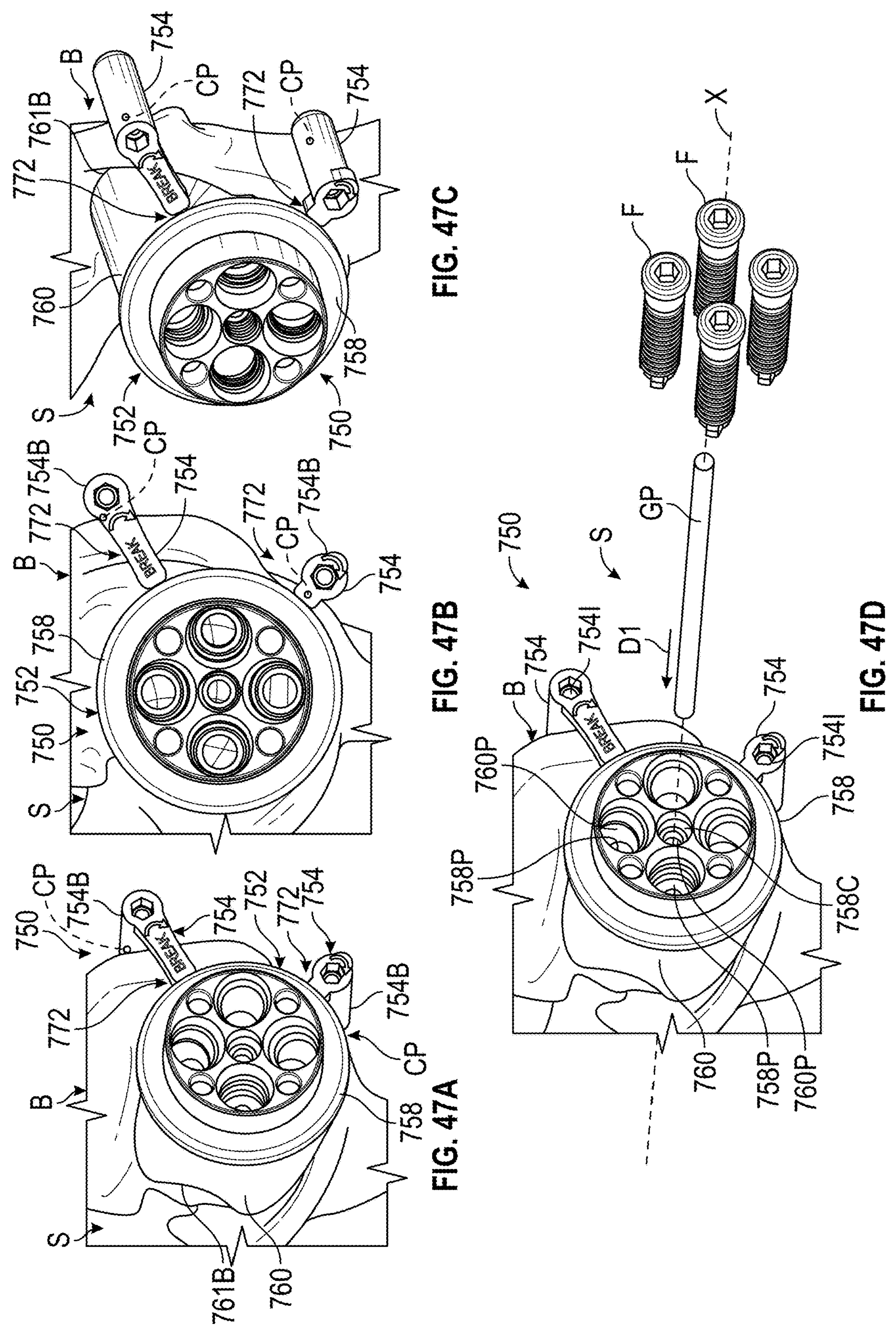
FIG. 47A illustrates a perspective view of the assembly of FIG. 39 including an implant and transfer members positioned relative to a surgical site.
FIG. 47B illustrates an axial view of the assembly of FIG. 47A.
FIG. 47C illustrates another perspective view of the assembly of FIG. 47A.
FIG. 47D illustrates a positioning object and fasteners situated relative to the assembly of FIG. 47A.

The implant 752 and each transfer member 754 may be configured to abut or contact bone B or other tissue (see, e.g., FIG. 47A). The transfer members 754 may be dimensioned according to a predetermined surgical plan to establish a predetermined position and/or predetermined orientation of the implant 752 relative to bone or other tissue at a surgical site. The implant 752 and each transfer member 754 may be dimensioned utilizing any of the techniques disclosed herein, including dimensioning the transfer members 754 and/or implant 752 based on a predetermined surgical plan established by the planning system 20 and/or method 198.

Various techniques may be utilized to secure the transfer members 754 to the implant 752, including any of the techniques disclosed herein. The transfer members 754 may be attached to or integrally formed with a main body 757 of the implant 752. In implementations, each of the transfer members 754 may be integrally formed with an augment body 761 of the augment 760 such that a position of each of the transfer members 654 is fixed relative to the augment body 761.

Figure 40:
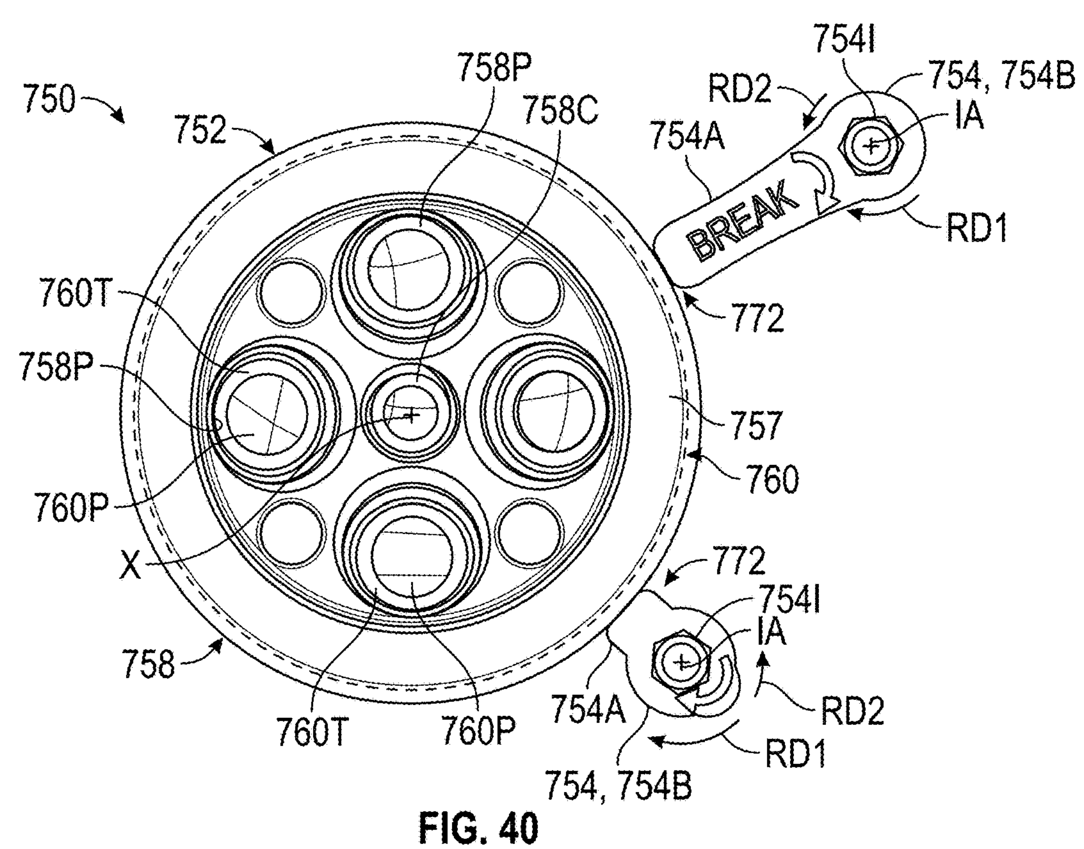
FIG. 40 illustrates an axial view of the assembly of FIG. 39.

The transfer members 754 may be dimensioned to extend outwardly from the augment body 761 or another portion of the implant 752 such as the baseplate 758. The transfer members 754 may be circumferentially distributed about a periphery of the augment 760 relative to the axis X, as illustrated in FIG. 40 (augment 760 shown in dashed lines for illustrative purposes). The transfer members 754 may be positioned relative to the main body 757 of the implant 752 including the augment body 761 based on one or more dimensions associated with a predetermined surgical plan.

Each of the transfer members 754 may include a first portion 754A and a second portion 754B. The first portion 754A may extend radially outward from a periphery of the augment body 761 relative to the axis X. The second portion 754B may extend axially between the first portion 754A and a terminal end portion 754T relative to the axis X. The terminal end portion 754T and/or another surface of the second portion 754B may be configured to abut bone B or other tissue adjacent the implant 752, as illustrated in FIG. 47A. A surgeon or user may position the implant 752 based on a position of the transfer members 754 relative to the bone B such that the implant 752 is set at a fixed position and orientation specified in a predetermined surgical plan.

Various techniques may be utilized to couple the transfer members 754 to the implant 752. Each of the transfer members 754 may be coupled to the augment 760 or another portion of the implant 752, such as the baseplate 758, at a respective breakable (e.g., frangible or severable) connection 772. Various techniques may be utilized to establish the breakable connection 772.

Figure 39:
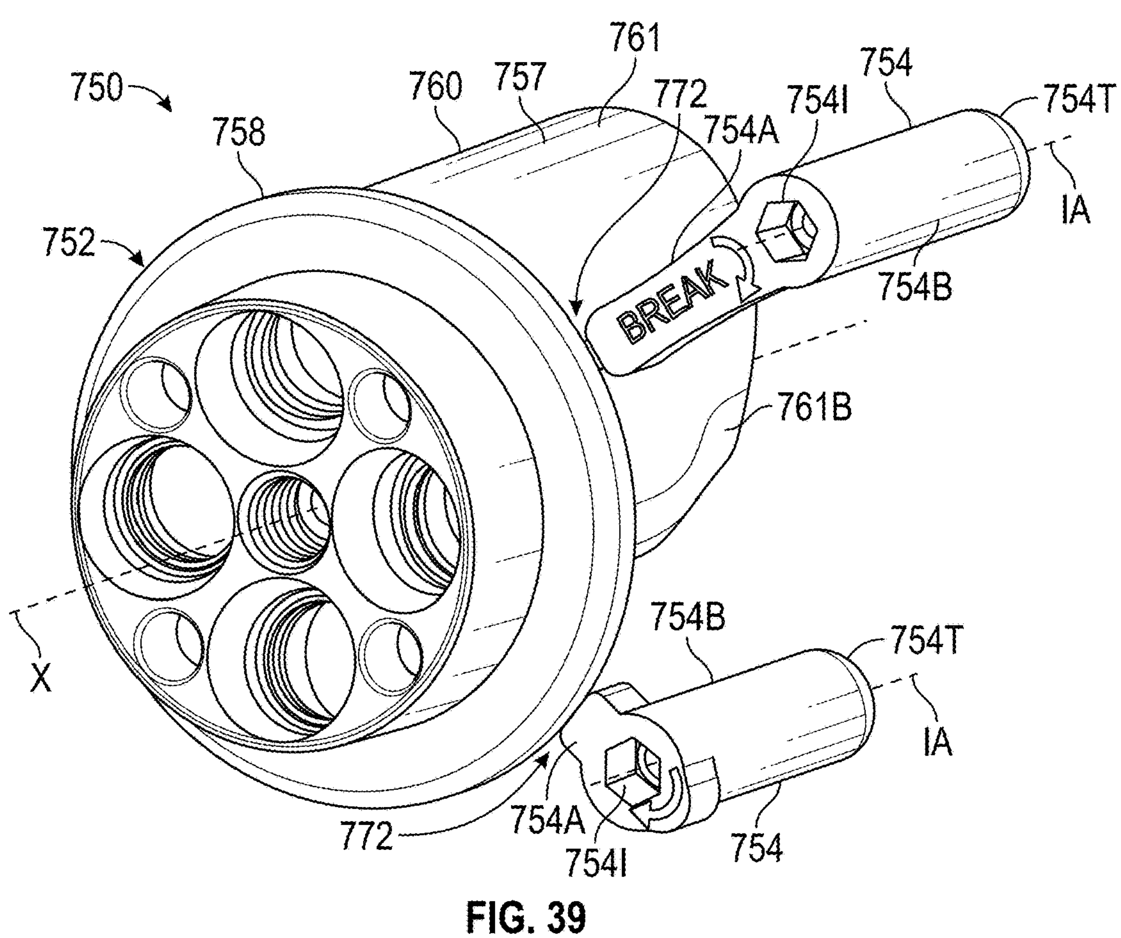
FIG. 39 illustrates another exemplary orthopaedic assembly including an implant and transfer members that may be coupled to the implant by one or more breakable connections.
Figure 41:
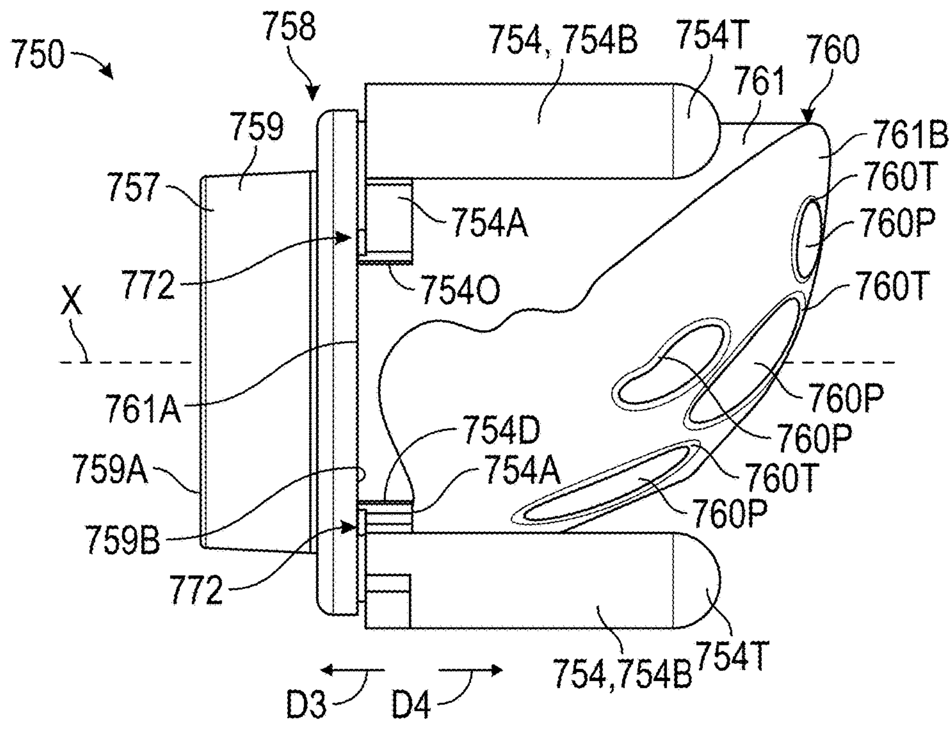
FIG. 41 illustrates a side view of the assembly of FIG. 39.
Figure 42:
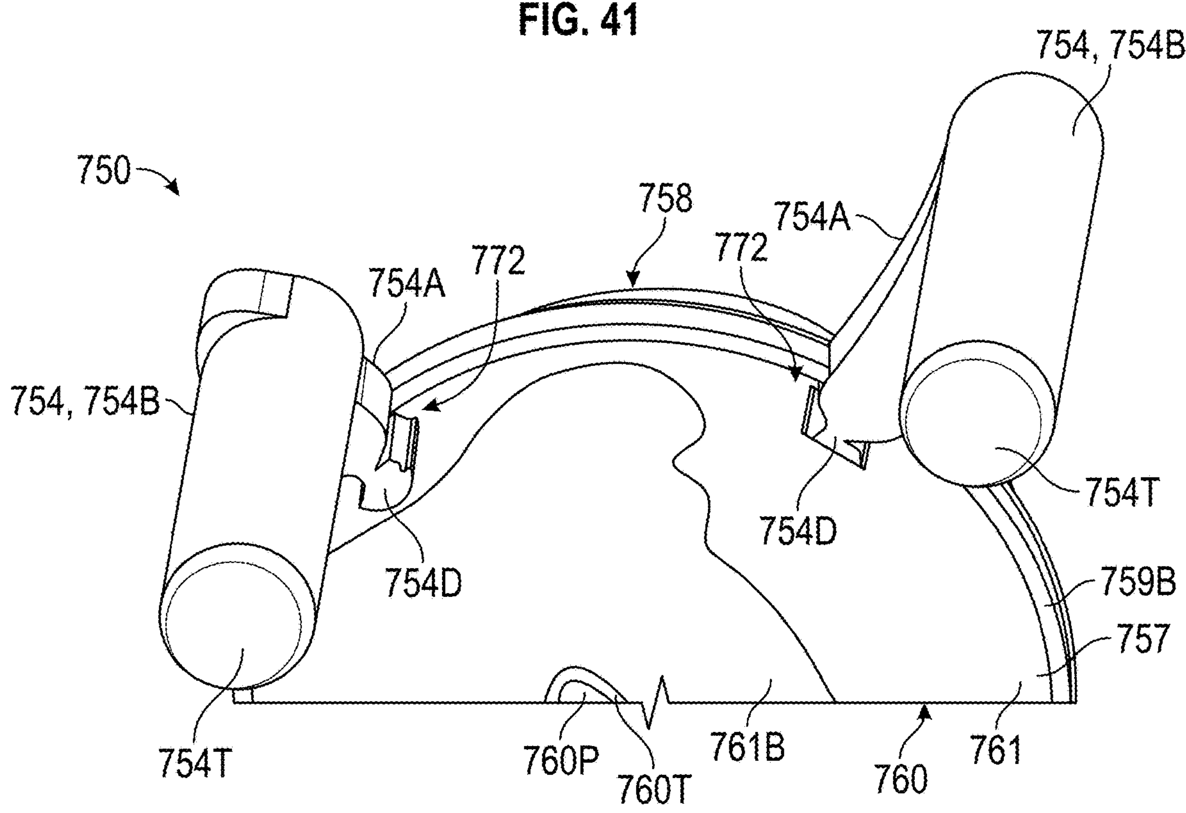
FIG. 42 illustrates a perspective view of portions of the assembly of FIG. 39.
Figure 43:
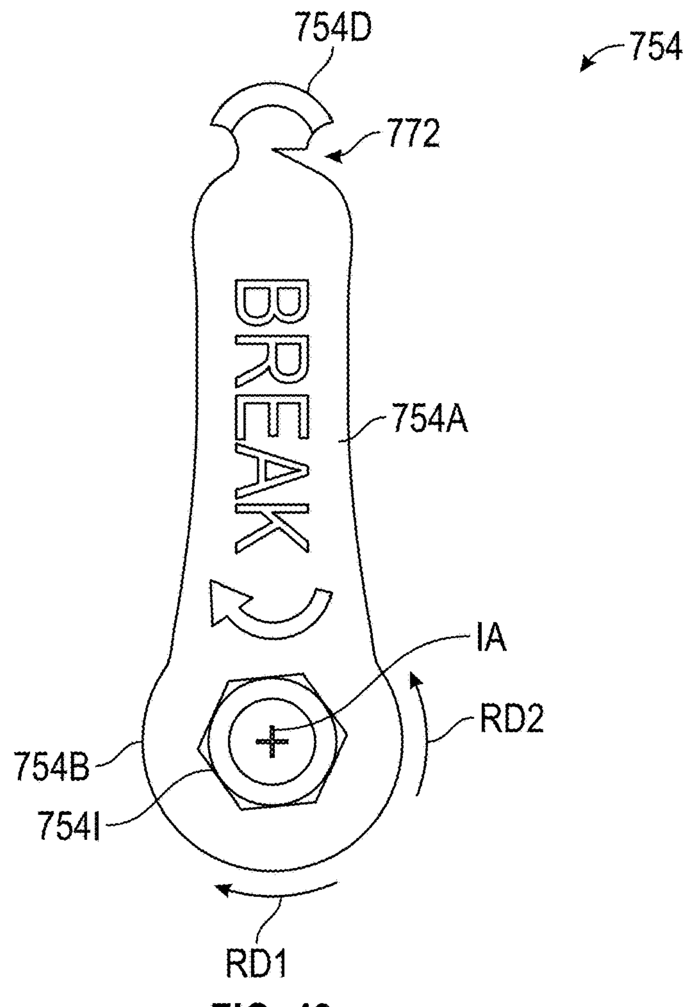
FIG. 43 illustrates a plan view of a transfer member.
Figure 44:
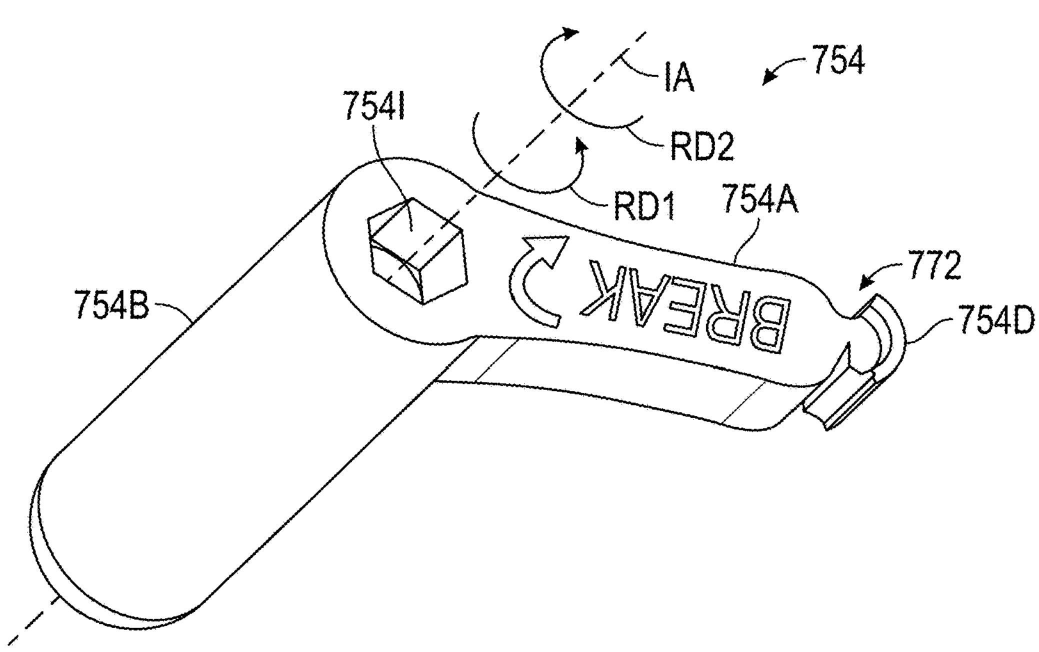
FIG. 44 illustrates a perspective view of the transfer member of FIG. 43.

Referring to FIGS. 41-44, with continuing reference to FIGS. 39-40, each transfer member 754 may include a base portion 754D extending from the first portion 754A to establish the breakable connection 772. The base portion 754D may be coupled to the augment 760 or another portion of the main body 757 of the implant 752, as illustrated in FIGS. 41-42. The first portion 754A and base portion 754D may be joined together at a reduced thickness region, such as a notch or scoring, to establish the breakable connection 772. The breakable connection 772 may be established such that the base portion 754D is positioned inwardly of an outer periphery of the baseplate 758, as illustrated in FIG. 42, which may reduce interaction between the base portion 754D and surrounding tissue subsequent to severing the breakable connection 772.

Figure 47E:
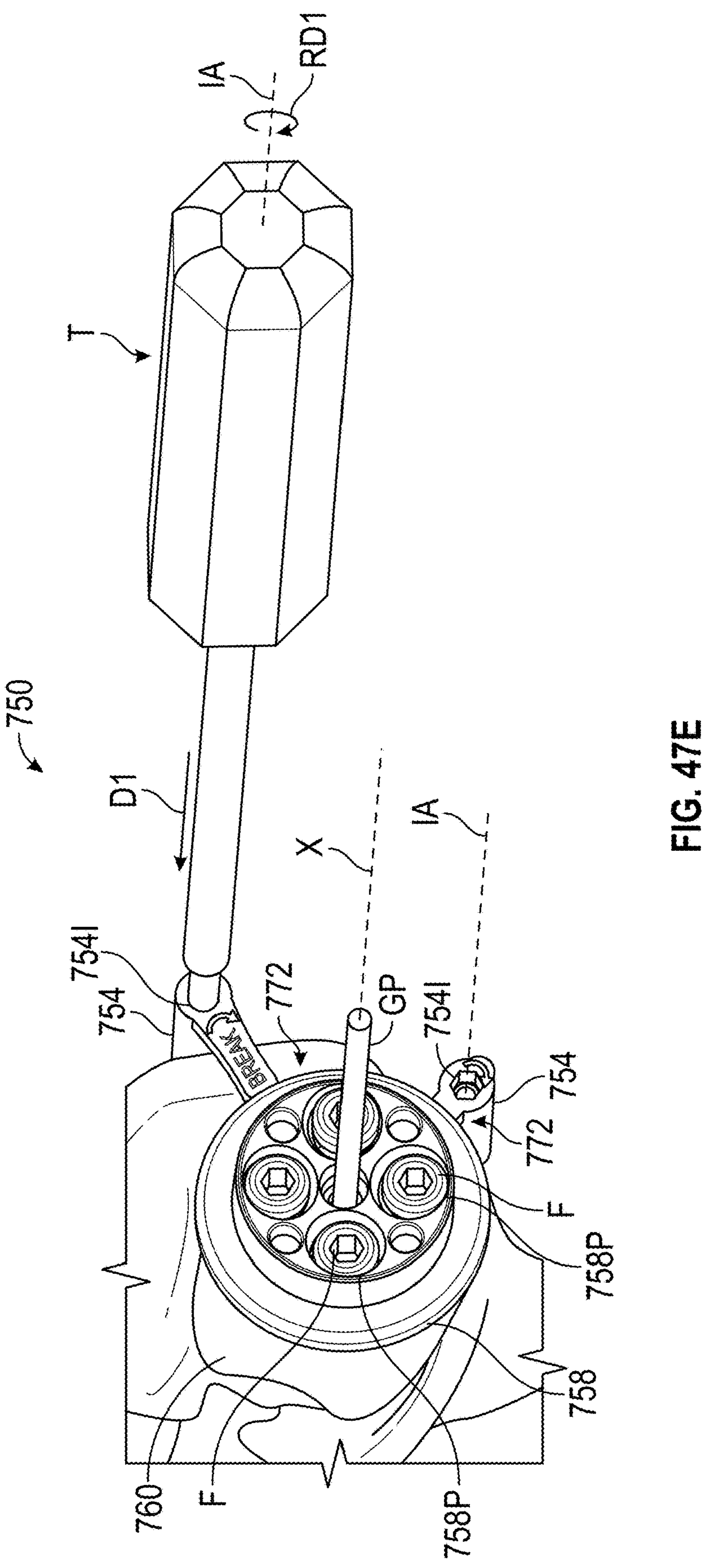
FIG. 47E illustrates the implant secured with the fasteners of FIG. 47D and tooling positioned relative to one of the transfer members.

Each transfer member 754 may include an interface 754I (FIGS. 39-40 and 43-44). The interface 754I may be dimensioned to engage tooling T, as illustrated in FIG. 47E. An interface axis IA may extend through the interface 754I. The second portion 754B may be dimensioned to extend along the interface axis IA.

The breakable connection 772 may be configured to sever in response to a predetermined quantity of torque or force at the interface 754I. The predetermined quantity of torque or force may be determined utilizing the planning system 20 and/or method 198, such as during configuring the transfer members 754 at step 198K. In implementations, the breakable connection 772 may be configured to sever in response to the predetermined quantity of torque in a first rotational direction RD1 (e.g., clockwise) about the interface axis IA, but not a second rotational direction RD2 (e.g., counter-clockwise) about the interface axis IA. The second rotational direction RD2 may be opposed to the first rotational direction RD1. In other implementations, the breakable connection 772 may be configured to sever in response to the predetermined quantity of torque in the first rotational direction RD1 and/or second rotational direction RD2. The first rotational direction RD1 of each of the transfer members 754 may be the same or may differ from each other. The transfer members 754 may include indicia that indicate the first rotational direction RD1, such as an arrow or other directional indicator.

In implementations, the breakable connection 772 may be configured to sever in response to movement of the second portion 754B of the transfer member 754 in a third direction D3 and/or a fourth direction D4 relative to axis X (FIG. 41). The third direction D3 may be in a direction generally towards the baseplate 658, and the fourth direction D4 may be in a direction generally away from the baseplate 658. A severed state of the breakable connections 722' is illustrated by the assembly 750' of FIGS. 45-46.

FIGS. 47A-47F illustrate various states of installing the implant 752 to bone B at a surgical site S utilizing the transfer members 754. The planning system 20 and any of the steps of the method 198 may be utilized to install the implant 752. The bone B may be a portion of any of the joints and patient anatomy disclosed herein, such as a portion of a glenoid.

Referring to FIG. 14, the transfer members 754 may be configured at step 198K. Step 198K may include integrally forming the transfer members 754 with the implant 652 based on one or more dimensions and other parameters established at step 198G subsequent to establishing the surgical plan at step 198J. Each of the transfer members 754 may be coupled to the implant 752 at a respective breakable connection 772.

Referring to FIGS. 47A-47C, with reference to the method 198 of FIG. 14, the implant 752 may be positioned according to the transfer members 754 at step 198O. Positioning the implant 752 may occur such that the rear face 761B or another surface of the augment 760 contacts the bone B or other tissue at the surgical site S. Step 198O may occur such that the rear face 761B of the augment 760 substantially follows a surface contour of the bone B (see, e.g., FIGS. 47A and 47C) based on a predetermined surgical plan, which may be established or updated at step 198J. The implant 752 may be positioned such that a portion of the transfer members 754 may overhang a periphery of the bone B, as illustrated in FIG. 47C.

Referring to FIG. 47D, with continuing reference to FIG. 14, at step 198Q, one or more positioning objects such as a guide pin GP may be positioned to establish a predetermined position and/or orientation of the implant 752 based on the predetermined surgical plan. The guide pin GP may be positioned in the central aperture 758C by moving the guide pin GP in the direction D1, through the augment 760 and then into the bone B.

The implant 752 may be secured at surgical site S at step 198T, which may occur subsequent to positioning the implant 752 according to the predetermined surgical plan. A respective fastener F may be positioned in each of the respective peripheral apertures 758P and then into the bone B to secure the implant 752, as illustrated in FIGS. 47D-47E.

Figure 45:
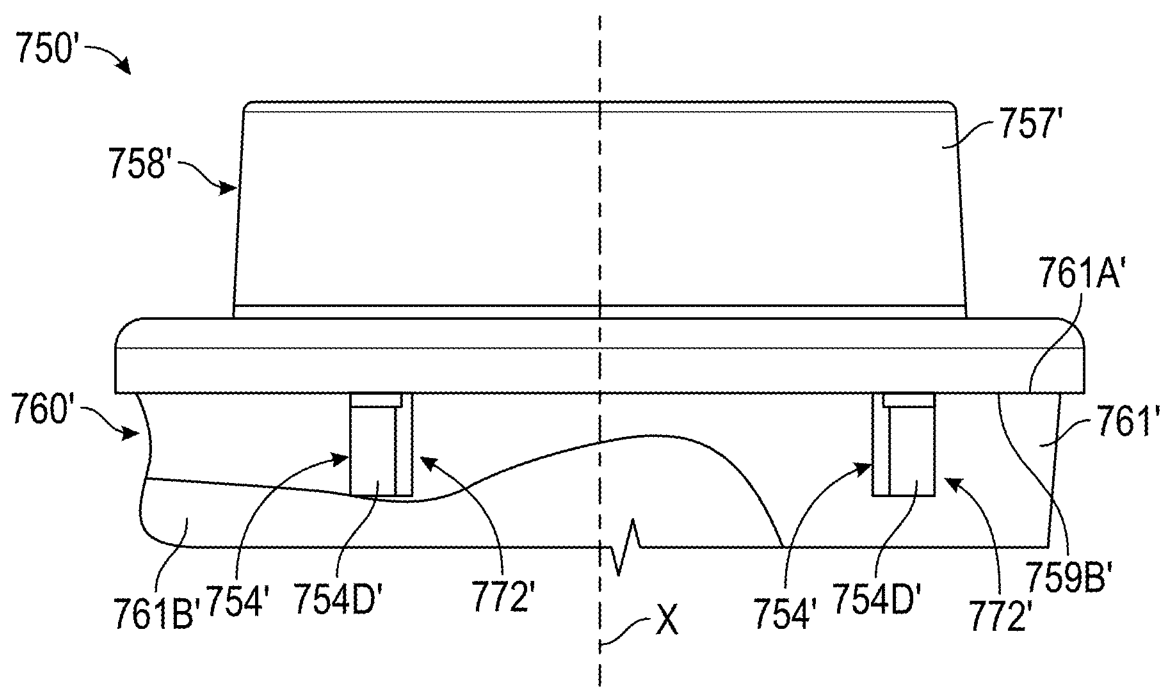
FIG. 45 illustrates a severed state of the breakable connections of FIG. 39.
Figure 46:
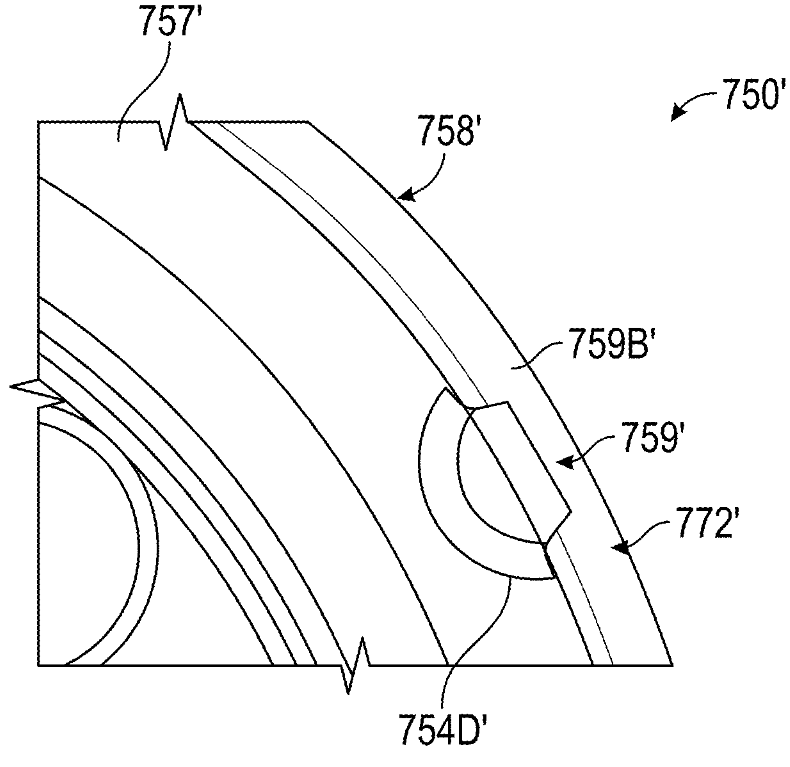
FIG. 46 illustrates another view of one of the severed breakable connections of FIG. 45.
Figure 47F:
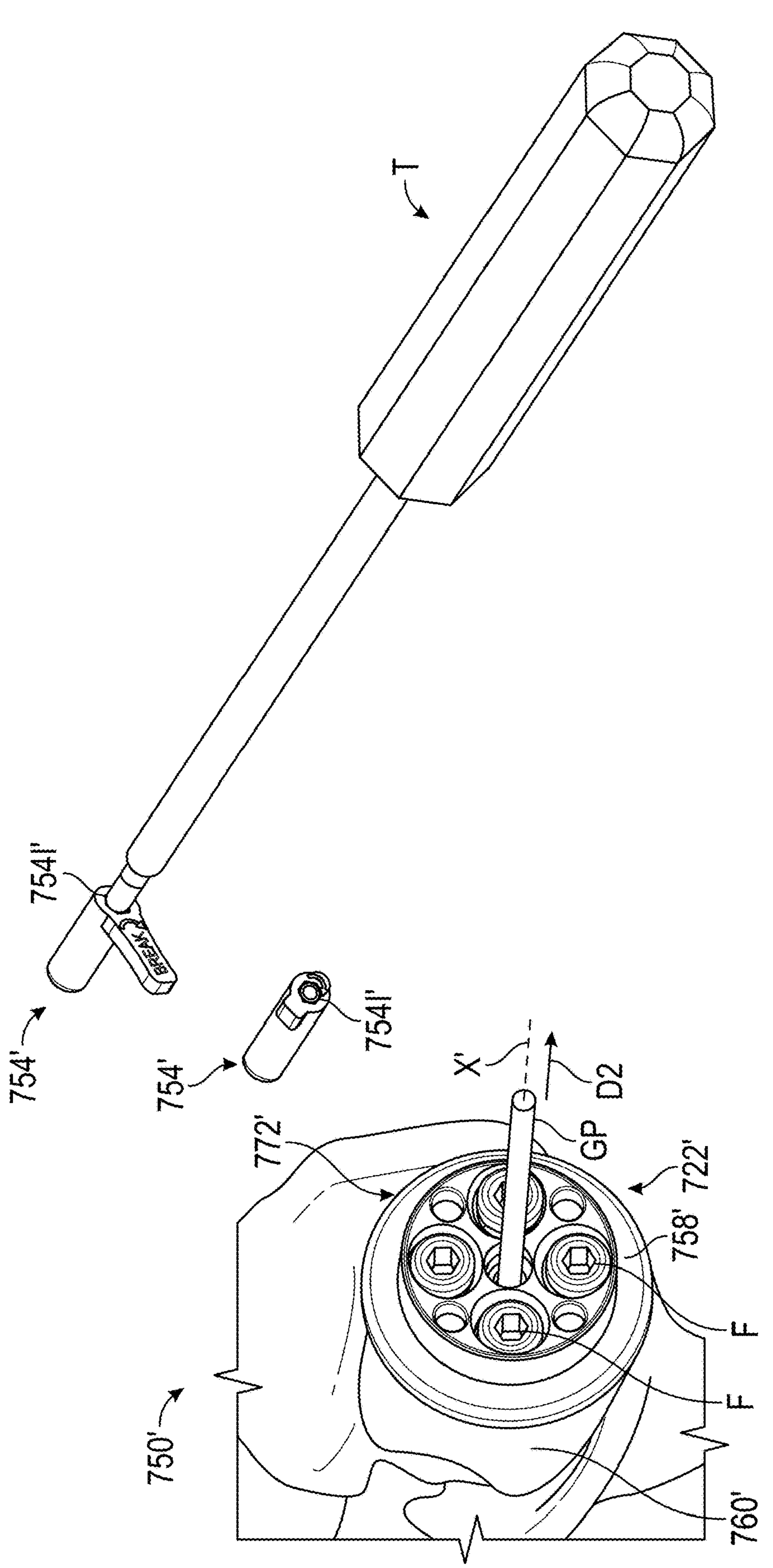
FIG. 47F illustrates the transfer members of FIG. 47E severed from the implant utilizing the tooling.

Referring to FIG. 47E, with continuing reference to FIG. 14, at step 198S the transfer members 754 may be removed from the implant 752. Step 198S may include moving the tooling T along the respective interface axis IA and into engagement with each of the transfer members 754 at the interface 754I. Step 198S may include severing each of the breakable connections 772 in response to causing the tooling T to apply a predetermined quantity of torque or force to the respective transfer member 754 at the interface 754I, such as in the first rotational direction RD1 or one of the directions D3, D4 (FIG. 42). A severed state of the assembly 750' and breakable connections 772' is illustrated in FIGS. 45-46 and 47F. The tooling T may include a retention feature to secure the severed transfer member 754' for limiting separation of the transfer member 754' from the tooling T subsequent to the severing, which can improve removal of the transfer member 754' from the surgical site. Exemplary retention features may include a grasper (e.g., a set of jaws) that interfaces with a periphery of the transfer member 754, a ball plunger configuration, or a ridge in a socket of the interface 754I that engages a protrusion along an end portion of the tooling T in response to rotation of the tooling T.

FIGS. 48-52 illustrate a method of forming an orthopaedic implant assembly in a flowchart 896. The assembly may be utilized to perform an arthroplasty for restoring functionality to any of the joints disclosed herein. The method may be utilized with the planning system 20 to form any of the implant assemblies disclosed herein, including the assemblies 150, 250, 350, 450, 550, 650, 750 and/or 950, according to a predetermined (e.g., preoperative) surgical plan, which may be established according to any of the techniques disclosed herein. The planning system 20 and any of associated modules may be configured to execute each of the steps of the method 896. Fewer or additional steps than are recited below could be performed within the scope of this disclosure, and any recited order of the steps is not intended to limit this disclosure. Reference is made to FIGS. 49-53, which illustrate various states or conditions of an exemplary orthopaedic implant assembly 950 which may be formed utilizing the method 896. The method 896 may be utilized to form the transfer members and associated implant assembly at step 198L of method 198.

At step 896A, a predetermined surgical plan may be established. The surgical plan may include one or more dimensions associated with one or more transfer members relative to a surface profile of tissue such as bone of a respective patient. The surgical plan may be established utilizing any of the techniques utilized herein, including the planning system 20 and step 198J of the method 198. Step 896A may include setting or determining one or more positioning parameters at step 896B. The positioning parameters may include any of the parameters disclosed herein, including a virtual position VP, virtual axis VA and/or contact point(s) CP determined at step 198G of the method 198. Step 896A may include accessing one or more records 41 in the database 29 associated with one or more transfer model(s) 48, implant model(s) 32 and/or surgical plan(s) 33 (FIG. 2).

Figure 48:
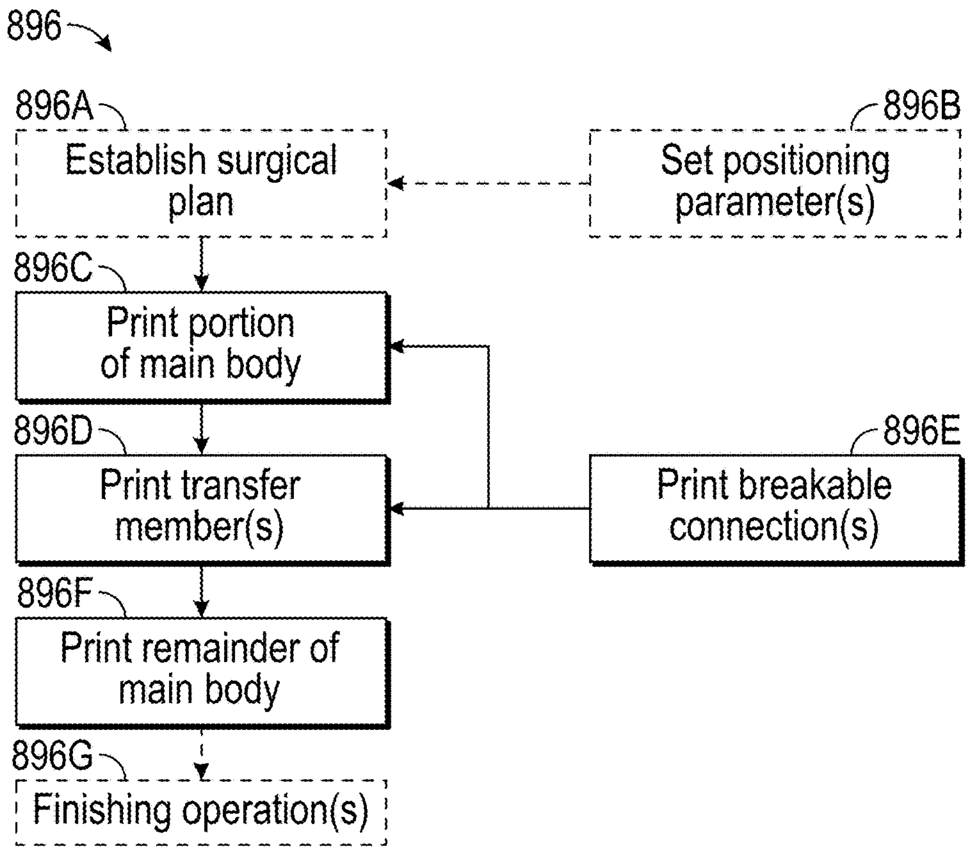
FIG. 48 illustrates an exemplary method of forming an orthopaedic implant assembly.
Figure 49:
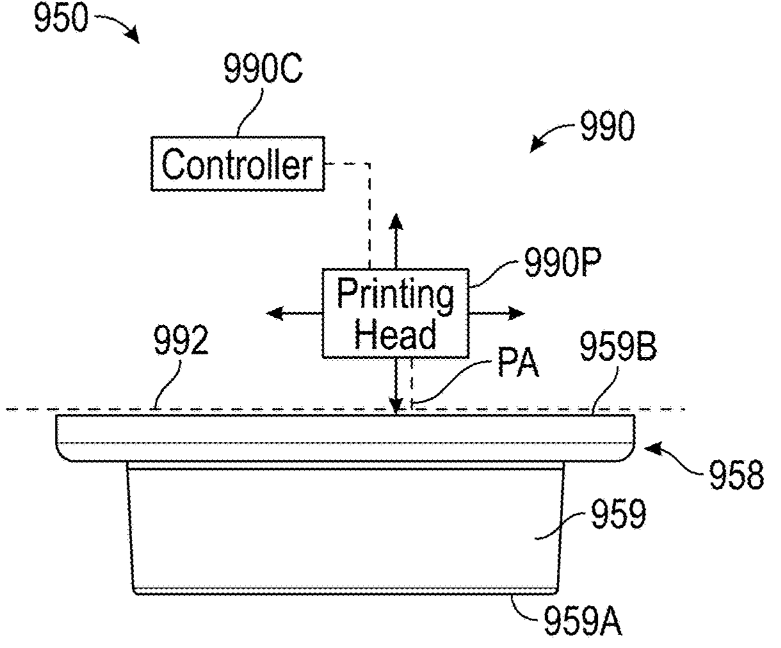
FIG. 49 illustrates a printing assembly positioned relative to a substrate.

Referring to FIG. 49, with continuing reference to FIG. 48, various techniques may be utilized to form the assembly 950. The method may utilize a printing assembly 990 to form the assembly 950. The printing assembly 990 may incorporate a three-dimensional (3D) printing head 990P coupled to a controller 990C. The printing head 990P may be positioned relative to a substrate 992 to form the assembly 950 (substrate 992 shown in dashed lines for illustrative purposes). The controller 990C may be operable to obtain coordinate information corresponding to a predetermined geometry of the assembly 950 and may be operable to command the printing head 990P to perform a series of passes to form successive layers of material on the substrate 992. The printing assembly 990 may be operable to form the assembly 950 utilizing any of the materials disclosed herein, including metallic and/or non-metallic materials. Three-dimensional printers are known, but utilization of three-dimensional printers to form the disclosed implant assemblies is not known.

Figure 50:
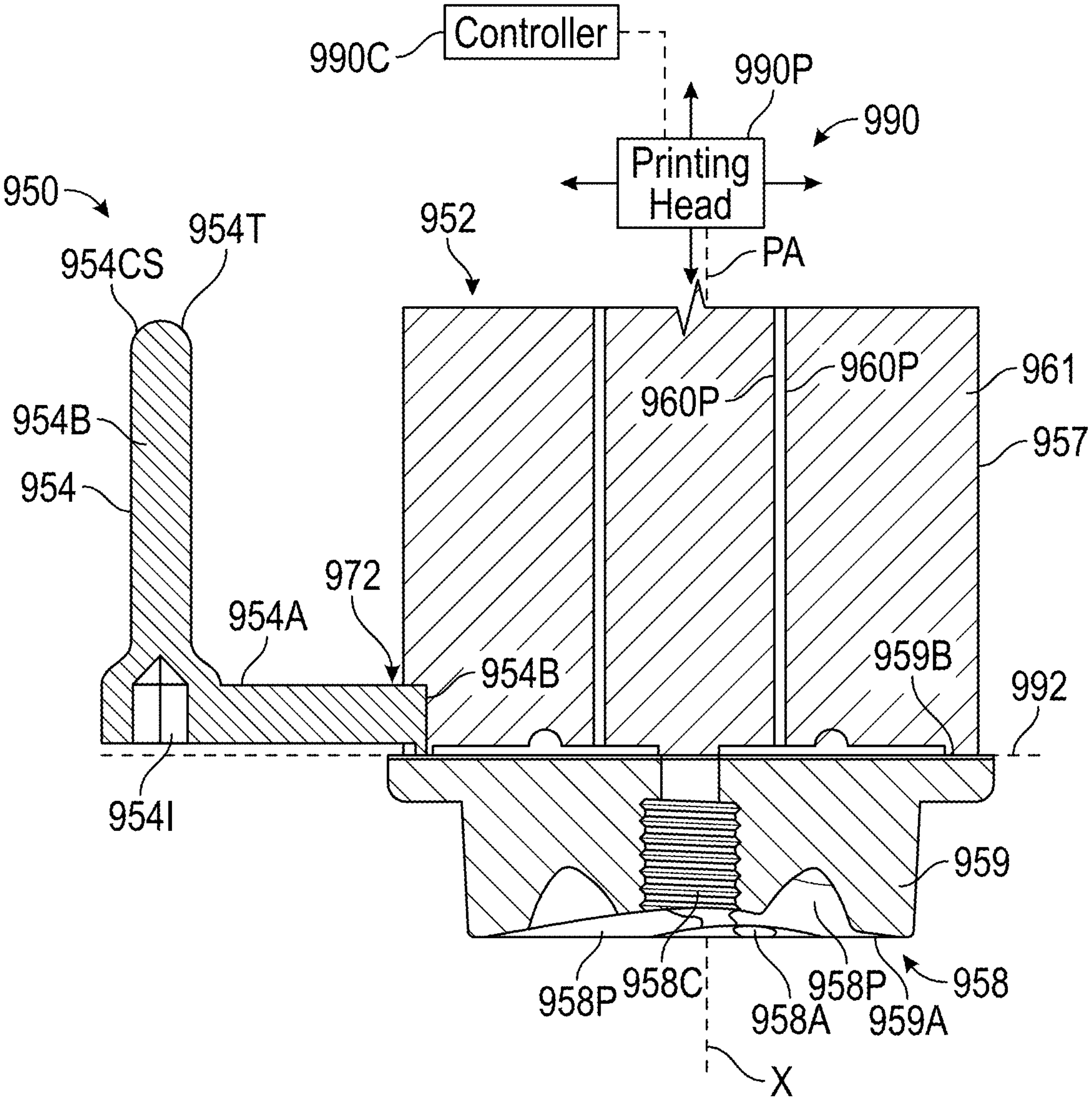
FIG. 50 illustrates a portion of an orthopaedic assembly formed by the printing assembly.
Figure 51:
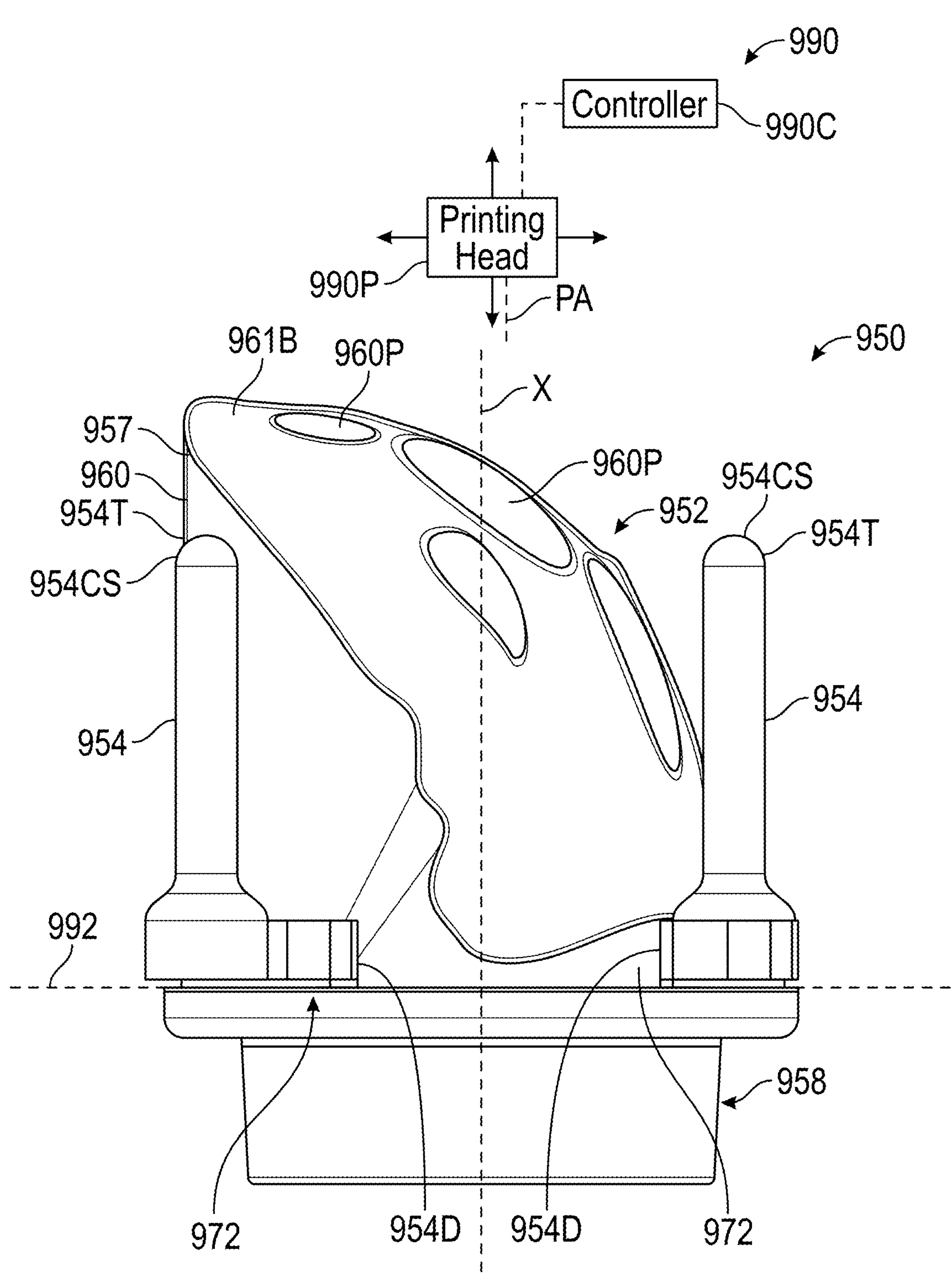
FIG. 51 illustrates a side view of the orthopaedic assembly formed by the printing assembly.

Referring to FIGS. 50-51, with continuing reference to FIGS. 48-49, the printing assembly 990 may print or otherwise form a portion of a main body 957 of an implant 952 on the substrate 992 at step 896C. The main body 957 may include a baseplate 958 and augment 960 extending from the baseplate 958. The substrate 992 may be separate and distinct from the implant 952. In implementations, the substrate 992 is a prefabricated portion of the implant 952, such as the baseplate 958. The baseplate 958 may include a plate body 959 extending between a first (e.g., front) face 959A and a second (e.g., rear) face 959B along a longitudinal (e.g., central) axis X of the implant 952. In implementations, step 896C may include printing the plate body 959 of the baseplate 958 to establish one or more apertures. The apertures may include a central aperture 958C and one or more peripheral apertures 958P and other apertures 958A extending between the front face 959A and rear face 959B of the plate body 959.

Step 896C may include printing or otherwise forming an augment 960 including an augment body 961 onto the rear face 959B of the baseplate 958. Step 896C may occur such that that the augment 960 may extend outwardly from the baseplate 958. The augment body 961 may include a second (e.g., rear) face 961B dimensioned to contact bone. The rear face 961B and/or another surface of the augment 960 may be dimensioned to substantially follow a surface contour of the bone based on a predetermined surgical plan.

Figure 53:
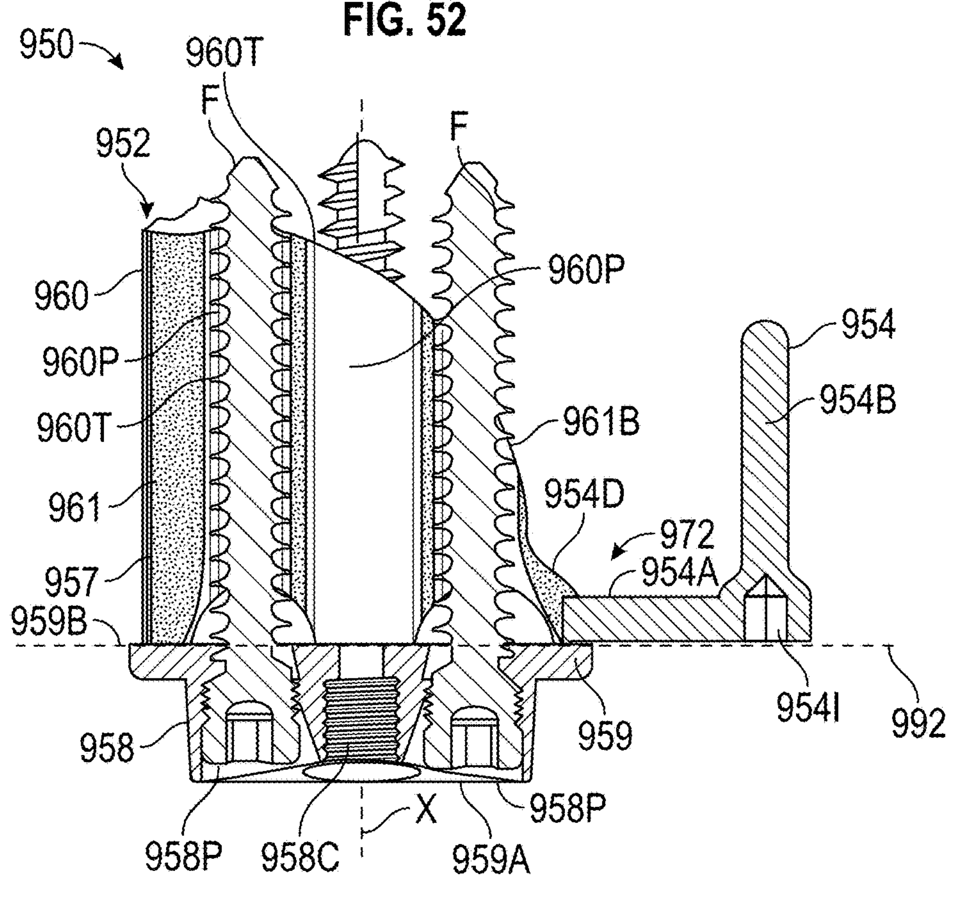
FIG. 53 illustrates a sectional view of the assembly of FIG. 52.

Step 896C may including printing or otherwise forming the portion of the main body 957 to establish one or more passages 960P. The passages 960P may extend through the augment body 961. The passages 960P may be at least partially axially aligned with a respective one of the central aperture 958C and peripheral apertures 958P and may be dimensioned to receive a respective fastener F to secure the implant 952 to bone, as illustrated in FIG. 53. Step 896C may include printing one or more tubular members 960T to establish the passages 960P (see FIG. 53). Step 896C may include printing a portion of the augment body 961 to at least partially surround the tubular members 960T. In some implementations, the tubular members 960T are omitted and the augment body 961 establishes the passages 960P.

The augment body 961 may be substantially solid or may include a porous scaffold that at least partially surrounds the tubular members 960T. The scaffold may establish an external surface of the augment 960.

At step 896D, the method may include printing or otherwise forming one or more transfer members 954 such that the transfer members 954 are coupled to the implant 952. Step 896D may include integrally forming the transfer members 954 with the augment 960 or another portion of the main body 957 of the implant 952 based on the dimension(s) and/or other parameters associated with the surgical plan established at step 896A.

Each of the transfer members 954 may include a respective contact surface 954CS. The contact surface 954CS may include any of the geometries disclosed herein, including a patient-specific or non-patient specific geometry. Step 896D may include forming the contact surface 954CS to substantially follow the surface profile of a bone based on the surgical plan (see, e.g., contact surface 354CS of FIG. 26).

The method may include printing or otherwise forming one or more breakable connections 972 to couple respective transfer members 954 to the implant 952 at step 896E. Step 896E may be separately performed, or may be concurrently performed with steps 896C and/or 986D. The breakable connections 972 can include any of the breakable connections disclosed herein. Each breakable connection 972 may be integrally formed with and interconnect the respective transfer members 954 to a wall of the main body 957 of the implant 952. Step 896D may include printing or otherwise forming an interface 9541 associated with the transfer member 954. Each breakable connection 972 may be formed at step 896E such that the breakable connection 972 severs in response to a predetermined quantity of torque or force applied to the interface 9541 of the respective transfer member 954. The predetermined quantity of torque or force may be established by one or more dimensions or parameters set or established at step 896B. Various techniques may be utilized to establish each breakable connection 972. The breakable connections 972 may be established by a reduced thickness, scoring, perforations, and/or different material compositions (e.g., different densities), etc., to facilitate severing the transfer members 954 from the main body 957 of the implant 952.

Referring to FIG. 51, with continuing reference to FIG. 48, a remainder of the implant 952 may be printed or otherwise formed at step 896F. Step 896F may include printing or otherwise forming a reminder of the main body 957 of the implant 952 including a remainder of the augment 960.

Steps 896C-896F may be performed such that substantially all portions of the assembly 950 are printed or otherwise formed together to establish a monolithic or unitary component. For example, steps 896C-896F may be performed such that at least the baseplate 958, augment 960 and transfer members 954 are printed or integrally formed together to establish a monolithic or unitary component.

Figure 52:
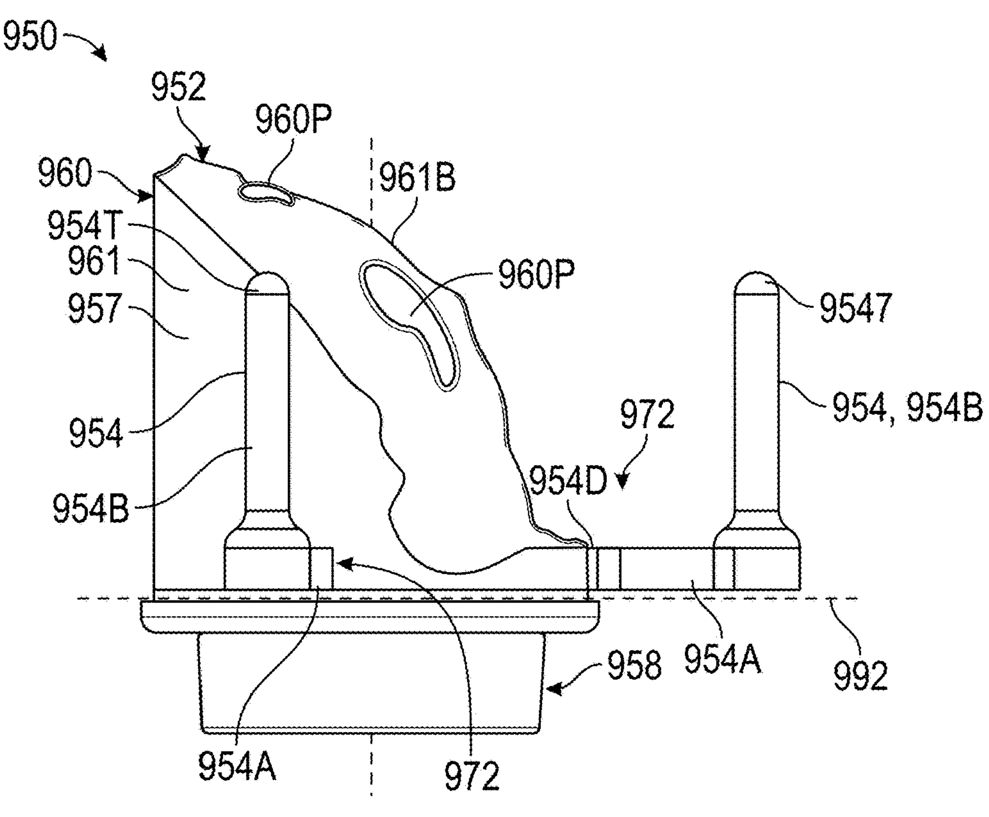
FIG. 52 illustrates another side view of the orthopaedic assembly of FIG. 51.

The method may include performing one or more finishing operations on the assembly 950 at step 896G. Step 896G may include machining surfaces of the implant 952 according to a predetermined geometry. Step 896G may include applying one or more treatments to the assembly 950, including applying surface coatings and treatments to the implant 952. FIGS. 51-53 illustrate a substantially or completely finished state of the assembly 950. Step 896G may include placing the assembly 950 in sterile packaging for conveyance to the surgeon or associated facility.

The novel planning systems, assemblies and methods of this disclosure can be incorporated into a practical application by providing improved positioning of implants relative to patient anatomy. The disclosed techniques may reduce a complexity in preparing for and performing a surgical procedure according to a predetermined surgical plan, including implementing the surgical plan by positioning implants in a manner that closely corresponds to one or more parameters specified in the surgical plan. The disclosed techniques may more accurately position associated implants, which may lead to improved healing. The disclosed transfer members and/or implant surfaces may be dimensioned with respect to the patient anatomy, which may more accurately position the implant. The disclosed techniques may be utilized to couple the transfer members to the implant, which may reduce instrumentation and complexity. In implementations, the disclosed assemblies may omit a separate transfer guide by coupling the transfer members directly to the implant, which may reduce separate instrumentation and packaging. The disclosed transfer guides may be reusable, which may reduce cost and training associated with implementing different surgical plans.

Although the different non-limiting implementations are illustrated as having specific components or steps, the implementations of this disclosure are not limited to those particular combinations. It is possible to use some of the components or features from any of the non-limiting implementations in combination with features or components from any of the other non-limiting implementations.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. An orthopaedic implant comprising:

a baseplate including a plate body extending along an implant axis between a front face and a rear face;

an augment extending outwardly from the rear face of the baseplate, the augment dimensioned to contact bone; and one or more transfer members extending from the augment and coupled to the augment at a respective breakable connection, wherein the one or more transfer members are configured to contact bone, and wherein the one or more transfer members include a first portion extending radially outward from a periphery of the augment relative to the implant axis and a second portion extending axially from the first portion relative to the implant axis.

2. The implant as recited in claim 1, wherein the one or more transfer members are dimensioned based on a predetermined surgical plan.

3. The implant as recited in claim 1, wherein the one or more transfer members are integrally formed with the augment.

4. The implant as recited in claim 1, wherein the augment is formed along the baseplate.

5. The implant as recited in claim 1, wherein the breakable connection is configured to sever in response to a predetermined quantity of torque at an interface.

6. The implant as recited in claim 5, wherein the breakable connection is configured to sever in response to the predetermined quantity of torque in a first rotational direction with respect to an axis extending through the interface, but not a second rotational direction opposed to the first rotational direction.

7. The implant as recited in claim 1, wherein the one or more transfer members include a plurality of transfer members circumferentially distributed about the periphery of the augment.

8. The implant as recited in claim 7, wherein each of the transfer members includes a terminal end portion configured to contact tissue.

9. The implant as recited in claim 8, wherein the breakable connection is configured to sever in response to a predetermined quantity of torque in a first rotational direction with respect to an axis extending through the second portion, but not a second rotational direction opposed to the first rotational direction.

10. The implant as recited in claim 1, wherein the baseplate includes a central aperture and a plurality of peripheral apertures circumferentially distributed about the central aperture, the peripheral apertures are aligned with respective passages through the augment and are dimensioned to receive respective fasteners partially receivable through the respective passages and into bone.

11. The implant as recited in claim 10, wherein the central aperture is dimensioned to receive a guide pin insertable into bone to set a position of the implant.

* * * * *